(12) United States Patent
Tanabe et al.

(10) Patent No.: US 8,735,610 B2
(45) Date of Patent: May 27, 2014

(54) ELECTROLUMINESCENT DEVICE

(75) Inventors: Junichi Tanabe, Amagasaki (JP);
Hidetaka Oka, Takarazuka (JP);
Hiroshi Yamamoto, Nishinomiya (JP)

(73) Assignee: BASF SE, Ludwigshafen (DE)

( * ) Notice: Subject to any disclaimer, the term of this patent is extended or adjusted under 35 U.S.C. 154(b) by 105 days.

(21) Appl. No.: 13/164,016

(22) Filed: Jun. 20, 2011

(65) Prior Publication Data

US 2011/0248217 A1 Oct. 13, 2011

Related U.S. Application Data

(62) Division of application No. 11/921,050, filed as application No. PCT/EP2006/062483 on May 22, 2006, now Pat. No. 7,989,644.

(30) Foreign Application Priority Data

May 30, 2005 (EP) .................................... 05104599
Aug. 30, 2005 (EP) .................................... 05107908

(51) Int. Cl.
*C07D 407/02* (2006.01)
*H01L 51/50* (2006.01)

(52) U.S. Cl.
USPC .......................................... 549/460; 313/504

(58) Field of Classification Search
USPC .......................................... 549/460; 313/504
See application file for complete search history.

(56) References Cited

U.S. PATENT DOCUMENTS

| | | | |
|---|---|---|---|
| 4,016,156 A | 4/1977 | Weber et al. | |
| 6,229,012 B1 | 5/2001 | Hu et al. | |
| 8,231,983 B2 | 7/2012 | Sugita et al. | |
| 2004/0076853 A1 | 4/2004 | Jarikov | |
| 2005/0238920 A1 | 10/2005 | Sotoyama et al. | |
| 2007/0247063 A1 | 10/2007 | Murase et al. | |

FOREIGN PATENT DOCUMENTS

| | | |
|---|---|---|
| EP | 0879868 A2 | 11/1998 |
| EP | 1344788 | 9/2003 |
| JP | 62-280850 | 5/1987 |
| JP | 4-181261 | 6/1992 |
| JP | 06271844 | 9/1994 |
| JP | 07-053950 | 2/1995 |
| JP | 09151182 | 6/1997 |
| JP | 11111460 | 4/1999 |
| JP | 11-354281 | 12/1999 |
| JP | 2000012230 | 1/2000 |
| JP | 2001-043979 | 2/2001 |
| JP | 2003-286260 | 10/2003 |
| JP | 2005314239 | 4/2004 |
| JP | 2004-196716 | 7/2004 |
| JP | 2004-311404 A | 11/2004 |
| JP | 2004-311405 | 11/2004 |
| JP | 2005112765 | 4/2005 |
| WO | 2004096945 | 11/2004 |
| WO | 2005113531 | 12/2005 |
| WO | 2006/114966 A1 | 11/2006 |

OTHER PUBLICATIONS

Yan, Y-Y. et al.: Chiral binaphthyl ligands with buttressing substituents. Monat. fur. Chemie, vol. 130, pp. 873-885,1999.*
Garmatter, J. et al.: Anil synthesis. Preparation of styryl derivatives of dibenzofurans. Helvetica Chim. Acta, vol. 57, pp. 945-979, 1974.*
Translation of JP 07-053950 (Feb. 28, 1995).
Translation of JP 2001-043979 (Feb. 16, 2001).
Translation of Abstract of JP 4-181261 (Jun. 29, 1992).
Translation of JP 62-280850 (May 5, 1987).
Translation of JP 11-354281 (Dec. 24, 1999).
Translation of Abstract & Claims only of JP 2004-311405 (Nov. 4, 2004).
Translation of JP 2004-196716 (Jul. 15, 2004).
Translation of Abstract & Claims only of JP 2003-286260 (Oct. 10, 2003).
Fujiwara et al., Journal of Organic Chemistry, 1981, 46, pp. 851-855.
Wirth et al., Makromolekulare Chemie, Macromolecular Chemistry and Physics, vol. 86, No. 16, 1965 pp. 139-167.
Journal of Applied Spectroscopy, vol. 46 (1987) pp. 40-43.
Hely. Chim. Acta 52 (1969) pp. 1282-1322.
J. Am. Chem. Soc. vol. 115 (1993) pp. 11506-11511.
J. Am. Chem. Soc. Vo. 114 (1992) pp. 10775-11783.

* cited by examiner

*Primary Examiner* — Charanjit Aulakh
(74) *Attorney, Agent, or Firm* — Shiela A. Loggins

(57) ABSTRACT

Disclosed are electroluminescent devices that comprise organic layers that contain dibenzofuran compounds. The compounds are suitable components of, for example, blue-emitting, durable, organo-electroluminescent layers. The electroluminescent devices may be employed for full color display panels in, for example, mobile phones, televisions and personal computer screens.

8 Claims, No Drawings

ELECTROLUMINESCENT DEVICE

This is a divisional of the U.S. application Ser. No. 11/921,050, filed Nov. 26, 2007 now U.S. Pat. No. 7,989,644, which is a national stage application which takes the benefit of international application No. PCT/EP06/062483, filed May 22, 2006.

The present invention relates to electroluminescent devices that comprise organic layers that contain dibenzofuran compounds. The compounds are suitable components of, for example, blue-emitting, durable, organo-electroluminescent layers. The electroluminescent devices may be employed for full color display panels in, for example, mobile phones, televisions and personal computer screens.

H. O. Wirth et al., Die Makromolekulare Chemie 86 (1965) 139-167 describes the synthesis and properties of oxydo-p-oligophenylenes. The following two dibenzofuran compounds are described therein:

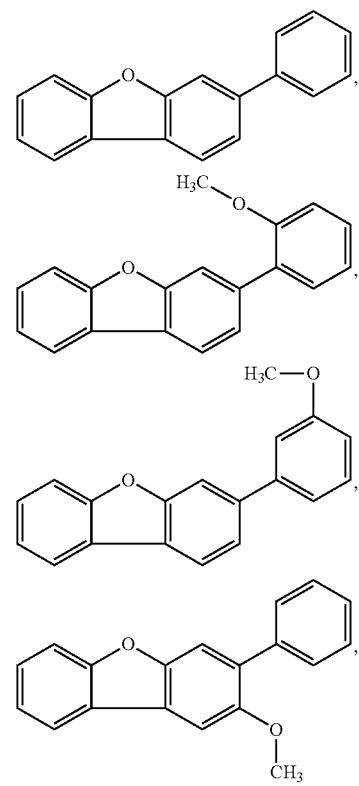

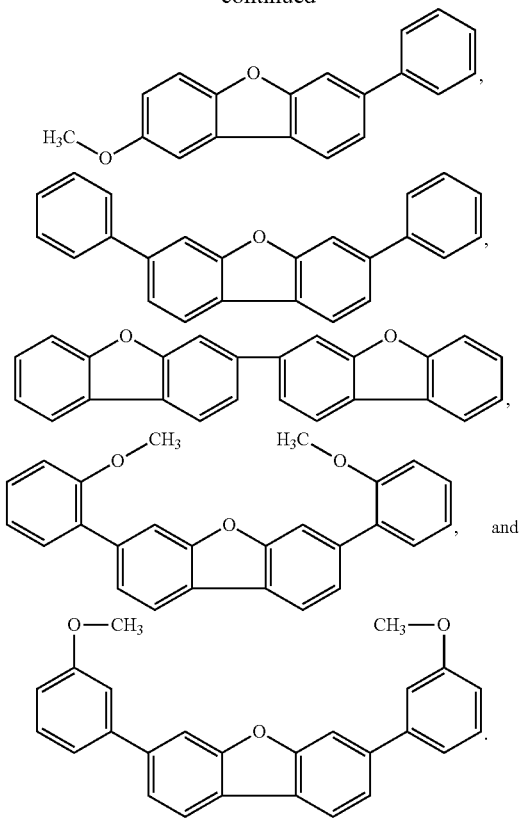

JP9151182 discloses dibenzofurandiamine derivatives, which are suitable as a positive hole transporting agent, etc., in electrophotographic photoreceptor, solar cell, electroluminescence element etc. The dibenzofurandiamine derivatives are represented by the following formula

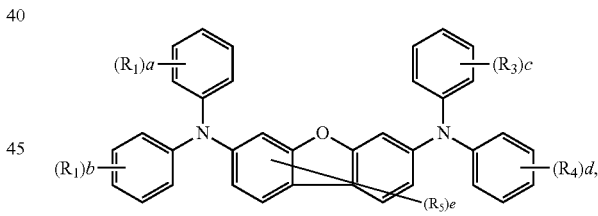

wherein $R_1$ to $R_5$ are each a halogen, a (substituted)alkyl, a (substituted)alkoxy, a (substituted)aryl or (substituted)aralkyl; (a), (b), (c) and (d) are each 0-5; (e) is 0-6. The following compounds are explicitly disclosed in JP9151182:

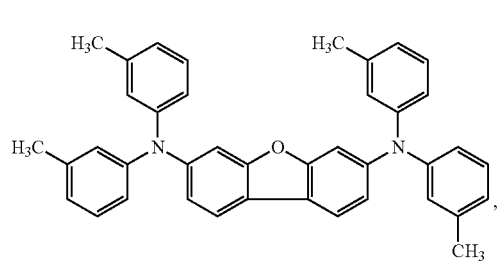

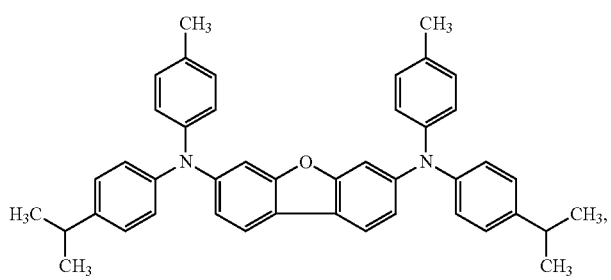

-continued

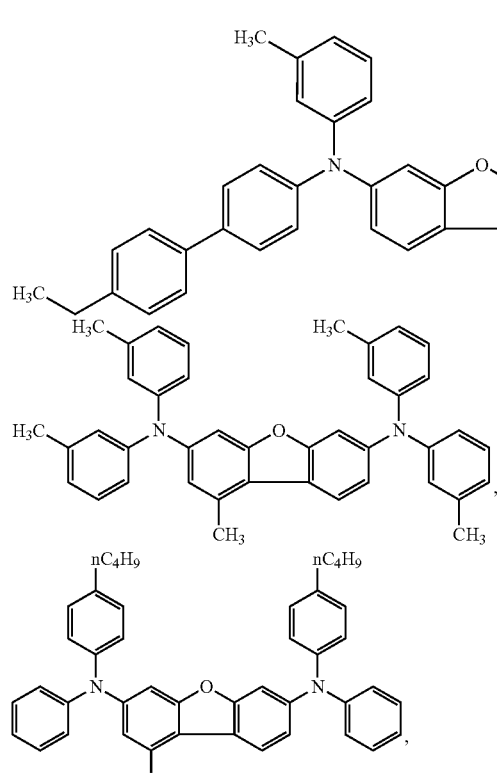

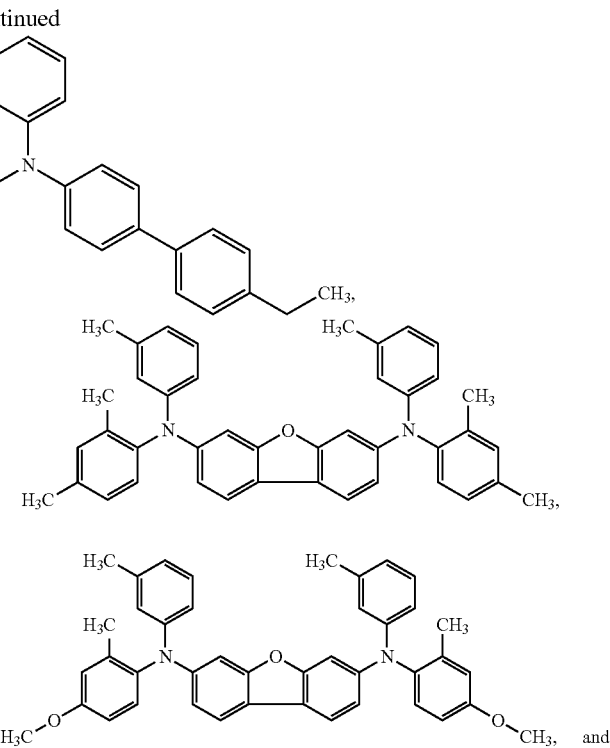

JP2004311404 discloses compounds having at least one biaryl part structure for use in OLED application. The dimeric dibenzofuran compound shown below is explicitly mentioned.

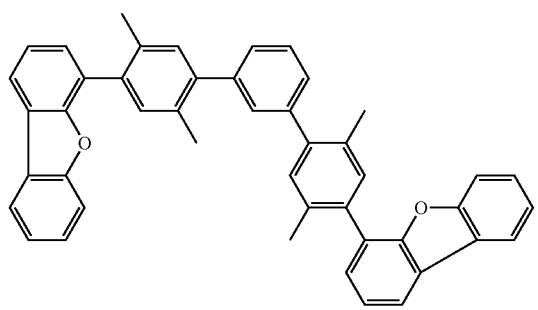 [SMILES: Cc1cc(-c2cccc3c2oc2ccccc23)c(C)cc1-c1cccc(-c2cc(C)c(-c3cccc4c3oc3ccccc34)cc2C)c1]

WO03105538 relates to benzotriazole compounds and their use in OLED application. The dimeric benzotriazole compound shown below is explicitly mentioned.

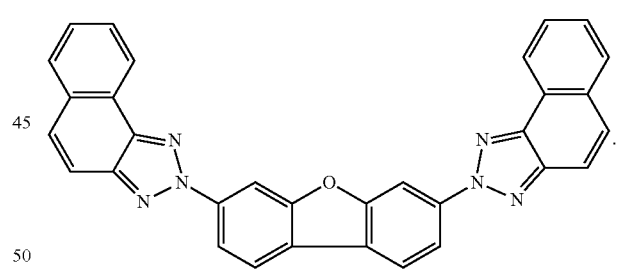

The compounds shown below are also known:

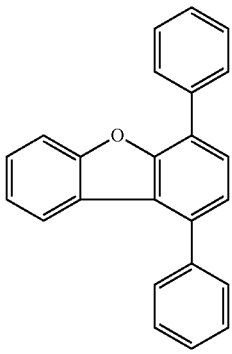 [SMILES: c1ccc(-c2ccc(-c3ccccc3)c3c2oc2ccccc23)cc1]

(J. Chem. Soc. (1962) 5291,

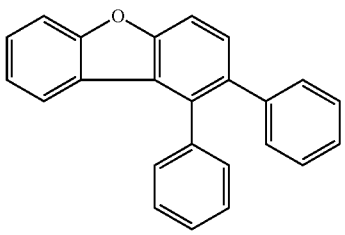 [SMILES: c1ccc(-c2ccc3oc4ccccc4c3c2-c2ccccc2)cc1]

(J. Chem. Soc. (1962) 5291,

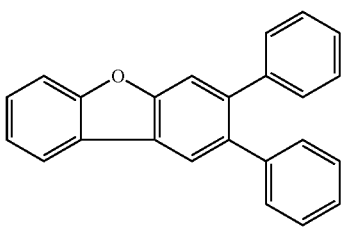 [SMILES: c1ccc(-c2cc3oc4ccccc4c3cc2-c2ccccc2)cc1]

(J. Org. Chem. 46 (1981) 851-855),

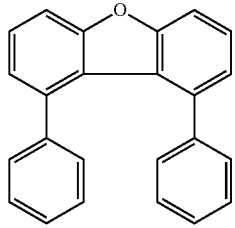 [SMILES: c1ccc(-c2cccc3oc4cccc(-c5ccccc5)c4c23)cc1]

(Bull. Chem. Soc. Japan 9 (1934) 55), and

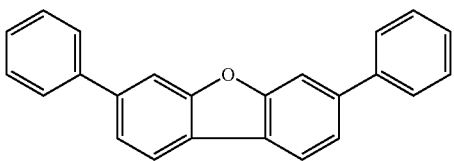 [SMILES: c1ccc(-c2ccc3c(c2)oc2cc(-c4ccccc4)ccc23)cc1]

(Bull. Chem. Soc. Japan 9 (1934) 55).

Surprisingly, it was found that luminescent devices, which are high durability besides high in the efficiency of electrical energy utilisation and high in luminance, can be obtained if specific benzofuran compounds are used, especially as light emitting substances.

Accordingly, the present invention relates to compounds of the formula

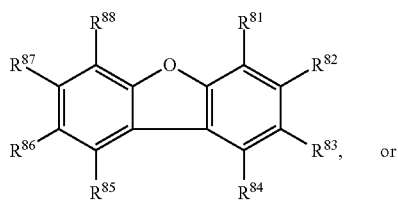

(I)

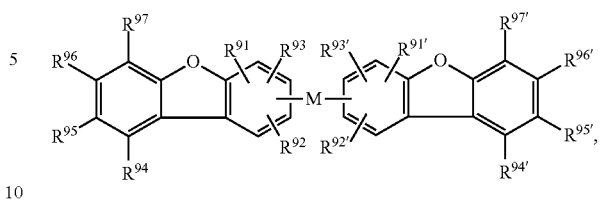

(II)

wherein $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are independently of each other H, —$OR^{201}$, —$SR^{202}$ and/or —$NR^{203}R^{204}$, $C_1$-$C_{24}$alkyl; $C_1$-$C_{24}$alkyl, which is substituted by E and/or interrupted by D; $C_2$-$C_{18}$alkenyl, $C_2$-$C_{18}$alkenyl, which is substituted by E, $C_3$-$C_8$cycloalkyl, $C_3$-$C_8$cycloalkyl, which is substituted by G, aryl, aryl, which is substituted by G, heteroaryl, or heteroaryl, which is substituted by G, silyl,

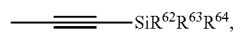

—CN, cyclic ether, —$B(OR^{65})_2$ and/or halogen, especially fluorine, or $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, $R^{97}$ and $R^{96}$, $R^{96}$ and $R^{95}$, $R^{95}$ and $R^{94}$, $R^{97'}$ and $R^{96'}$, $R^{96'}$ and $R^{95'}$, $R^{95'}$ and/or $R^{94'}$, and/or two of the groups $R^{91}$, $R^{92}$ and $R^{93}$ or $R^{91'}$, $R^{92'}$ and $R^{93'}$, which are in neighbourhood to each other, together form a group

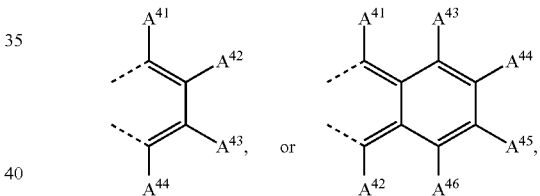

wherein $A^{41}$, $A^{42}$, $A^{43}$, $A^{44}$, $A^{45}$, $A^{46}$ and $A^{47}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by G and/or interrupted by S—, —O—, or —$NR^5$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by E, or —CO—$R^8$, M is a bonding group, such as a single (direct) bond, —CO—, —COO—; —S—; —SO—; —$SO_2$—; —O—; $C_1$-$C_{12}$alkylene, $C_2$-$C_{12}$alkenylene, or $C_2$-$C_{12}$alkinylene, which are optionally interrupted by one or more —O—, or —S—; or a group $[M^1]_n$, wherein n is an integer 1 to 20, $M^1$ is arylene, or heteroarylene, which is optionally substituted by G, especially naphthylene, biphenylene, styrylene, anthrylene, or pyrenylene, which are optionally substituted by $C_1$-$C_{12}$alkyl, halogen, —$OR^{201}$, —$SR^{202}$ and/or —$NR^{203}R^{204}$, wherein $R^{201}$ is hydrogen, $C_1$-$C_{24}$alkyl, $C_1$-$C_{24}$alkyl, which is substituted by E and/or interrupted by D; $C_2$-$C_{12}$alkenyl, $C_3$-$C_6$alkenoyl, $C_3$-$C_8$cycloalkyl, or benzoyl, each of which may optionally be substituted by one or more groups $C_1$-$C_6$alkyl, halogen, —OH and/or $C_1$-$C_4$alkoxy; $C_6$-$C_{14}$aryl, especially phenyl, naphthyl, phenanthryl, anthranyl, or pyrenyl, each of which may optionally be substituted by halogen, —OH, $C_1$-$C_{12}$alkyl, $C_1$-$C_{12}$alkoxy, phenoxy, $C_1$-$C_{12}$alkylsulfanyl, phenylsulfanyl, —N($C_1$-$C_{12}$alkyl)$_2$ and/or diphenylamino;

$R^{202}$ is $C_{24}$alkyl, $C_1$-$C_{24}$alkyl, which is substituted by E and/or interrupted by D; $C_2$-$C_{12}$alkenyl, $C_1$-$C_8$alkanoyl, $C_2$-$C_{12}$alkenyl, $C_3$-$C_6$alkenoyl; $C_3$-$C_8$cycloalkyl, or benzoyl, each of which may optionally be substituted by one or more groups $C_1$-$C_6$alkyl, halogen, —OH, $C_1$-$C_4$alkoxy or $C_1$-$C_4$alkylsulfanyl; $C_6$-$C_{14}$aryl, especially phenyl, naphthyl, phenanthryl, anthranyl, or pyrenyl, each of which may optionally be substituted by halogen, $C_1$-$C_{12}$alkyl, $C_1$-$C_{12}$alkoxy, phenyl-$C_1$-$C_3$alkyloxy, phenoxy, $C_1$-$C_{12}$alkylsulfanyl, phenylsulfanyl, —N($C_1$-$C_{12}$alkyl)$_2$, diphenylamino, —(CO)O($C_1$-$C_8$alkyl), —(CO)—$C_1$-$C_8$alkyl, or (CO)N($C_1$-$C_8$alkyl)$_2$;

$R^{203}$ and $R^{204}$ are independently of each other hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, or benzoyl, each of which may optionally be substituted by one or more groups $C_1$-$C_6$alkyl, halogen, —OH, or $C_1$-$C_4$alkoxy; phenyl-$C_1$-$C_3$alkyl, $C_1$-$C_8$alkanoyl, $C_3$-$C_{12}$alkenoyl, $C_6$-$C_{14}$aryl, especially phenyl naphthyl, phenanthryl anthranyl, or pyrenyl, each of which is optionally substituted by $C_1$-$C_{12}$alkyl, benzoyl or $C_1$-$C_{12}$alkoxy; or $R^{203}$ and $R^{204}$ together are $C_2$-$C_8$alkylene, or branched $C_2$-$C_8$alkylene optionally interrupted by —O—, —S—, or —NR$^{205}$— and/or optionally substituted by hydroxyl, $C_1$-$C_4$alkoxy, $C_2$-$C_4$alkanoyloxy, or benzoyloxy, wherein the ring formed by $R^{203}$ and $R^{204}$ can optionally be condensed one or two times by phenyl which can be substituted one to three times with $C_1$-$C_8$-alkyl, $C_1$-$C_8$-alkoxy, halogen, or cyano;

$R^{205}$ is hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, phenyl-$C_1$-$C_3$alkyl, $C_1$-$C_8$alkanoyl, $C_3$-$C_{12}$alkenoyl, $C_6$-$C_{14}$aryl, especially benzoyl; phenyl, naphthyl, phenanthryl, anthranyl, or pyrenyl, each of which is optionally substituted by $C_1$-$C_{12}$alkyl, benzoyl, or $C_1$-$C_{12}$alkoxy;

D is —CO—, —COO—, —OCOO—, —S—, —SO—, —SO$_2$—, —O—, —NR$^5$—, —SiR$^{61}$R$^{62}$—, —POR$^5$—, —CR$^{63}$=CR$^{64}$—, or —C≡C—;

E is halogen, $C_6$-$C_{14}$aryl, especially phenyl, naphthyl, phenanthryl, anthranyl, or pyrenyl, which may be substituted by —OR$^5$, —SR$^5$, —NR$^5$R$^6$, —═—SiR$^{62}$R$^{63}$R$^{64}$, wherein R$^{62}$, R$^{63}$ and R$^{64}$ are independently of each other a $C_1$-$C_8$alkyl group, a $C_6$-$C_{24}$aryl group or a $C_7$-$C_{12}$aralkylgroup, —CN, cyclic ether and/or —B(OR$^{65}$)$_2$, wherein R$^{65}$ is hydrogen, $C_1$-$C_{24}$alkyl, $C_3$-$C_8$cycloalkyl, $C_7$-$C_{24}$aralkyl, $C_2$-$C_{18}$alkenyl, $C_2$-$C_{24}$alkynyl, hydroxy, mercapto, $C_1$-$C_{24}$alkoxy, $C_1$-$C_{24}$alkylthio, $C_6$-$C_{30}$aryl, $C_2$-$C_{30}$heteroaryl, halogen, especially fluorine, haloalkane, silyl, siloxanyl, and an alicyclic ring formed with adjacent substituents R$^{65}$; —OR$^5$, —SR$^5$, —NR$^5$R$^6$, —COR$^8$, —COOR$^7$, —CONR$^5$R$^6$, —CN, halogen, silyl, $C_1$-$C_{18}$alkyl, or heteroaryl, G is E, or $C_1$-$C_{18}$alkyl, wherein R$^5$ and R$^6$ are independently of each other H, $C_6$-$C_{18}$aryl; $C_6$-$C_{18}$aryl which is substituted by $C_1$-$C_{18}$alkyl, $C_1$-$C_{18}$alkoxy, or silyl; $C_1$-$C_{18}$alkyl or $C_1$-$C_{18}$alkyl which is interrupted by —O—; or R$^5$ and R$^6$ together form a five or six membered ring, in particular

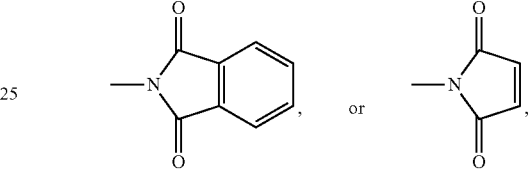

R$^7$ is H, $C_6$-$C_{18}$aryl, $C_7$-$C_{12}$alkylaryl, which are optionally substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

R$^8$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, $C_7$-$C_{12}$alkylaryl, or $C_1$-$C_{18}$alkyl which is interrupted by —O—;

R$^{61}$ and R$^{62}$ are independently of each other $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—, and R$^{63}$ and R$^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—; with the proviso that at least one of R$^{81}$, R$^{82}$, R$^{83}$, R$^{84}$, R$^{85}$, R$^{86}$, R$^{87}$ and R$^{88}$ is different from H, —OR$^{201}$, —SR$^{202}$ and $C_1$-$C_{24}$alkyl; and the further proviso that the following compounds are excluded:

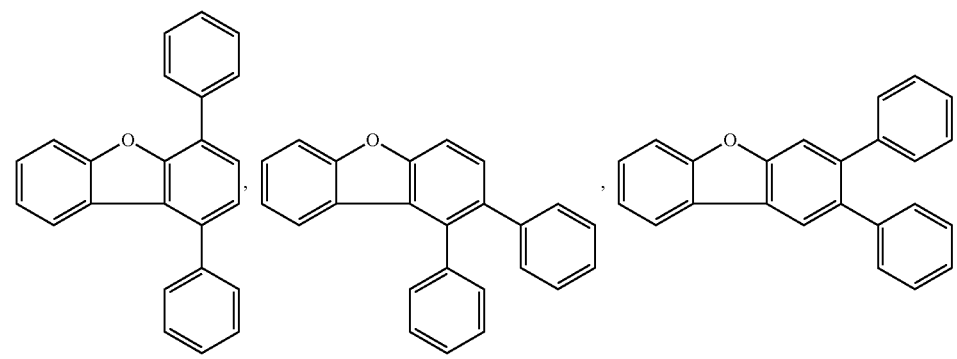

-continued
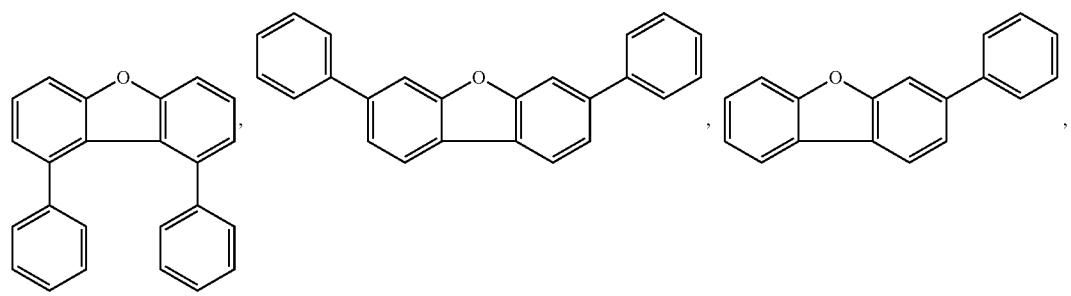
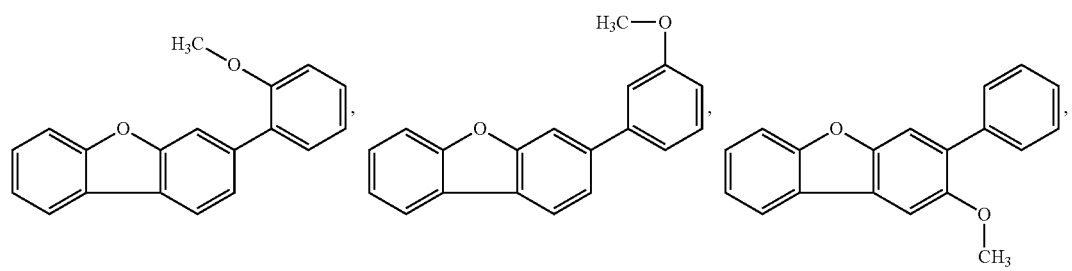
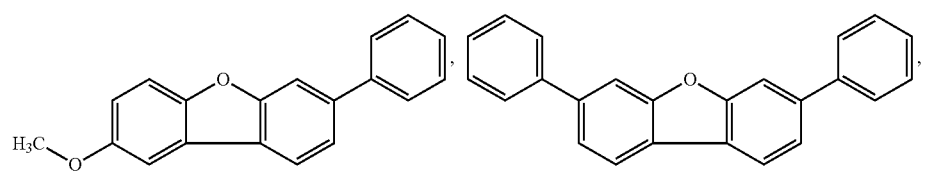
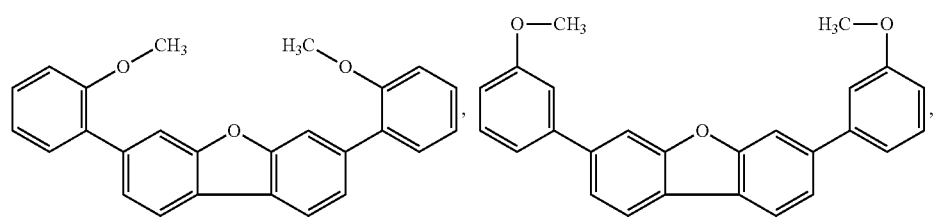
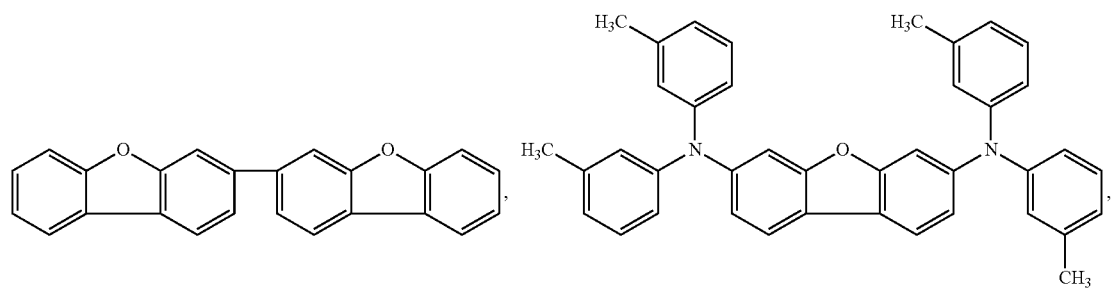
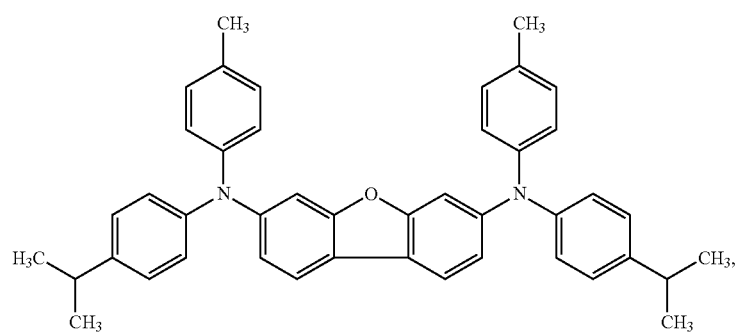

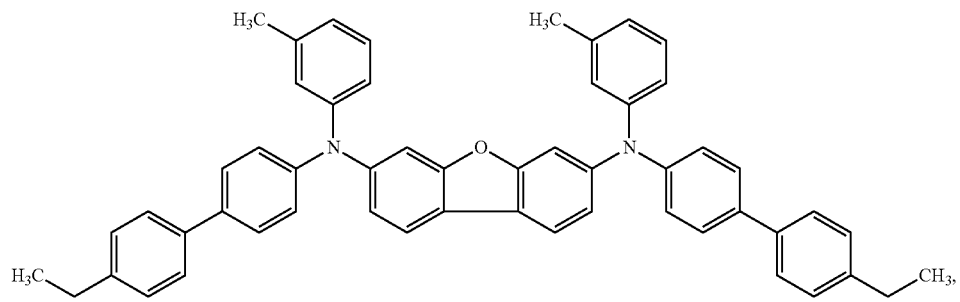
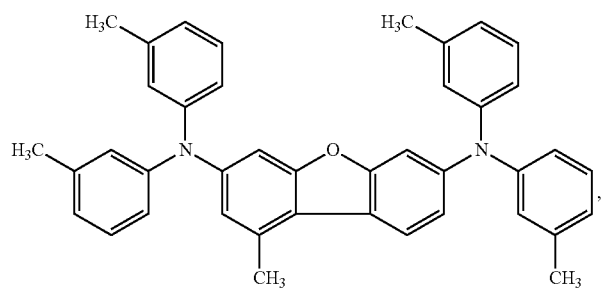
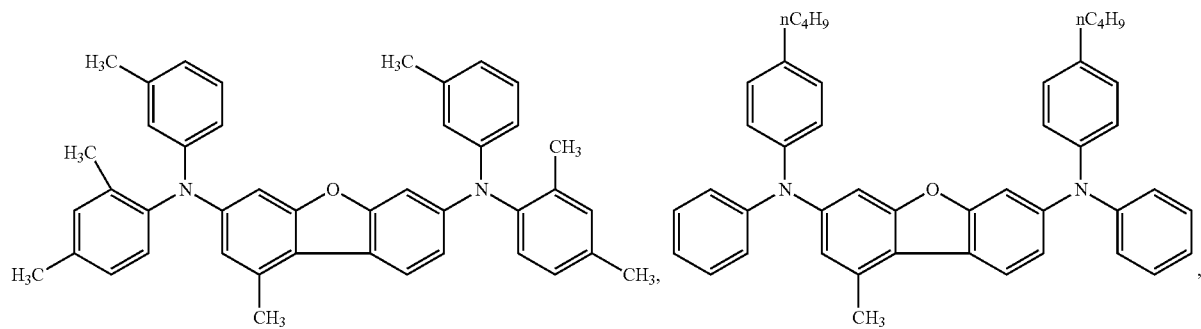
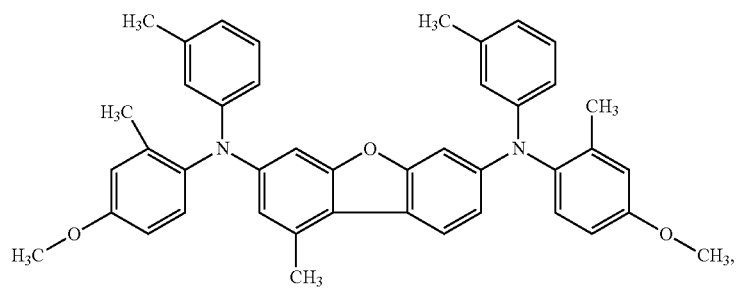
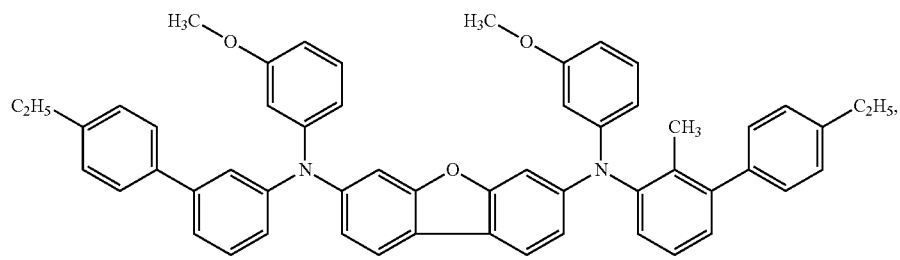

-continued

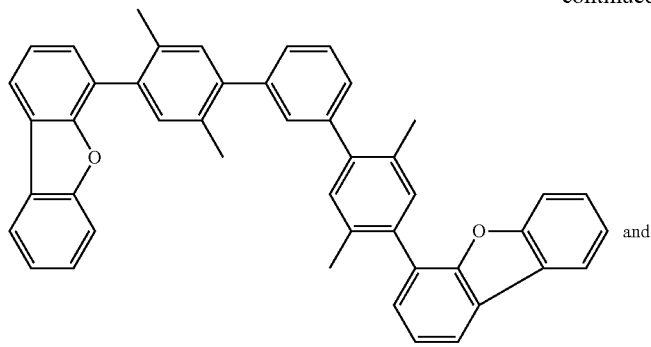
and

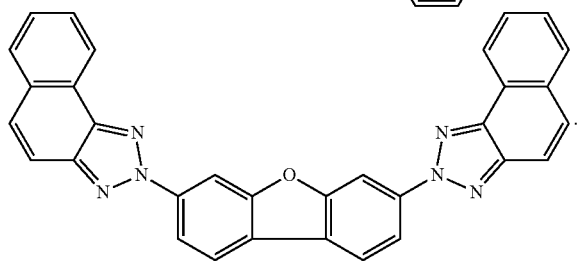

Preferably, the compound or compounds of the present invention emit light below about 520 nm, in particular between about 380 nm and about 520 nm.

The compound or compounds of the present invention have especially a NTSC coordinate of between about (0.12, 0.05) and about (0.16, 0.10), very especially a NTSC coordinate of about (0.14, 0.08).

The compound or compounds of the present invention have a melting point above about 150° C., preferably above about 200° C. and most preferred above about 250° C.

To obtain organic layers of this invention with the proper $T_g$, or glass transition temperature, it is advantageous that the present organic compounds have a glass transition temperature greater than about 100° C., for example greater than about 110° C., for example greater than about 120° C., for instance greater than about 130° C.

In one embodiment of the present invention compounds of formula I, or II are preferred, wherein at least one of the groups $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ is a $C_7$-$C_{30}$aryl group, especially a polycyclic $C_8$-$C_{30}$aryl group. Compounds of formula I, or II are even more preferred, wherein at least two of the groups $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are a $C_7$-$C_{30}$aryl group, especially a polycyclic $C_8$-$C_{30}$aryl group.

In a further embodiment of the present invention compounds of formula are preferred, wherein M is a single bond, —CO—, —COO—, —S—, —SO—, —SO$_2$—, —O—,

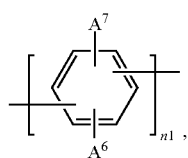

especially

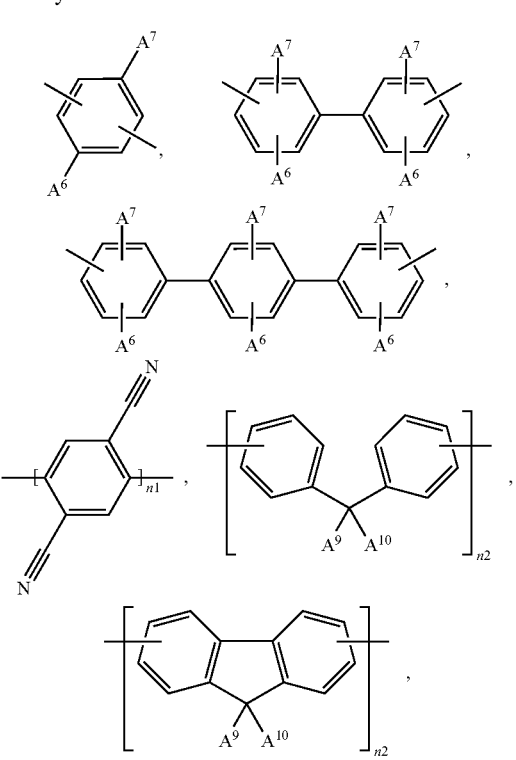

especially

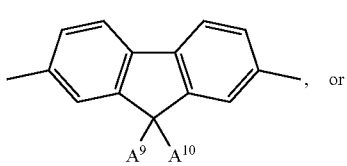, or

-continued
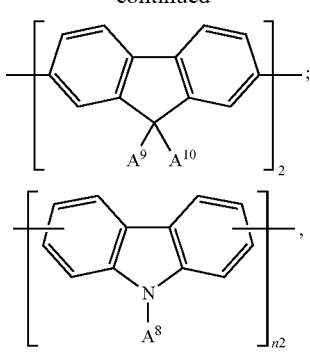
especially
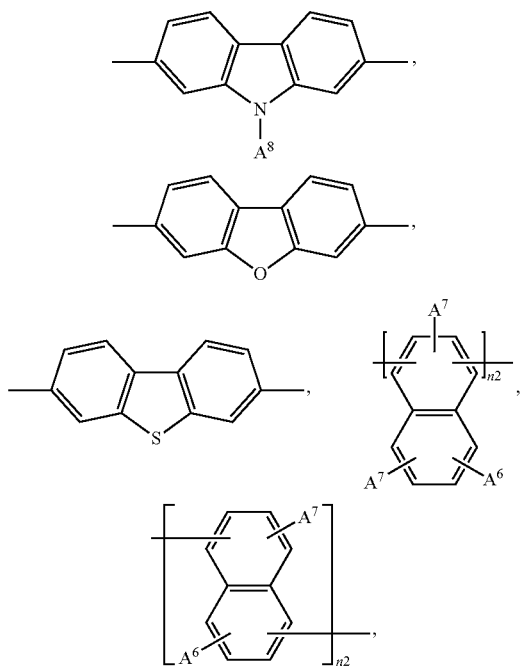
especially
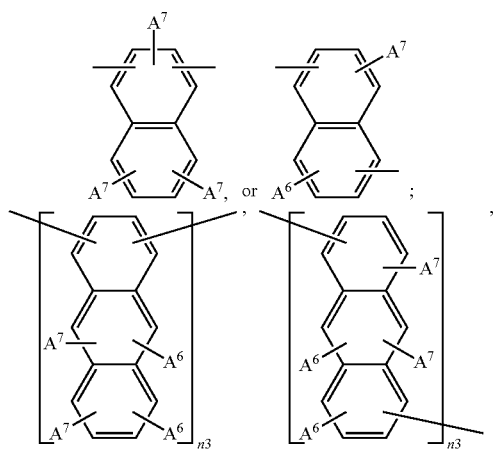
-continued
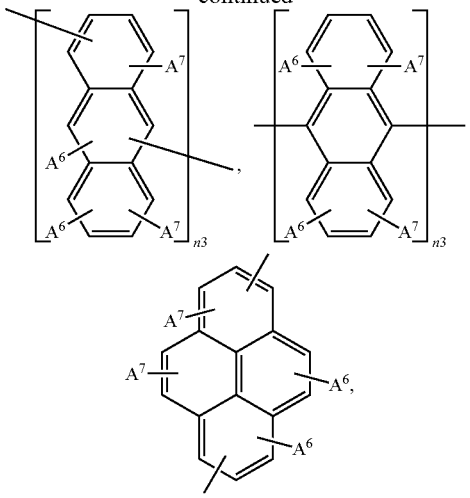
especially
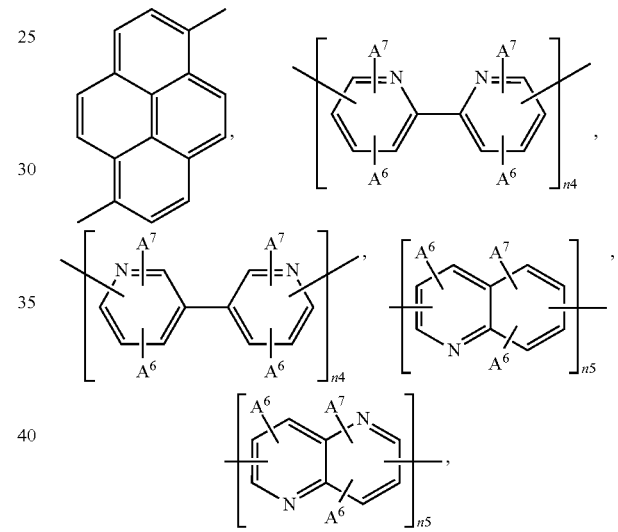
especially
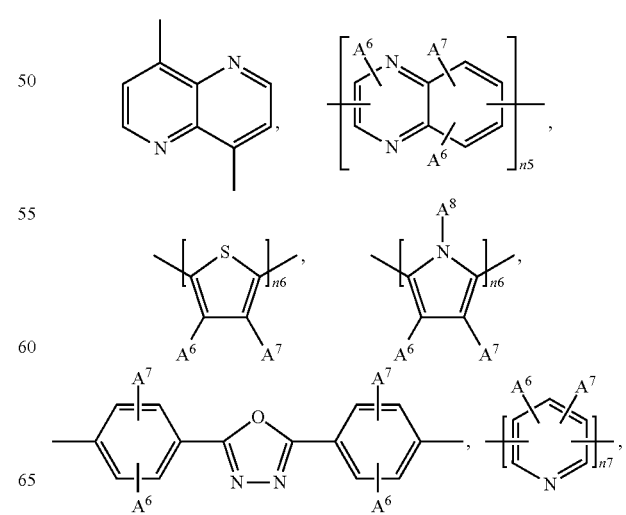

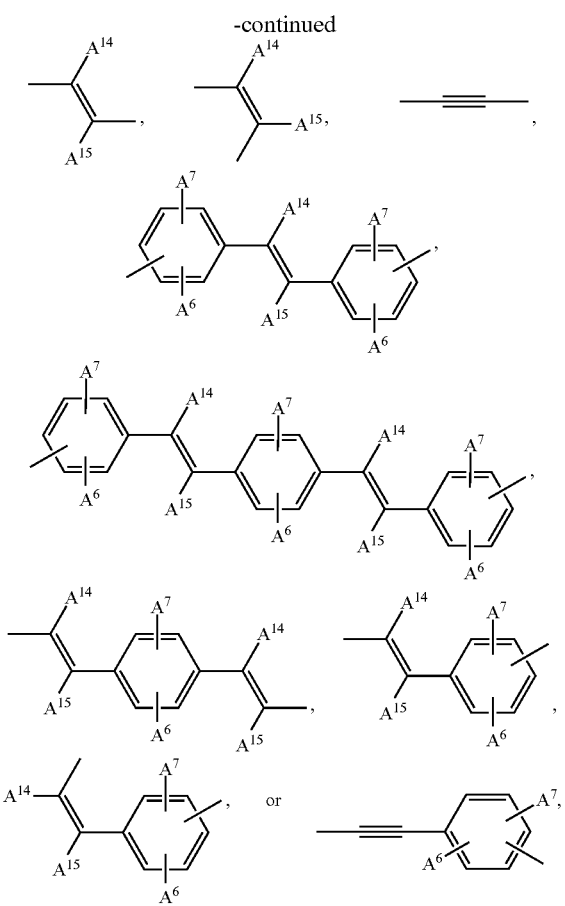

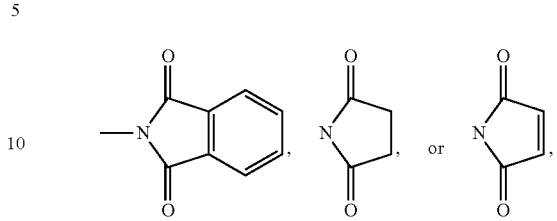

wherein n1, n2, n3, n4, n5, n6 and n7 are integers of 1 to 10, in particular 1 to 3, $A^6$ and $A^7$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, or —CO-$A^{28}$, $A^8$ is $C_1$-$C_{18}$alkyl, $C_1$-$C_{18}$alkyl which is substituted by E' and/or interrupted by D', $C_6$-$C_{24}$aryl, or $C_7$-$C_{25}$aralkyl, $A^9$ and $A^{10}$ are independently of each other $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', or $C_7$-$C_{25}$aralkyl, or $A^9$ and $A^{10}$ form a ring, especially a five- or six-membered ring, which can optionally be substituted by one or more $C_1$-$C_{18}$ alkyl groups;

$A^{14}$ and $A^{15}$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, or $C_2$-$C_{20}$heteroaryl which is substituted by G', D' is —CO—; —COO—; —S—; —SO—; —SO$_2$—; —O—; —N$A^{25}$-; —Si$A^{30}A^{31}$-; —PO$A^{32}$-; —C$A^{23}$=C$A^{24}$-; or —C≡C—; and E' is —O$A^{29}$; —S$A^{29}$; —N$A^{25}A^{26}$; —CO$A^{28}$; —COO$A^{27}$; —CON$A^{25}A^{26}$; —CN; —OCOO$A^{27}$; or halogen; G' is E', or $C_1$-$C_{18}$alkyl; wherein $A^{23}$, $A^{24}$, $A^{25}$ and $A^{26}$ are independently of each other H;

$C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $A^{25}$ and $A^{26}$ together form a five or six membered ring, in particular $A^{27}$ and $A^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—, $A^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $A^{30}$ and $A^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $A^{32}$ is $C_1$-$C_{18}$alkyl, $C_6$-$C_{18}$aryl, or $C_6$-$C_{18}$aryl, which is substituted by $C_1$-$C_{18}$alkyl.

Preferably, $A^6$ and $A^7$ are independently of each other H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{18}$alkyl which is substituted by E' and/or interrupted by D', such as —CH$_2$OCH$_3$, —CH$_2$OCH$_2$CH$_3$, —CH$_2$OCH$_2$CH$_2$OCH$_3$, or —CH$_2$OCH$_2$CH$_2$OCH$_2$CH$_3$, $C_6$-$C_{24}$aryl, such as phenyl, naphthyl, or biphenyl, $C_6$-$C_{24}$aryl which is substituted by G', such as —C$_6$H$_4$OCH$_3$, —C$_6$H$_4$OCH$_2$CH$_3$, —C$_6$H$_3$(OCH$_3$)$_2$, or —C$_6$H$_3$(OCH$_2$CH$_3$)$_2$, —C$_6$H$_4$CH$_3$, —C$_6$H$_3$(CH$_3$)$_2$, —C$_6$H$_2$(CH$_3$)$_3$, or —C$_6$H$_4$tBu.

$A^8$ is preferably H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, n-heptyl, or $C_6$-$C_{24}$aryl, such as phenyl, naphthyl, or biphenyl.

Preferably, $A^9$ and $A^{10}$ are independently of each other H, $C_1$-$C_{18}$alkyl, such as n-butyl, sec-butyl, hexyl, octyl, or 2-ethyl-hexyl, $C_1$-$C_{18}$alkyl which is substituted by E' and/or interrupted by D', such as —CH$_2$(OCH$_2$CH$_2$)$_w$OCH$_3$, w=1, 2, 3, or 4, $C_6$-$C_{24}$aryl, such as phenyl, naphthyl, or biphenyl, $C_6$-$C_{24}$aryl which is substituted by G', such as —C$_6$H$_4$OCH$_3$, —C$_6$H$_4$OCH$_2$CH$_3$, —C$_6$H$_3$(OCH$_3$)$_2$, —C$_6$H$_3$(OCH$_2$CH$_3$)$_2$, —C$_6$H$_4$CH$_3$, —C$_6$H$_3$(CH$_3$)$_2$, —C$_6$H$_2$(CH$_3$)$_3$, or —C$_6$H$_4$tBu, or $A^9$ and $A^{10}$ together form a 4 to 8 membered ring, especially a 5 or 6 membered ring, such as cyclohexyl, or cyclopentyl.

Preferably, $A^{14}$ and $A^{15}$ are independently of each other H, $C_1$-$C_{18}$alkyl, such as as methyl, ethyl, n-propyl, iso-propyl, n-butyl, isobutyl, or sec-butyl, or $C_6$-$C_{24}$aryl, such as phenyl, naphthyl, or biphenyl.

D' is preferably —CO—, —COO—, —S—, —SO—, —SO$_2$—, —O—, —N$A^{25}$-, wherein $A^{25}$ is $C_1$-$C_{18}$alkyl, such as methyl, ethyl, n-propyl, iso-propyl, n-butyl, isobutyl, or sec-butyl, or $C_6$-$C_{24}$aryl, such as phenyl, naphthyl, or biphenyl.

E' is preferably —O$A^{29}$; —S$A^{29}$; —N$A^{25}A^{25}$; —CO$A^{28}$; —COO$A^{27}$; —CON$A^{25}A^{25}$; or —CN; wherein $A^{25}$, $A^{27}$, $A^{28}$ and $A^{29}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{24}$ aryl, such as phenyl, naphthyl, or biphenyl.

Among the above-mentioned groups M the following groups are preferred:
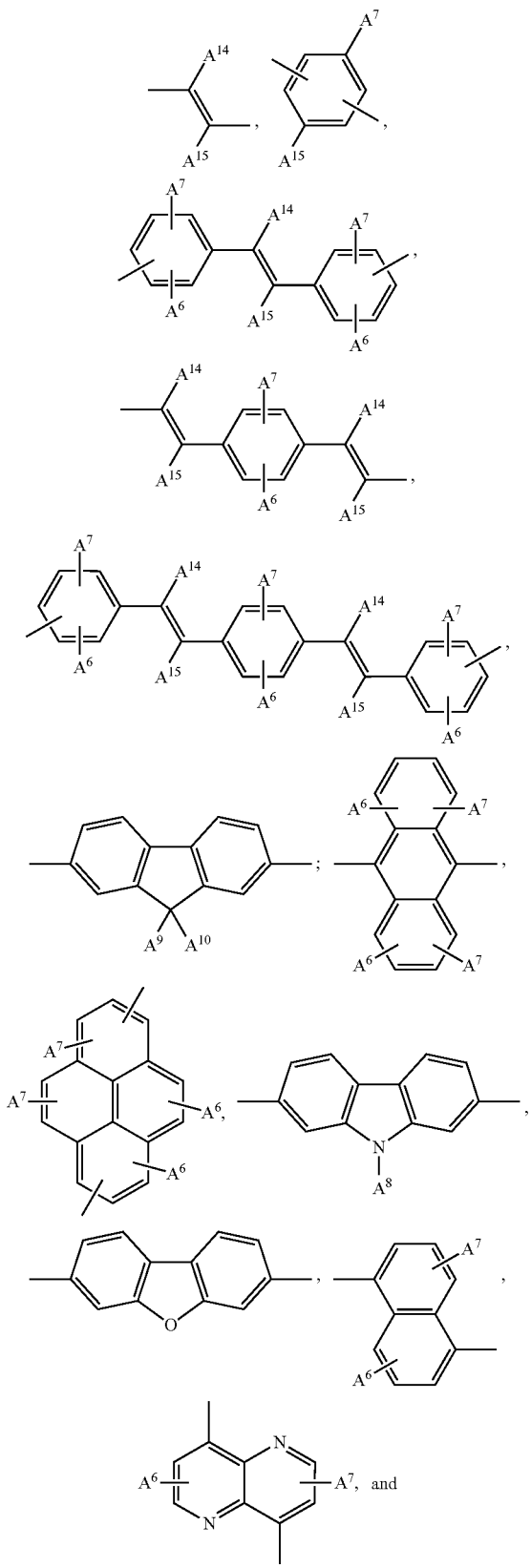
-continued
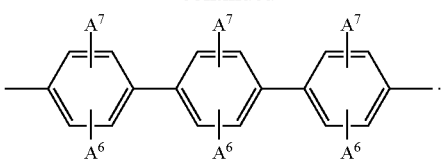
Examples of especially preferred groups M are:
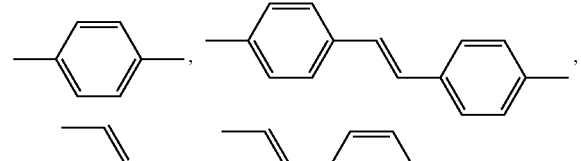
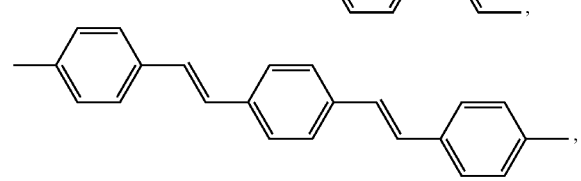
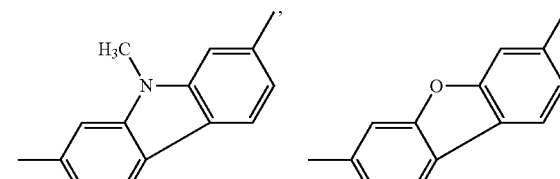
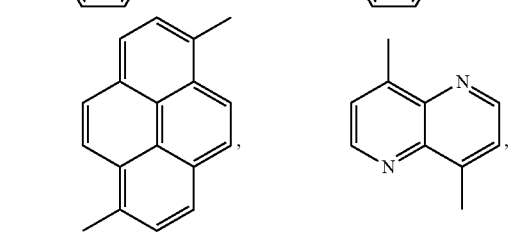
wherein $A^8$ and $A^9$ are independently of each other $C_1$-$C_{18}$alkyl, or cyclohexan;
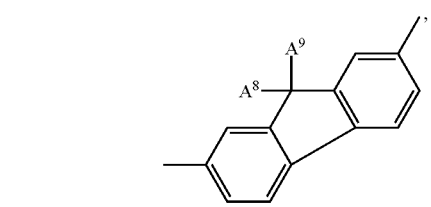

wherein $A^6$ and $A^7$ are independently of each other H, or $C_1$-$C_{18}$alkyl; or

Groups M having a polycyclic $C_8$-$C_{30}$arylen group, or a polycyclic $C_4$-$C_{26}$heteroarylen group, wherein polycyclic ring system comprises at least 8 atoms, are preferred,

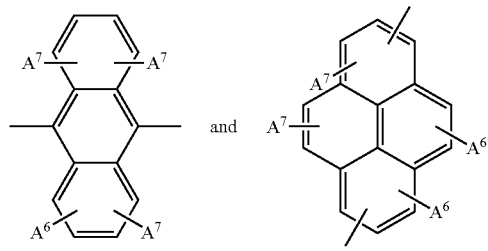

are most preferred.

Among the compounds of formula II compounds of formula (IIa)

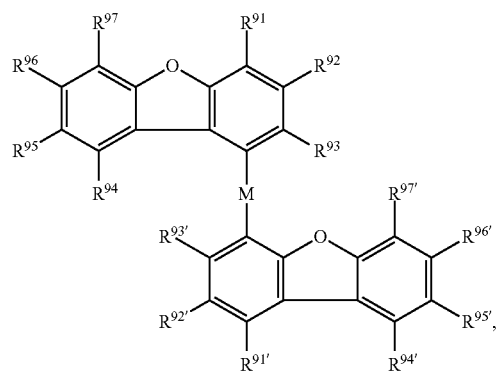

(IIb)

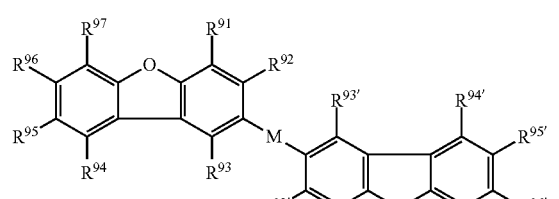

(IIc)

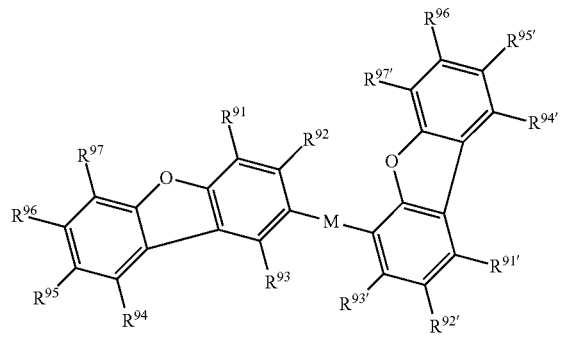

are preferred.

Compounds of formula

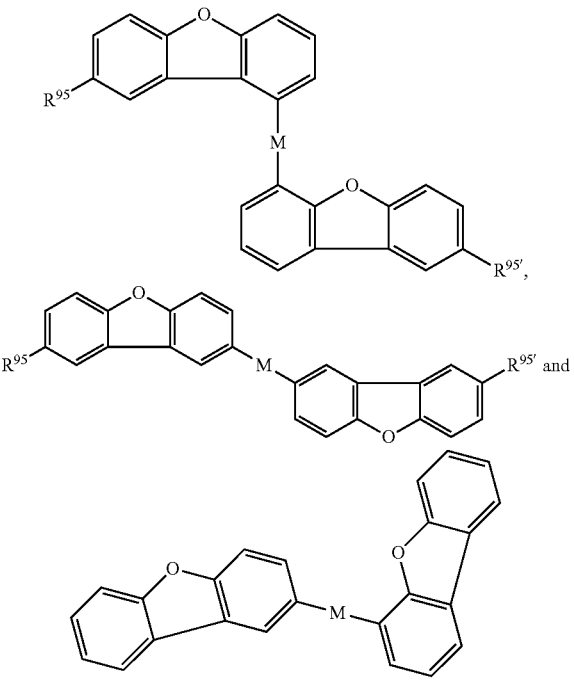

are even more preferred, wherein $R^{95}$ and $R^{95'}$ are independently of each other $C_1$-$C_{24}$alkyl, or $C_8$-$C_{14}$aryl, especially phenyl, naphthyl, phenanthryl, anthranyl, or pyrenyl, which may be substituted by one, or more $C_1$-$C_8$alkyl, or $C_1$-$C_8$alkoxy groups, such as a group of formula

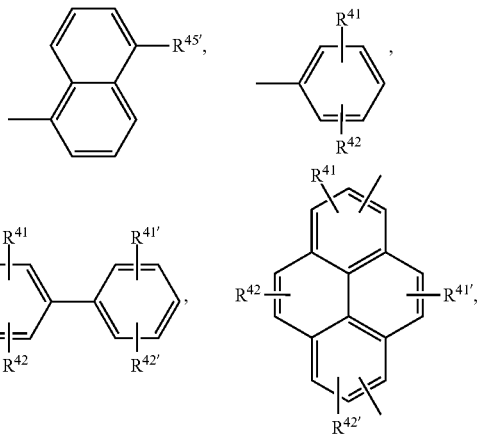

especially wherein
R$^{41}$, R$^{41'}$, R$^{42}$ and R$^{42'}$ are independently of each other is hydrogen, C$_1$-C$_8$alkyl, or C$_1$-C$_8$alkoxy, R$^{45'}$ is hydrogen, phenyl, or 1-naphthyl, which can be substituted by one, or more C$_1$-C$_8$alkyl, or C$_1$-C$_8$alkoxy groups; or C$_1$-C$_8$alkyl, or C$_1$-C$_8$alkoxy.

In another embodiment compounds of formula IIb are preferred, wherein M is a single bond, R$^{96}$ and R$^{96'}$ are a group

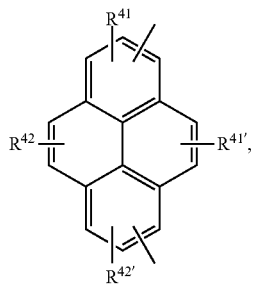

especially

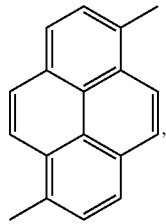 [SMILES: Cc1ccc2ccc3c(C)ccc4ccc1c2c43]

and R$^{91}$, R$^{92}$, R$^{93}$, R$^{94}$, R$^{95}$, R$^{96}$, R$^{97}$, R$^{91'}$, R$^{92'}$, R$^{93'}$, R$^{94'}$, R$^{95'}$, R$^{96'}$ and R$^{97'}$ are hydrogen.

Examples of especially preferred compounds are:

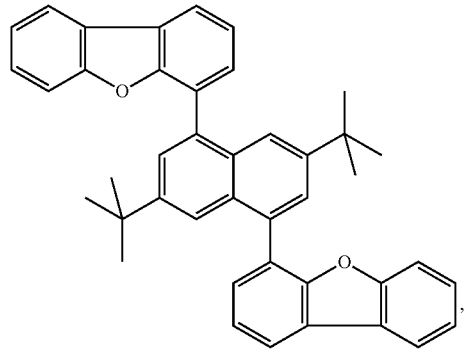
(B-1)

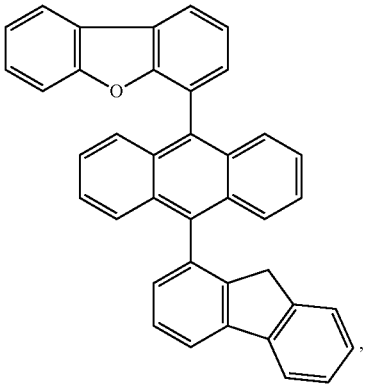
(B-2)

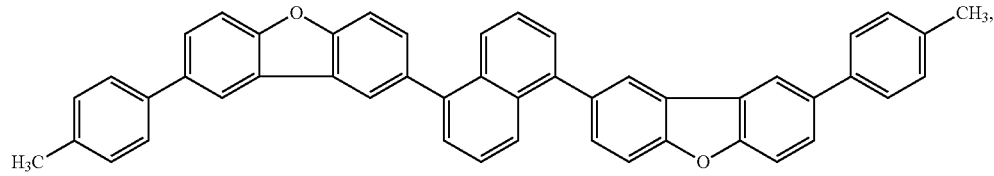
(B-3)

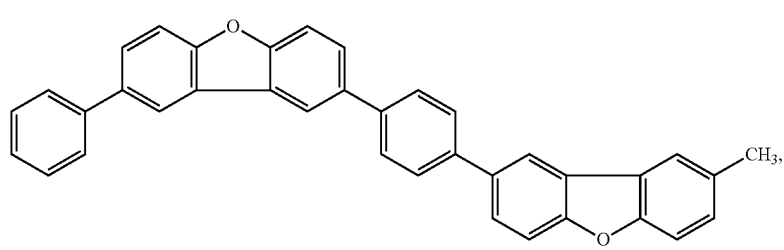
(B-4)

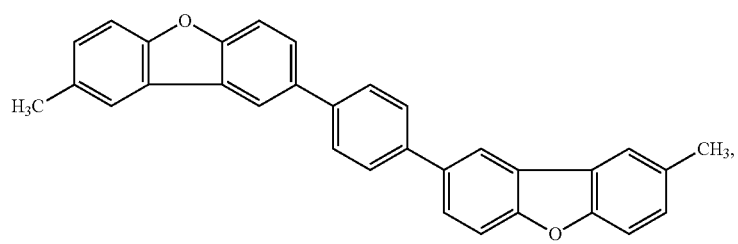
(B-5)

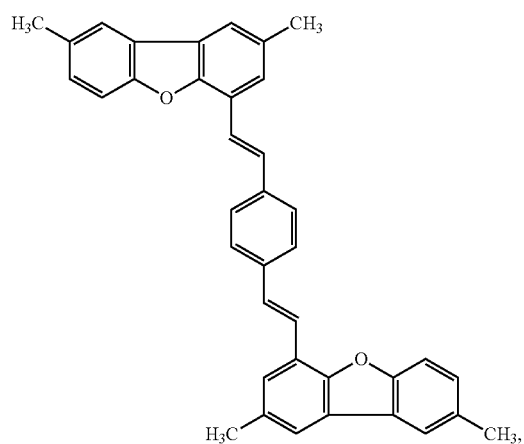
(B-6)
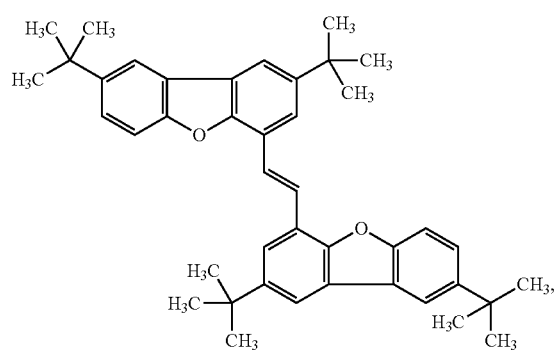
(B-7)
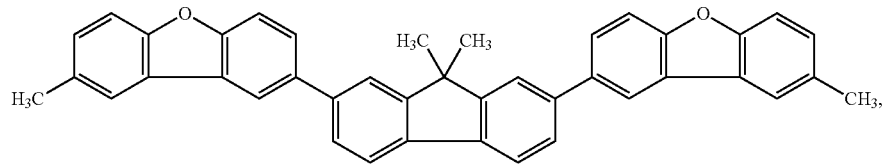
(B-8)
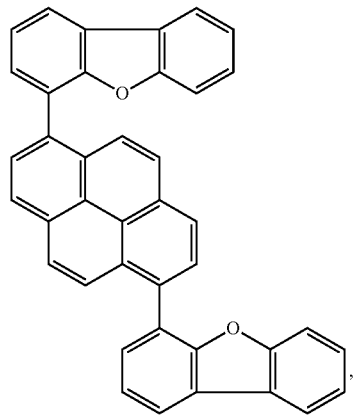
(B-9)
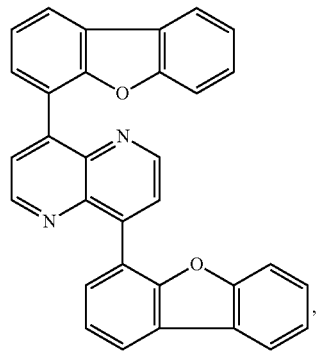
(B-10)
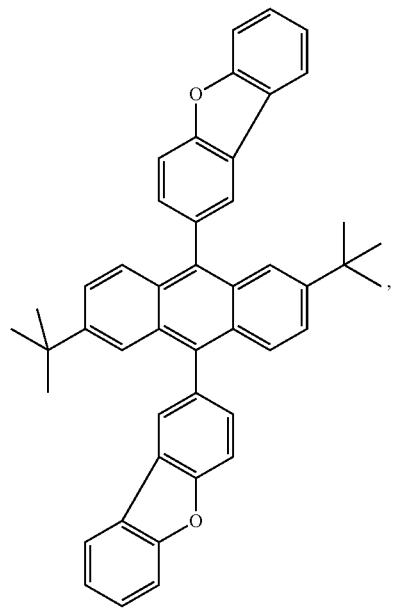
(B-11)
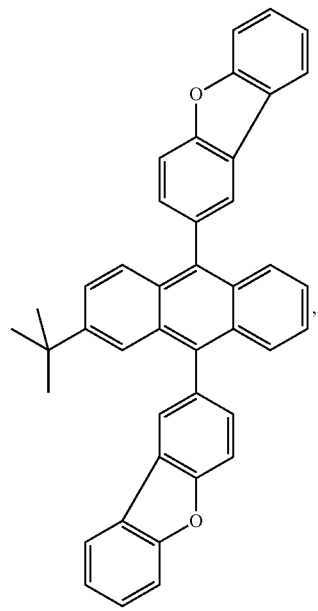
(B-12)

(B-13)
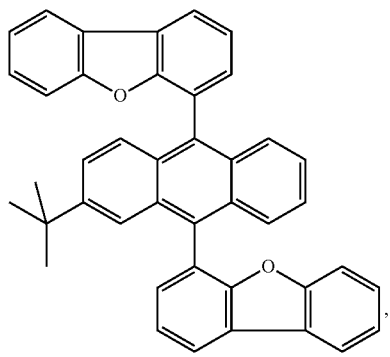
(B-14)
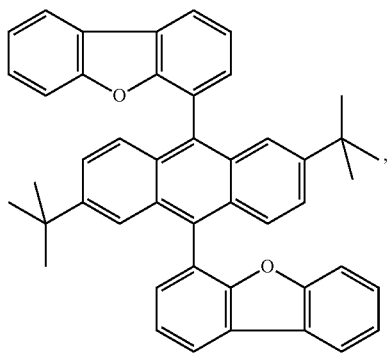
(B-15)
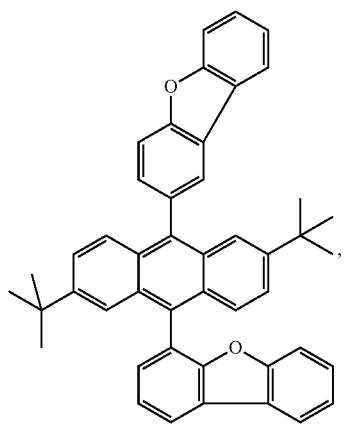
(B-16)
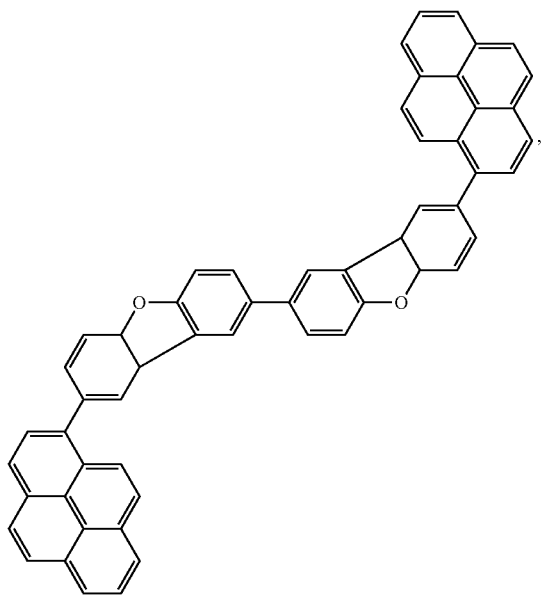
(B-17)
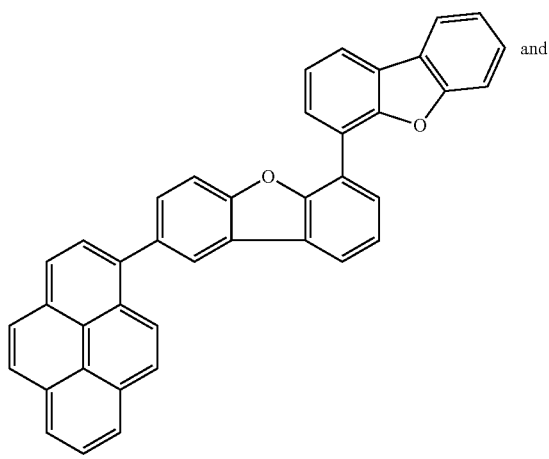
and
(B-18)
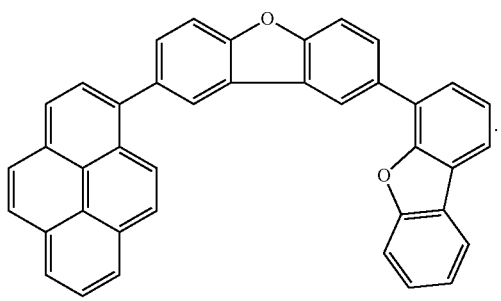

In further preferred embodiment of the present invention at least one, preferably two of the groups $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are a group

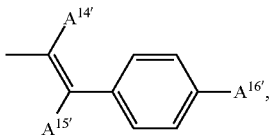

wherein $A^{14'}$ and $A^{15'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, and $A^{16'}$ is H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G; or a polycyclic aryl group, especially pentalenyl, indenyl, azulenyl, naphthyl, biphenylenyl, as-indacenyl, s-indacenyl, acenaphthylenyl, fluorenyl, phenanthryl, anthracenyl, fluoranthenyl, acephenanthrylenyl, aceanthrylenyl, triphenylenyl, pyrenyl, chrysenyl, naphthacenyl, picenyl, perylenyl, pentacenyl, pentaphenyl, hexacenyl, or hexaphenyl, which can optionally be substituted by G, wherein D, E and G are as defined above. Examples of particularly preferred groups are:

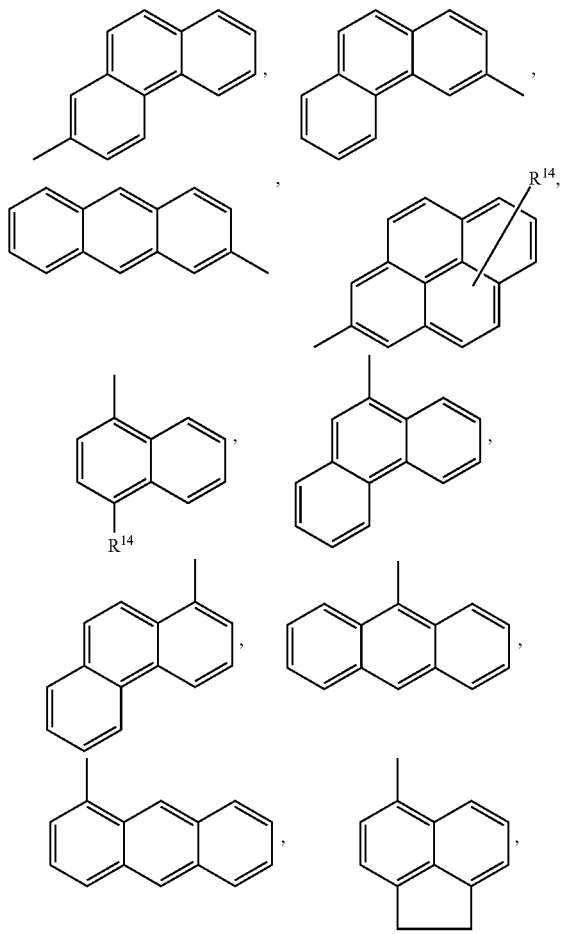

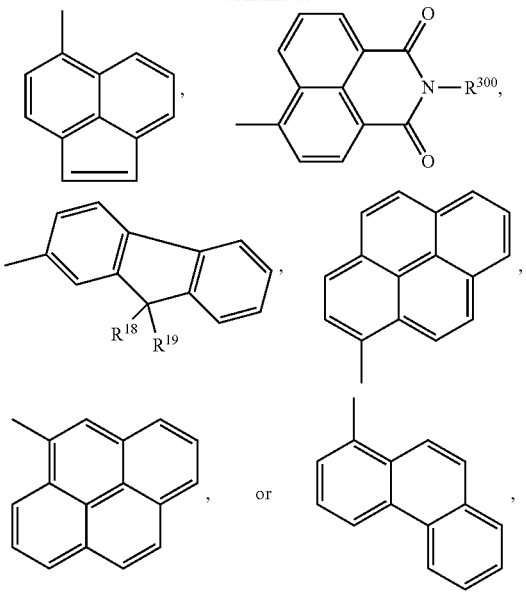

wherein $R^{300}$ is $C_1$-$C_8$alkyl, phenyl, which can be substituted by one, or more $C_1$-$C_8$alkyl, or $C_1$-$C_8$alkoxy groups, $R^{14}$ is hydrogen, $C_1$-$C_8$alkyl, phenyl, or 1-naphthyl, which can be substituted by one, or more $C_1$-$C_8$alkyl, or $C_1$-$C_8$alkoxy groups; or $C_1$-$C_8$alkoxy, and $R^{18}$ and $R^{19}$ are independently of each other $C_1$-$C_8$alkyl, or cyclohexan.

Compounds of formula Ia, Ib and Ic are preferred, wherein $R^{82}$, $R^{87}$, $R^{83}$, $R^{86}$, $R^{83'}$ and $R^{86'}$ are independently of each other one of the above groups. $R^{82}$ and $R^{87}$, $R^{83}$ and $R^{86}$, $R^{83'}$ and $R^{86'}$ can be the same or different.

In a further preferred embodiment of the present invention at least one, especially two of the groups $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are independently of each other a group the formula —$(W^1)_a$—$(W^2)_b$—$W^3(Y^1)$, wherein a and b are 0, or 1, $W^1$ and $W^2$ are independently of each other a group of formula

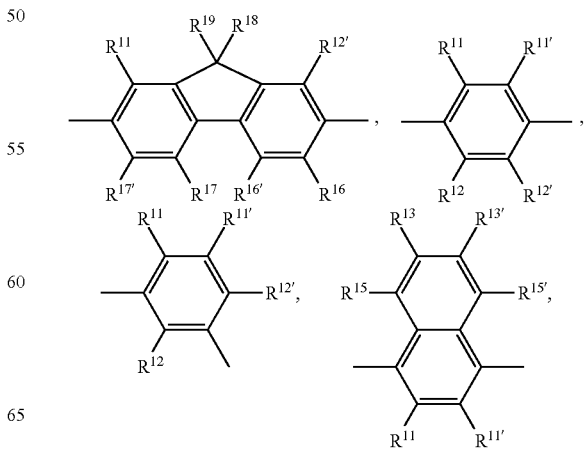

31

-continued

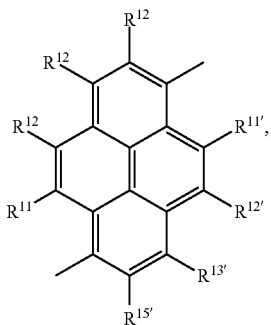

especially

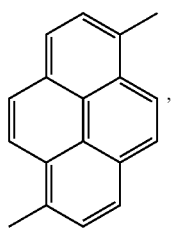

and
$W^3$ is a group of formula

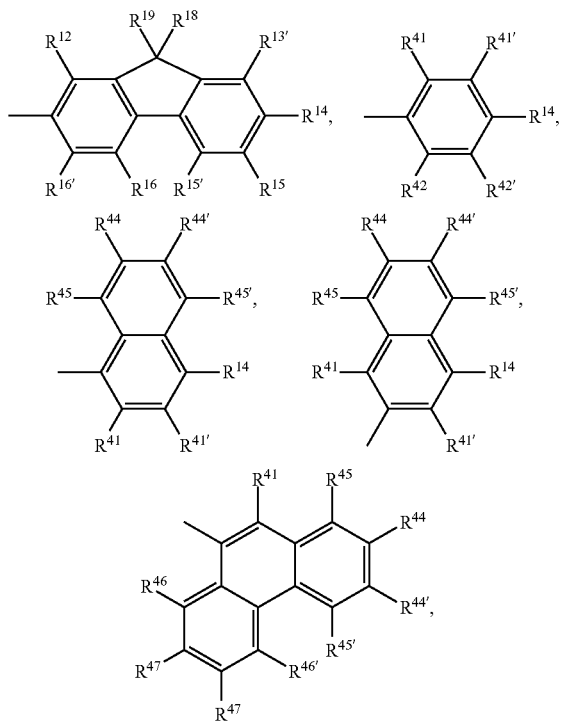

32

-continued

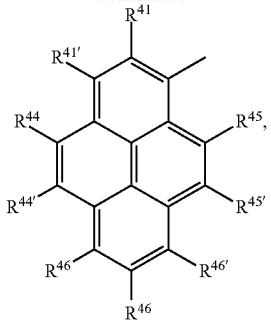

especially

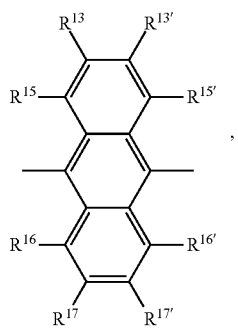

wherein
$R^{11}, R^{11'}, R^{12}, R^{12'}, R^{13}, R^{13'}, R^{15}, R^{15'}, R^{16}, R^{16'}, R^{17}, R^{17'}, R^{41}, R^{41'}, R^{42}, R^{42'}, R^{44}, R^{44'}, R^{45}, R^{45'}, R^{46}, R^{46'}, R^{47}$ and $R^{47'}$ are independently of each other H, E, silyl, such as tri($C_1$-$C_8$alkyl)silyl, $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_1$-$C_{18}$alkoxy; or $C_1$-$C_{18}$alkoxy which is substituted by E and/or interrupted by D; $C_7$-$C_{18}$aralkyl; or $C_7$-$C_{18}$aralkyl which is substituted by G;
$R^{14}$ is H, silyl, such as tri($C_1$-$C_8$alkyl)silyl, $C_1$-$C_{18}$alkyl; or $C_1$-$C_{18}$alkyl which is substituted by E and/or interrupted by D; $C_1$-$C_{18}$alkoxy; or $C_1$-$C_{18}$alkoxy which is substituted by E and/or interrupted by D;

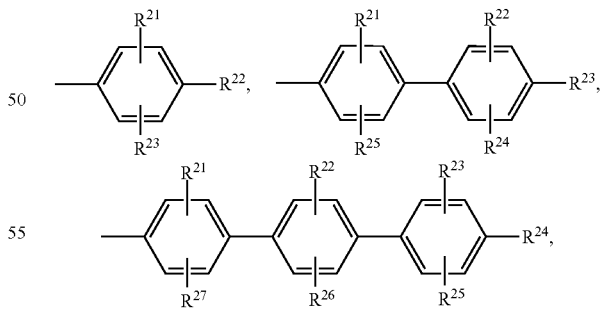

$R^{18}$ and $R^{19}$ are independently of each other $C_1$-$C_{18}$alkyl; $C_1$-$C_{18}$alkoxy, $C_6$-$C_{18}$aryl; $C_7$-$C_{18}$aralkyl; or $R^{18}$ and $R^{19}$ together form a ring especially a five- or six-membered ring, which can optionally be substituted by $C_1$-$C_8$alkyl,
$R^{21}, R^{22}, R^{23}, R^{24}, R^{25}, R^{26}$ and $R^{27}$ are independently of each other H, E, $C_1$-$C_{18}$alkyl; $C_1$-$C_{18}$alkyl which is substituted by E and/or interrupted by D; $C_7$-$C_{18}$aralkyl; $C_7$-$C_{18}$aralkyl which is substituted by G; or W³ is a group of formula

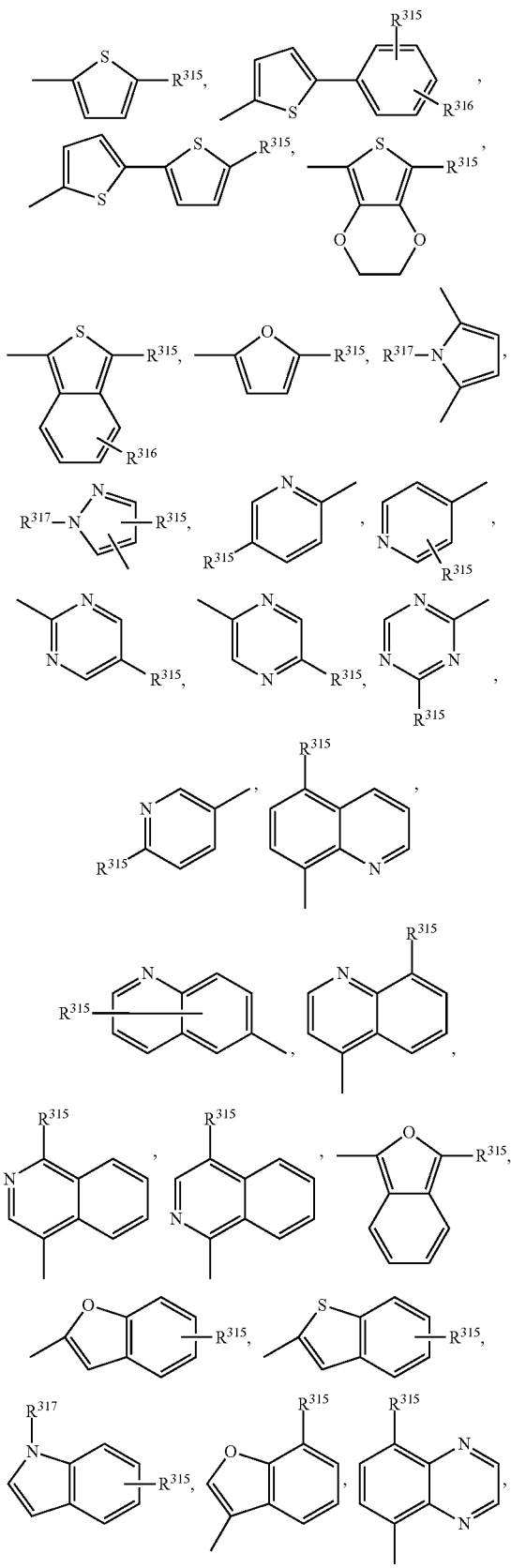

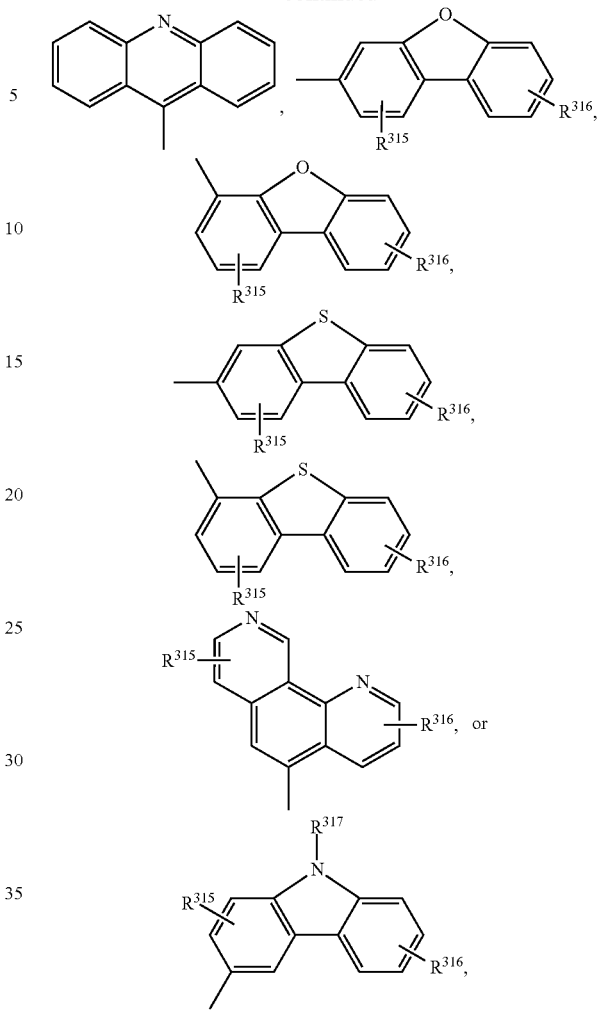

wherein R³¹⁵ and R³¹⁶ are independently of each other a hydrogen atom, a $C_1$-$C_{18}$alkyl group, a $C_1$-$C_{18}$alkoxy group, a group of formula

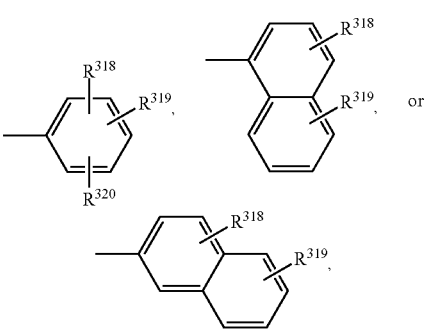

wherein R³¹⁸, R³¹⁹ and R³²⁰ independently from each other stand for hydrogen, $C_1$-$C_8$-alkyl, $C_1$-$C_8$-alkoxy, or phenyl, and R³¹⁷ stands for is a hydrogen atom, a $C_1$-$C_{25}$alkyl group, which might be interrupted by —O—, a cycloalkyl group, a $C_7$-$C_{18}$aralkyl group, a $C_6$-$C_{18}$aryl group, or a heterocyclic group, which may be substituted by G; wherein D is —CO—, —COO—, —OCOO—, —S—, —SO—, —SO$_2$—, —O—, —NR$^5$—, SiR$^{61}$R$^{62}$—, —POR$^5$—, —CR$^{63}$=CR$^{64}$—, or —C≡C—;

E is —OR$^5$, —SR$^5$, —NR$^5$R$^6$, —COR$^8$, —COOR$^7$, —OCOOR$^7$, —CONR$^5$R$^6$, —CN, or halogen;

G is E, or C$_1$-C$_{18}$alkyl; wherein R$^5$ and R$^6$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl, or C$_1$-C$_{18}$alkyl which is interrupted by —O—; or R$^5$ and R$^6$ together form a five or six membered ring, in particular

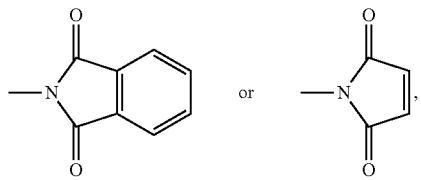

R$^7$ is C$_7$-C$_{12}$alkylaryl; C$_1$-C$_{18}$alkyl; or C$_1$-C$_{18}$alkyl which is interrupted by —O—;

R$^8$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; C$_7$-C$_{12}$alkylaryl, or C$_1$-C$_{18}$alkyl which is interrupted by —O—;

R$^{61}$ and R$^{62}$ are independently of each other C$_6$-C$_{18}$aryl; C$_6$-C$_{18}$aryl which is substituted by C$_1$-C$_{18}$alkyl, or C$_1$-C$_{18}$alkoxy; or C$_1$-C$_{18}$alkyl which is interrupted by —O—, and R$^{63}$ and R$^{64}$ are independently of each other H, C$_6$-C$_{18}$aryl; C$_6$-C$_{18}$aryl which is substituted by C$_1$-C$_{18}$alkyl, C$_1$-C$_{18}$alkoxy; or C$_1$-C$_{18}$alkyl which is interrupted by —O—.

If W$^3$ is derived from a heteroaromatic group, it is preferably a group of formula

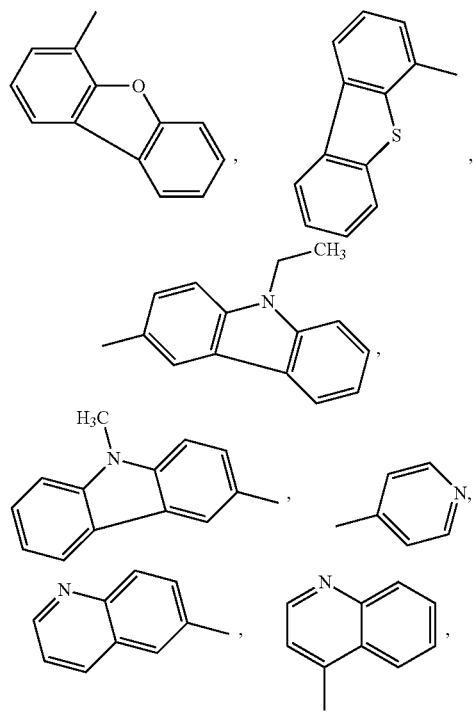

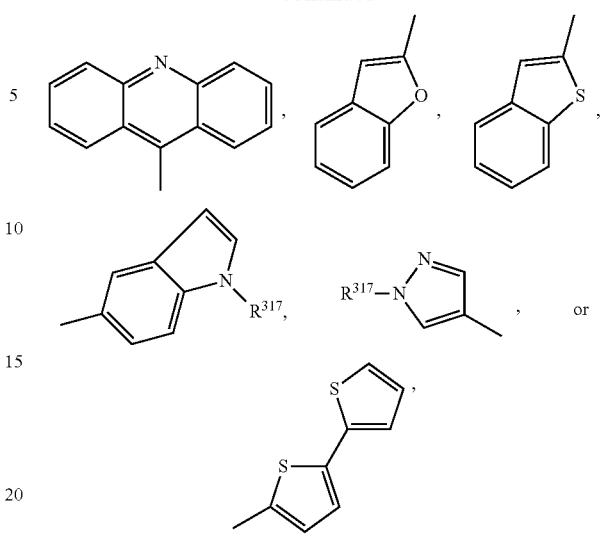

wherein R$^{317}$ is C$_1$-C$_{18}$alkyl.

Examples of preferred groups W$^1$ and W$^2$ are

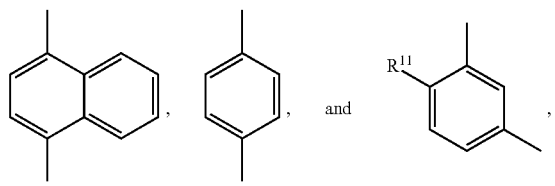

wherein R$^{11}$ is hydrogen, or C$_1$-C$_8$alkyl.

Examples of preferred groups W$^3$ are

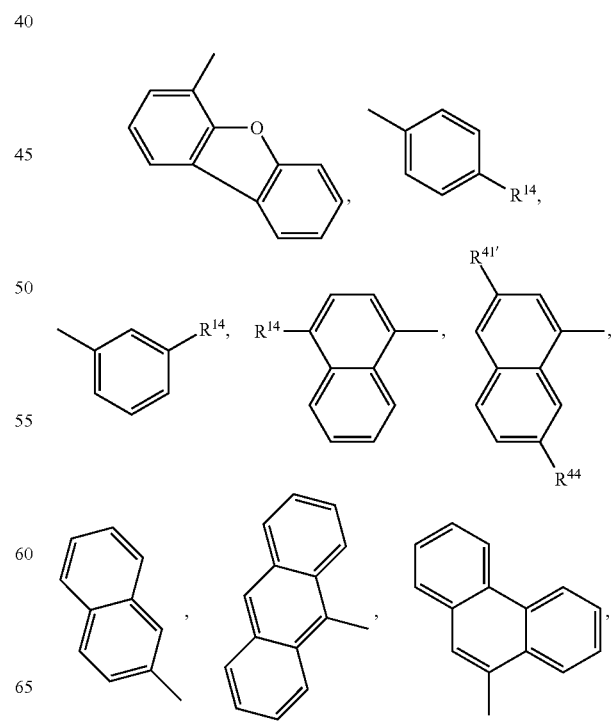

-continued

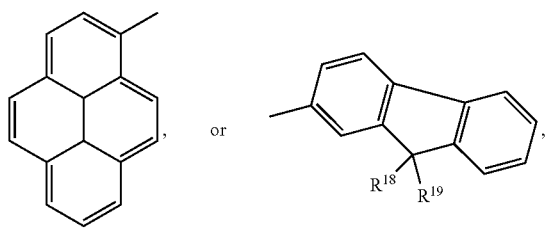

wherein $R^{14}$, $R^{41'}$ and $R^{44}$ are hydrogen, phenyl, tri($C_1$-$C_8$alkyl)silyl, or $C_1$-$C_8$alkyl, $R^{18}$ and $R^{19}$ are independently of each other $C_1$-$C_8$alkyl, or cyclohexan.

Examples of preferred groups —$(W^1)_a$—$(W^2)_b$—$W^3$ are

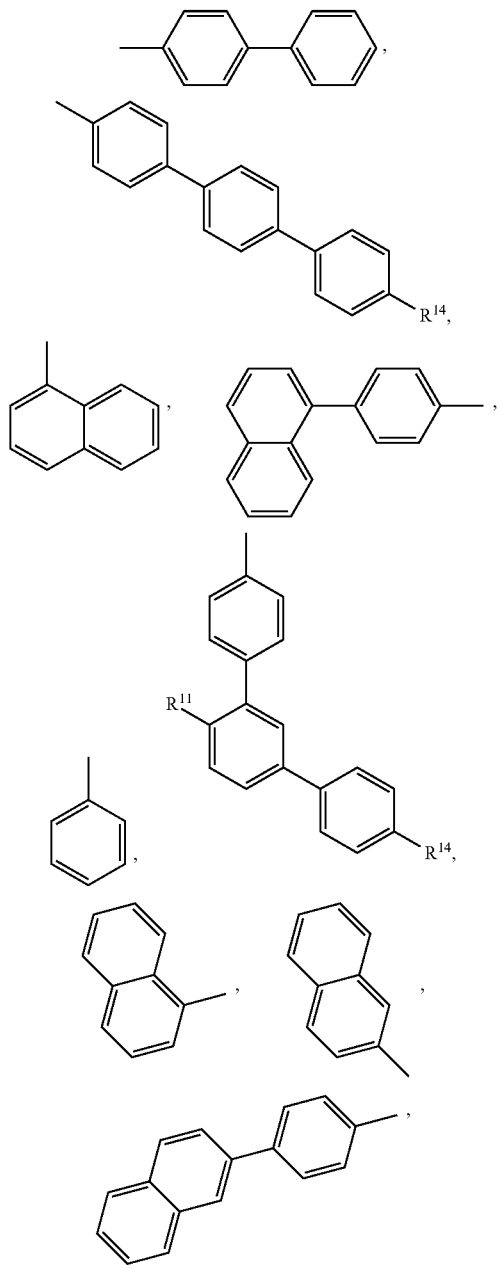

-continued

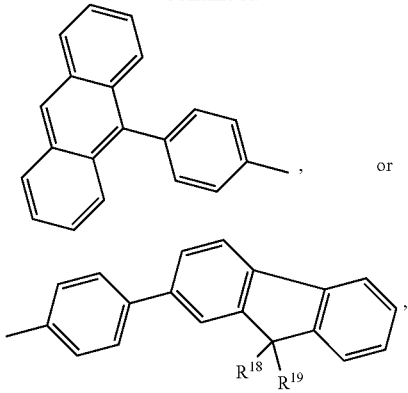

wherein $R^{11}$, $R^{14}$, $R^{18}$ and $R^{19}$ are independently of each other hydrogen, or $C_1$-$C_8$alkyl.

Among the compounds of formula I compounds of formula

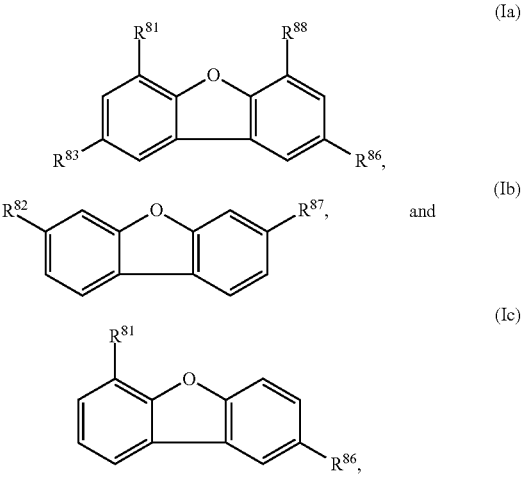

are more preferred, wherein $R^{82}$, $R^{83}$, $R^{86}$ and $R^{87}$ are independently of each other a group the formula —$(W^1)_a$—$(W^2)_b$—$W^3$. $R^{82}$, $R^{83}$, $R^{86}$ and $R^{87}$ can be different, but are preferably the same; and $R^{81}$ and $R^{88}$ are as defined above.

In a preferred embodiment of the present invention at least one, preferably two of the substituents $R^{82}$, $R^{83}$, $R^{86}$, $R^{87}$, $R^{81}$ and $R^{88}$ are

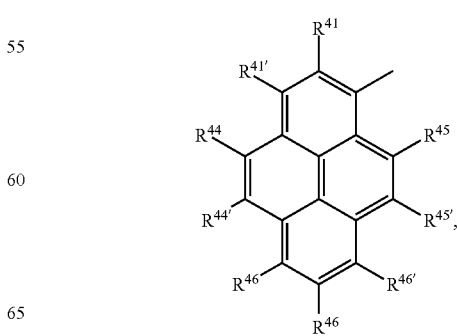

especially

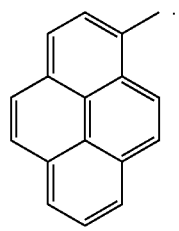

Compounds of formula Ia are even more preferred, wherein $R^{83}$ and $R^{86}$ are

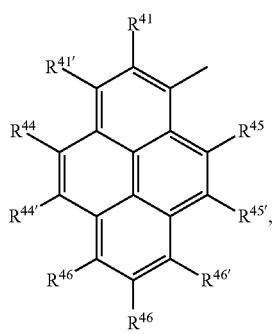

especially

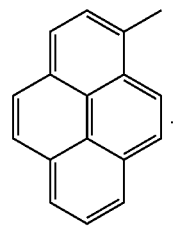 [SMILES: Cc1ccc2ccc3cccc4ccc1c2c34]

In a further preferred embodiment of the present invention compounds of formula

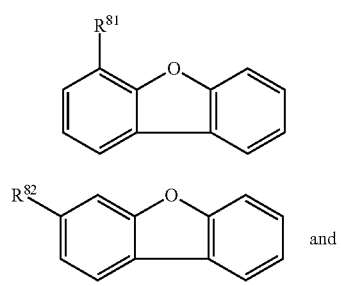
(Id)

and

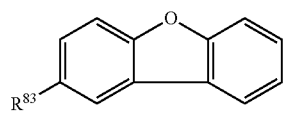
(Ie)

are preferred, wherein $R^{81}$, $R^{83}$ and $R^{83}$ a group the formula —($W^2$)—$W^3$, wherein $W^2$ is a group

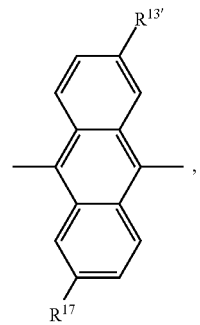

wherein $R^{13'}$ and $R^{17}$ are independently of each other $C_1$-$C_{18}$alkyl, or $C_1$-$C_{18}$alkoxy, $W^3$ is a group

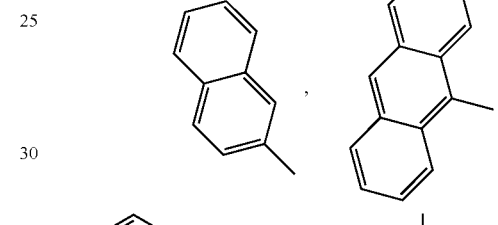

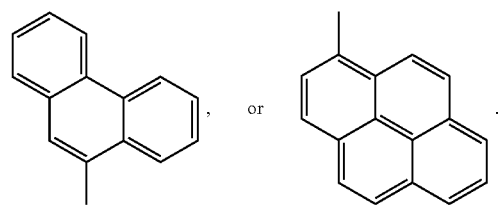

A further preferred embodiment of the present invention is directed to compounds of formula Ia and Ib, wherein at least $R^{82}$ and at least $R^{83}$ are a group of formula

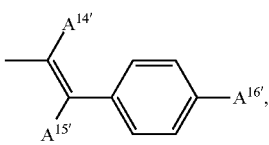

wherein $A^{14'}$ and $A^{15'}$ are independently of each other H, $C_1$-$C_{18}$alkyl, $C_6$-$C_{24}$aryl, or phenyl, which is substituted by one, or more $C_1$-$C_8$alkyl, or $C_1$-$C_8$alkoxy groups and the other, and $R^{87}$ and $R^{86}$ are a group of formula

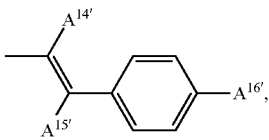

or a group of formula —($W^1$)$_a$—($W^2$)$_b$—$W^3$.

A further preferred embodiment of the present invention is directed to compounds of formula

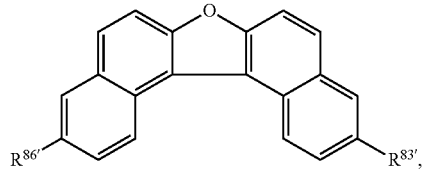
(Ic)

wherein $R^{83'}$ and $R^{86'}$ are independently of each other H, $C_1$-$C_{18}$alkyl,

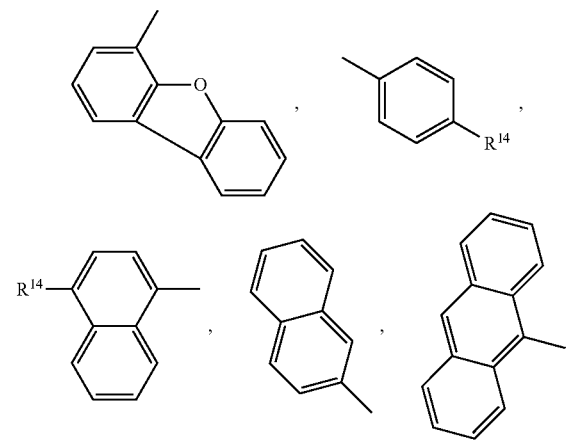

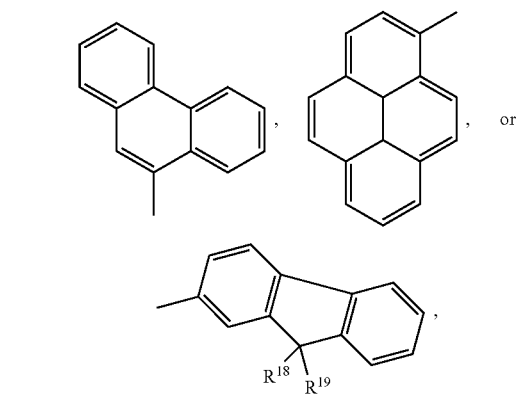

wherein $R^{14}$ is hydrogen, phenyl, tri($C_1$-$C_8$alkyl)silyl, or $C_1$-$C_8$alkyl, $R^{18}$ and $R^{19}$ are independently of each other $C_1$-$C_8$alkyl, or cyclohexan.

Examples of especially preferred compounds are given below:

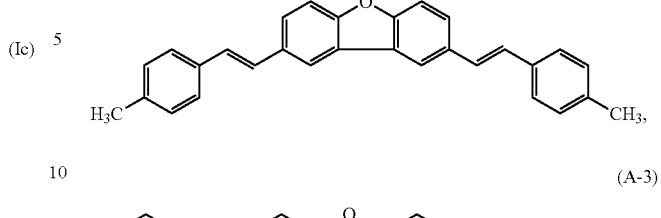
(A-1)

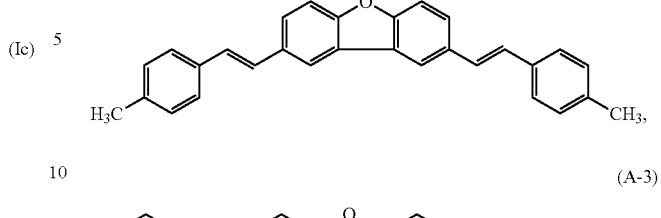
(A-2)

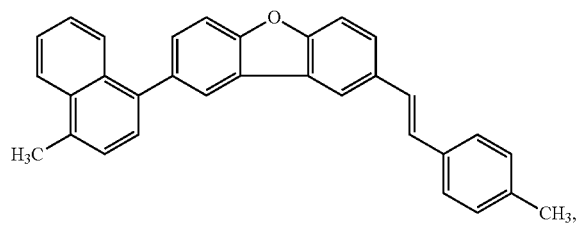
(A-3)

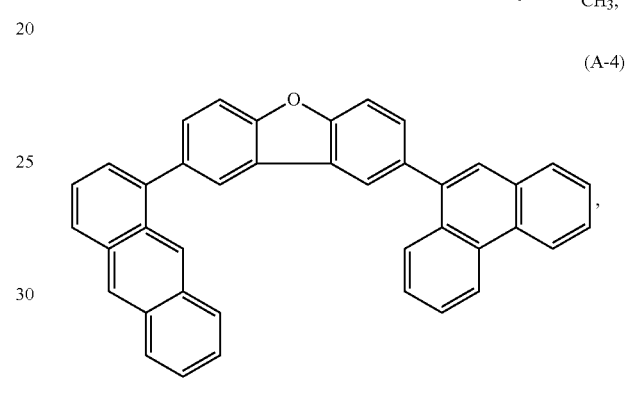
(A-4)

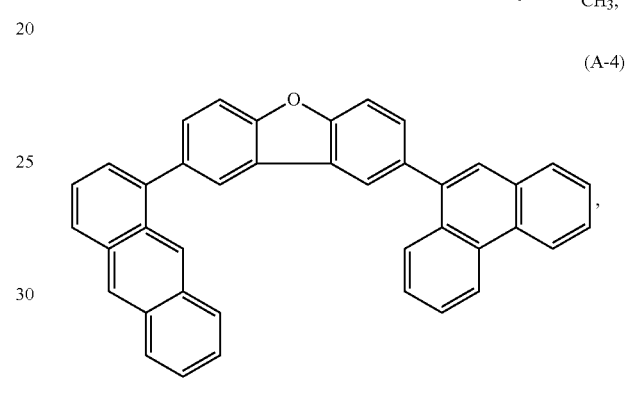
(A-5)

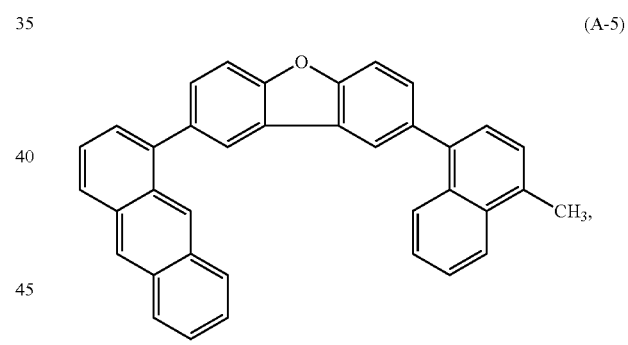
(A-6)

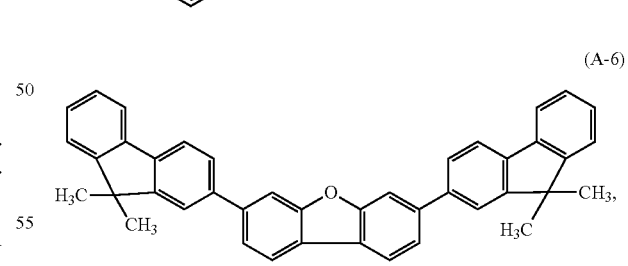
(A-7)

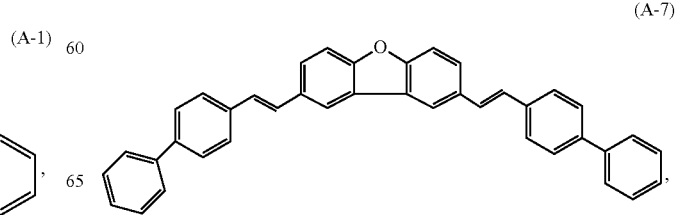

(A-8)
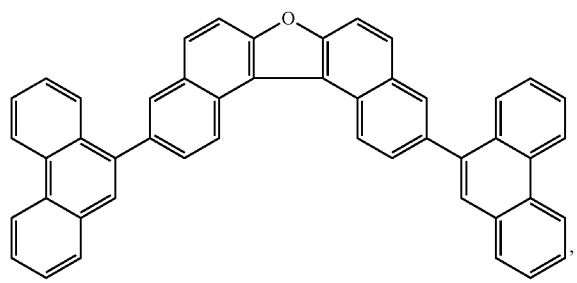
(A-9)
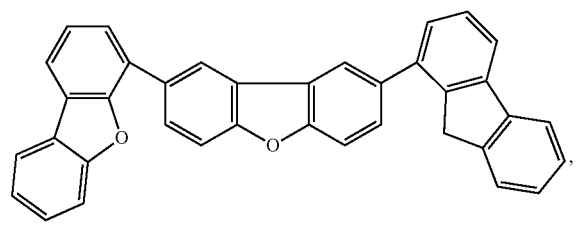
(A-10)
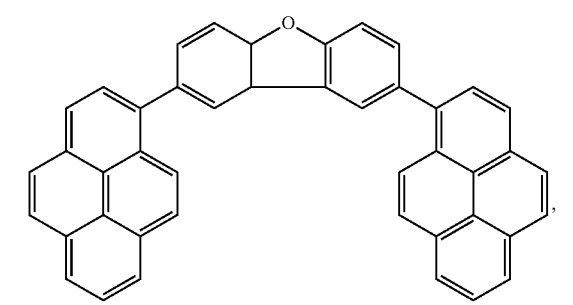
(A-11)
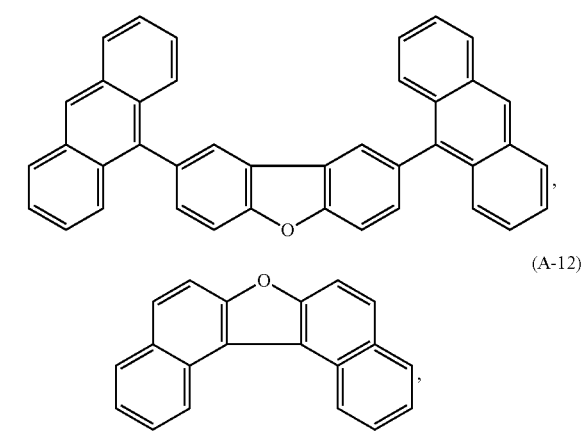
(A-12)
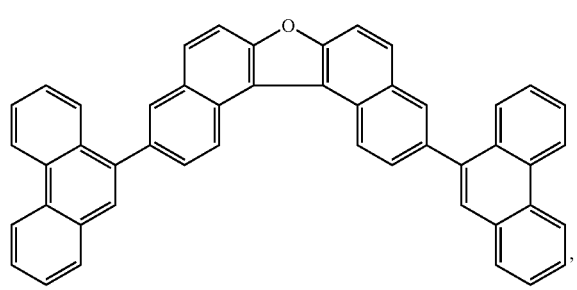
(A-13)
(A-14)
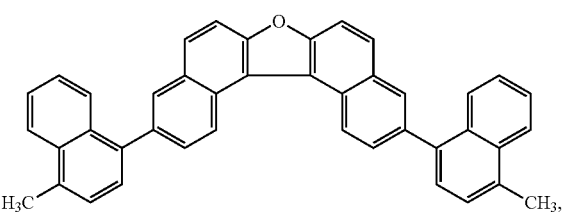
(A-15)
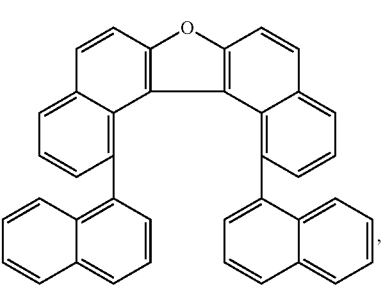
(A-16)
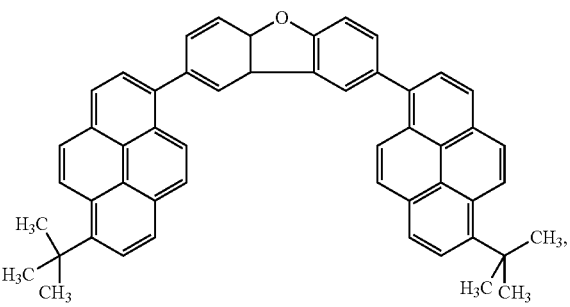
(A-17)
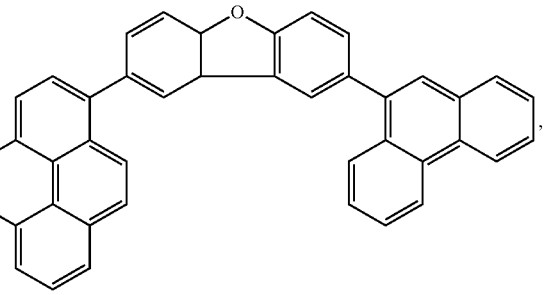
(A-18)
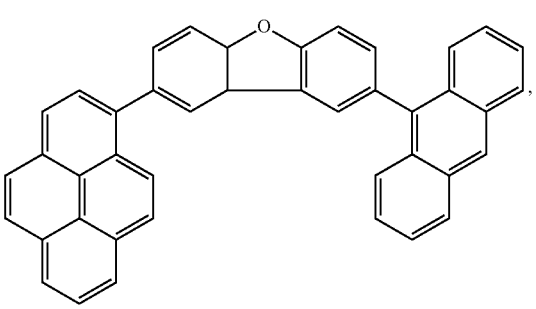

(A-19)
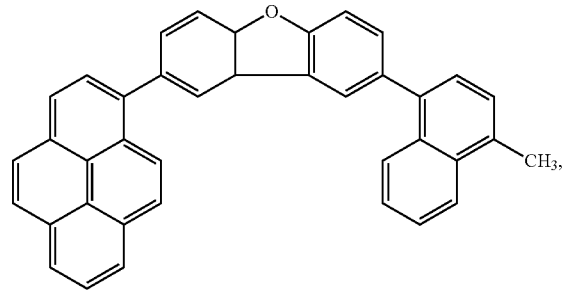
(A-25)
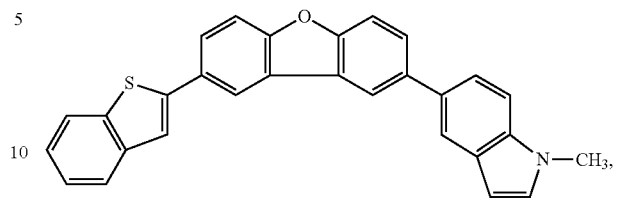
(A-20)
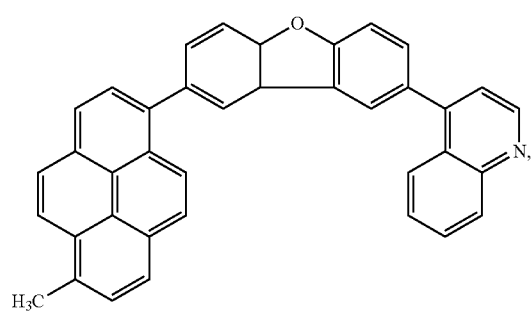
(A-26)
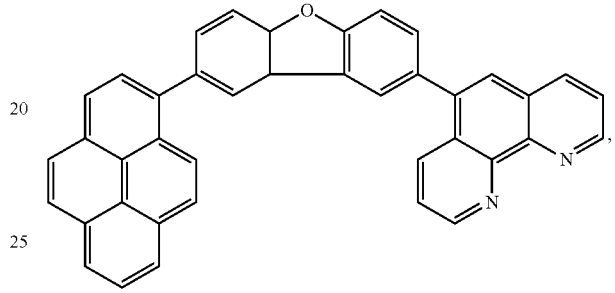
(A-21)
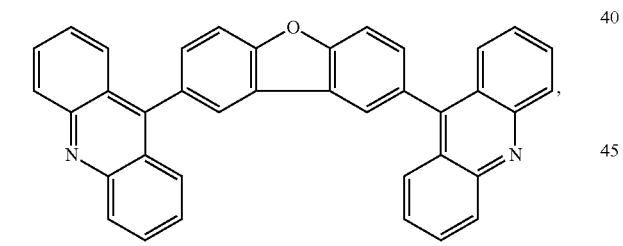
(A-22)
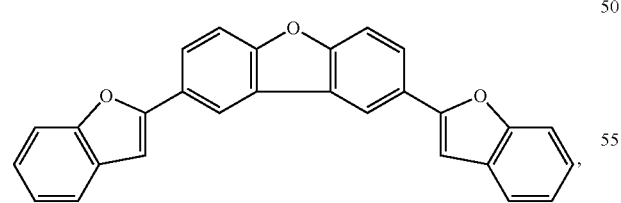
(A-27)
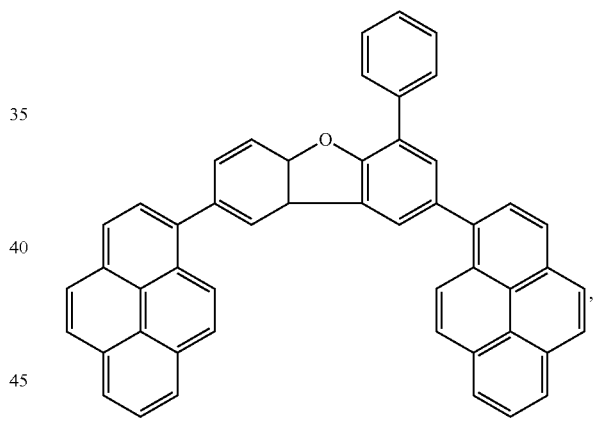
(A-23)
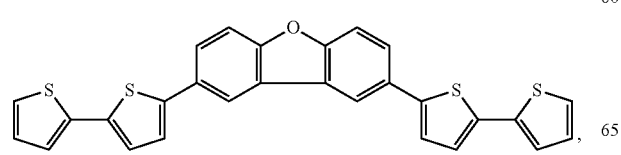
(A-24)
(A-28)
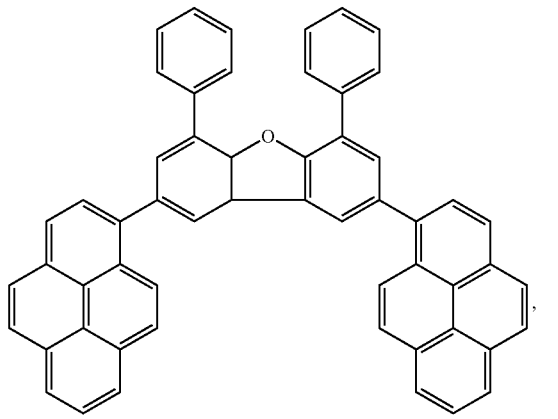

(A-29)
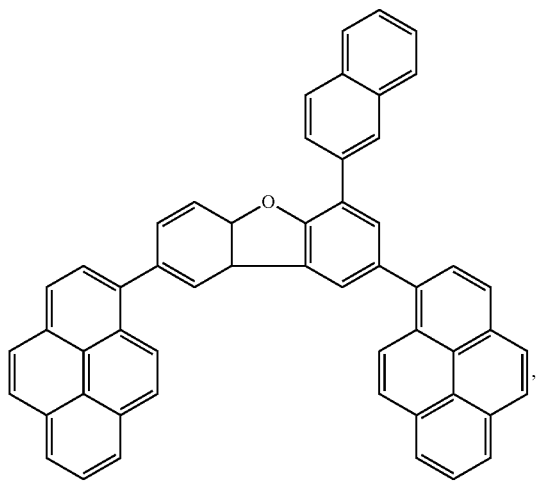
(A-30)
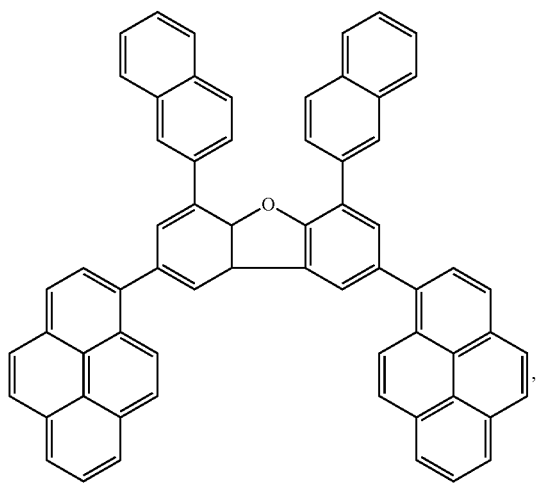
(A-31)
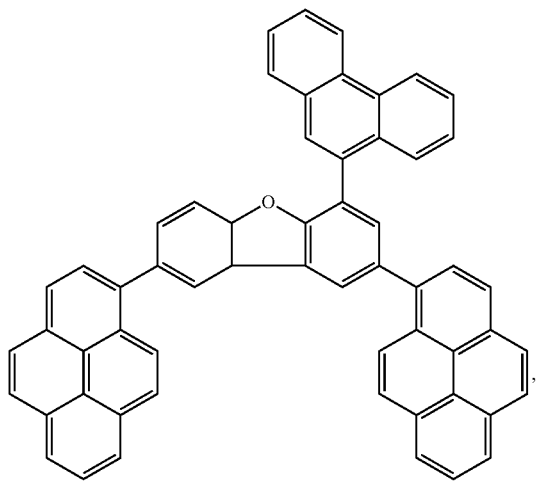
(A-32)
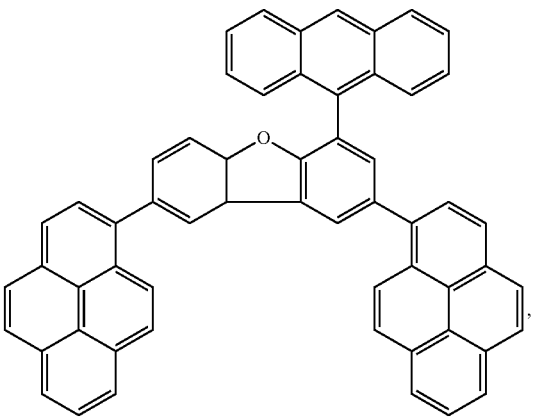
(A-33)
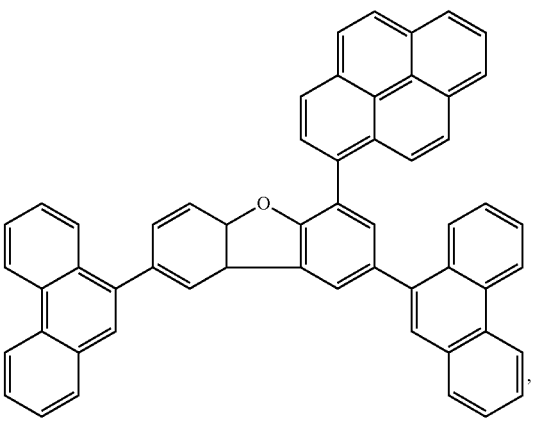
(A-34)
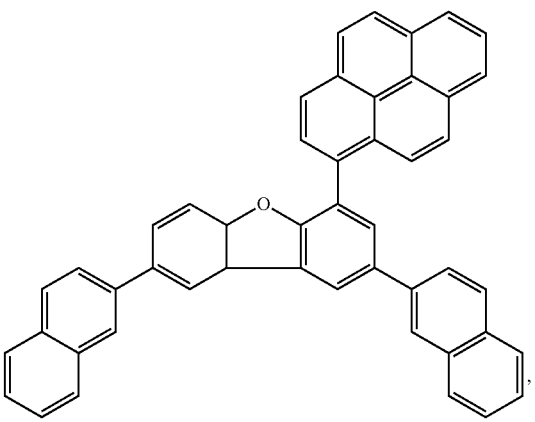

(A-35)
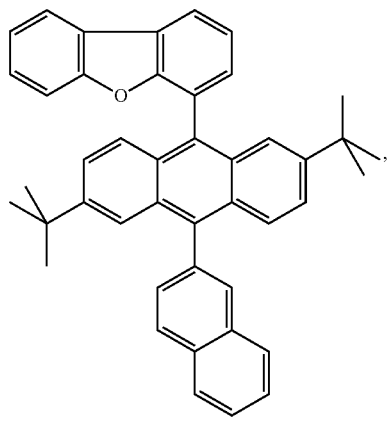
(A-36)
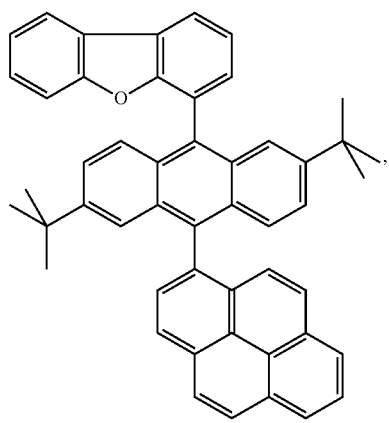
(A-37)
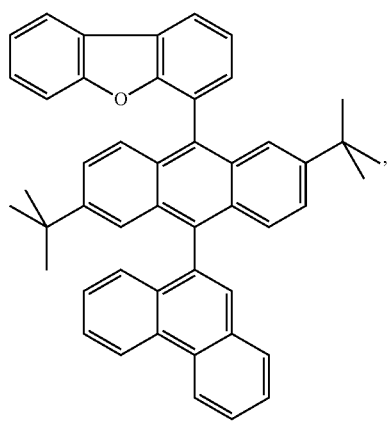
(A-38)
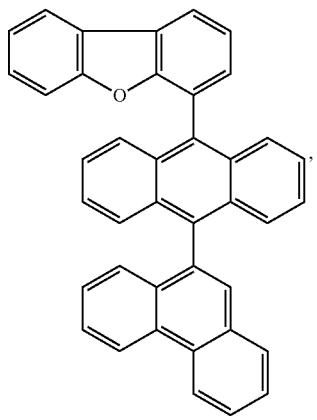
(A-39)
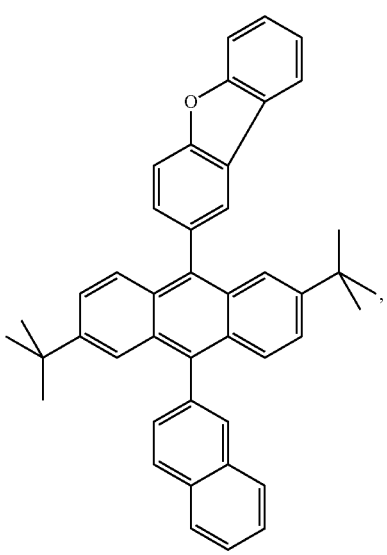
(A-40)
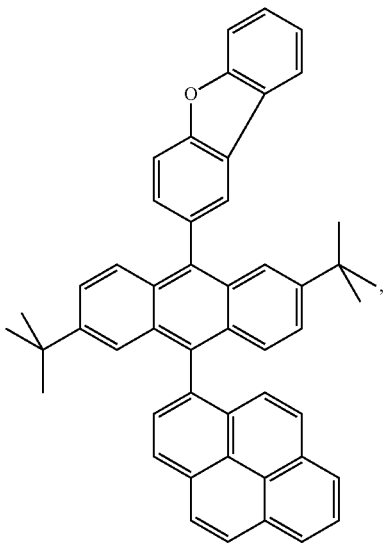

(A-41)
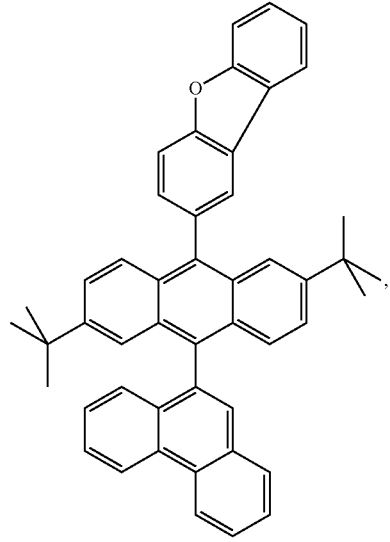
(A-48)
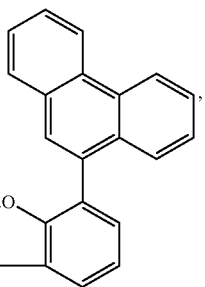
(A-42)
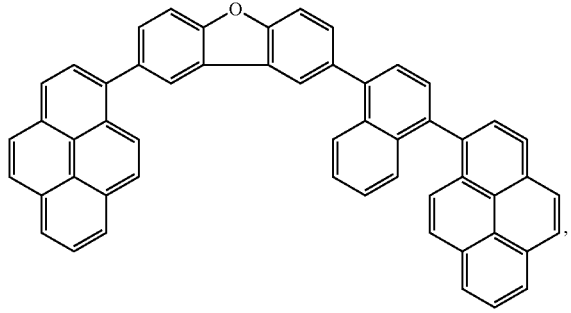
(A-49)
(A-47)
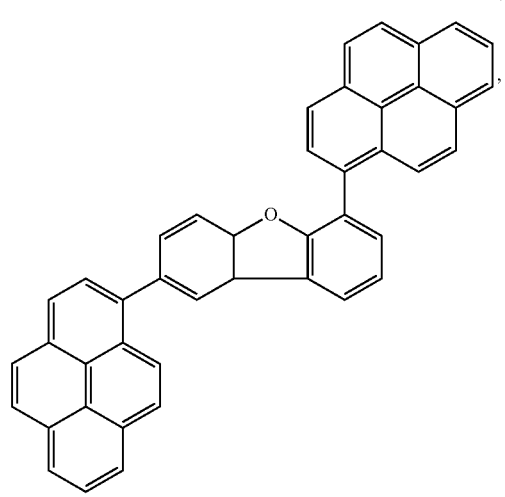
(A-50)
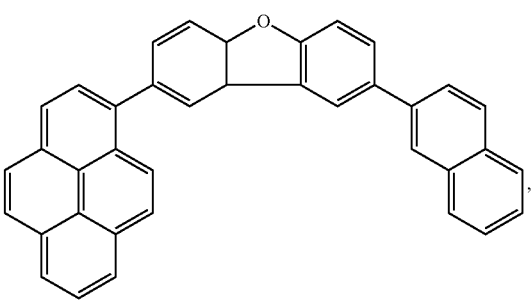
(A-51)
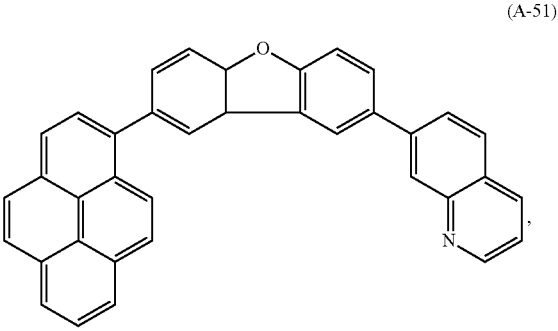

(A-52)
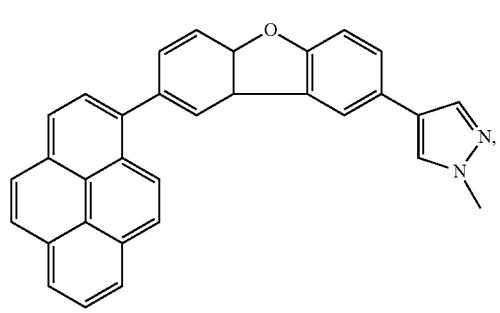
(A-53)
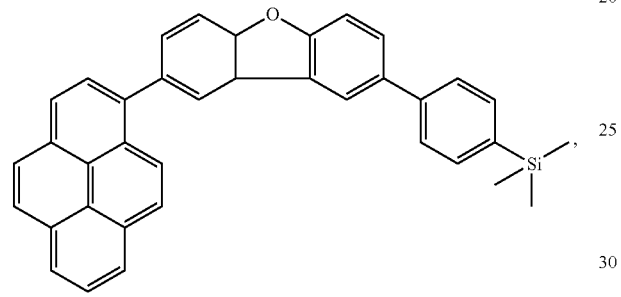
(A-54)
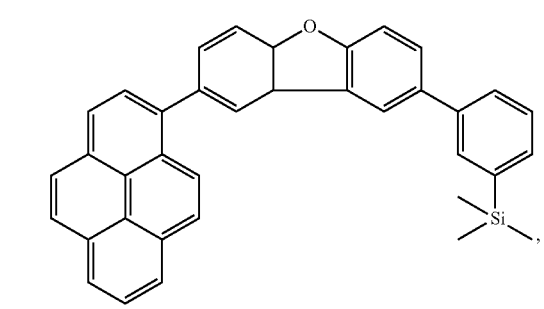
(A-55)
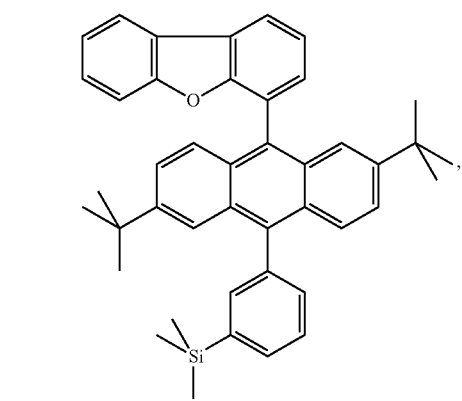
(A-56)
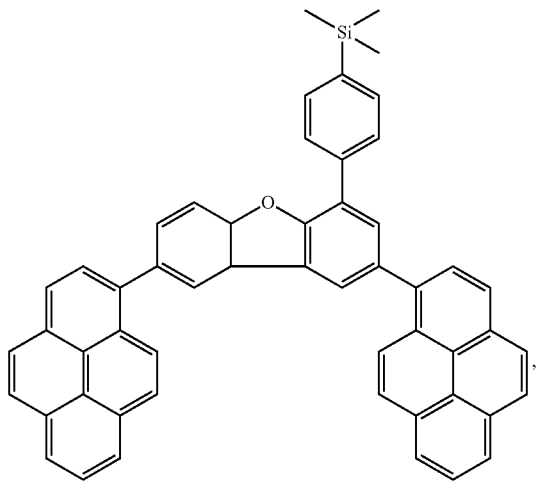
(A-57)
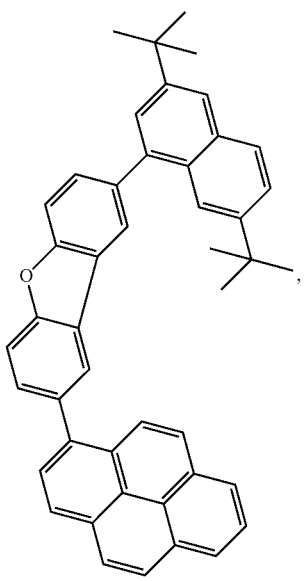
(A-58)
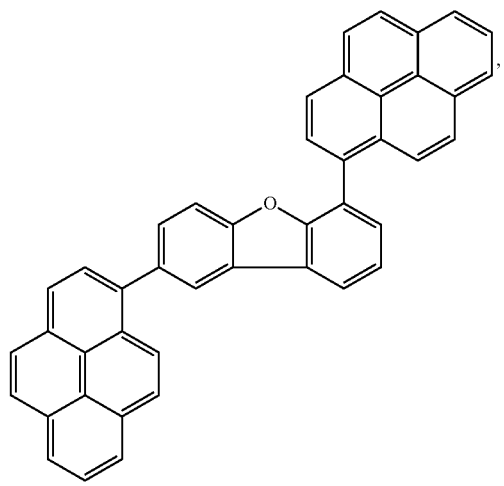

-continued
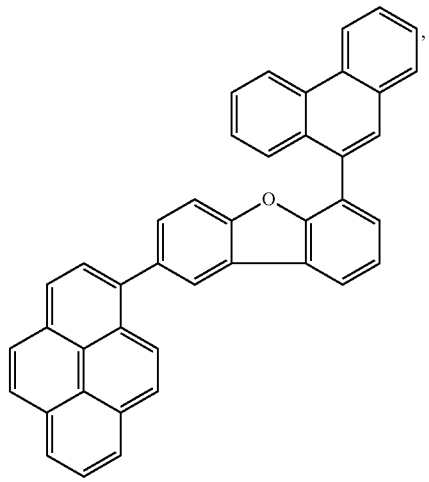
(A-59)
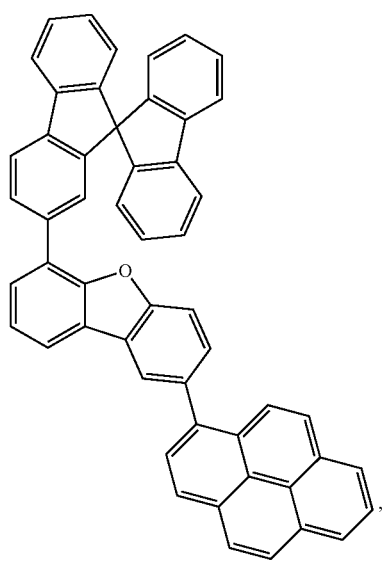
(A-60)
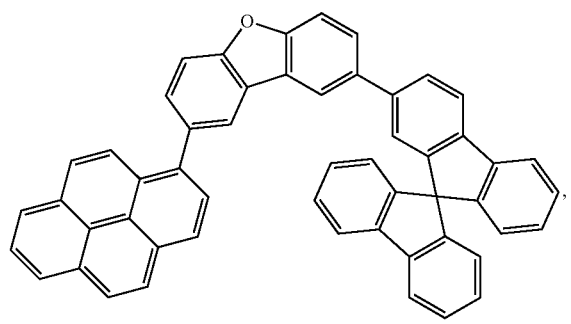
(A-61)
-continued
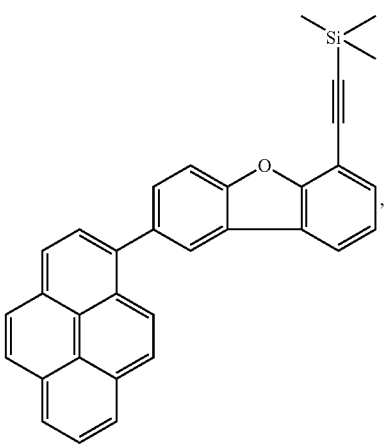
(A-62)
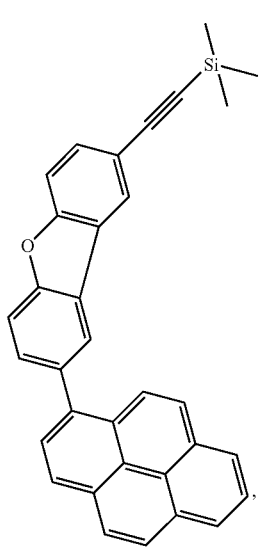
(A-63)
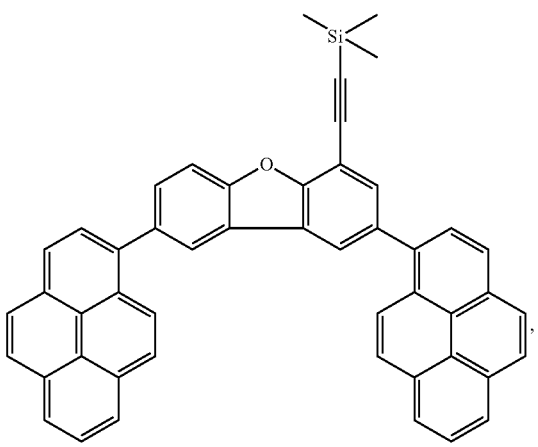
(A-64)

(A-65)

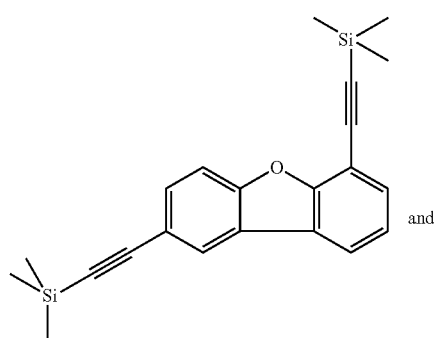

and (A-66)

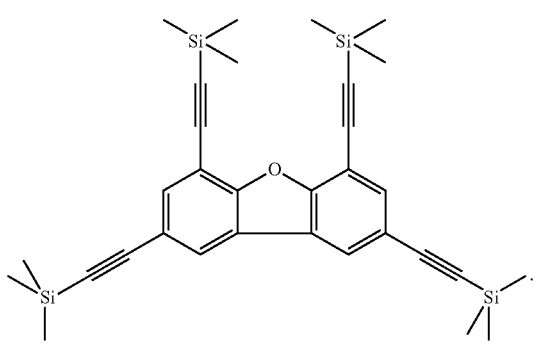

Particularly suitable dibenzo-, dinaphthofurans are compounds A-1, A-2, A-4, A-5, A-10, A-11, A-16, A-19, B-1 and B-2.

In another preferred embodiment at least one, preferably two of the substituents $R^{81}$, $R^{82}$, $R^{83}$, $R^{84}$, $R^{85}$, $R^{86}$, $R^{87}$, $R^{88}$, $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are independently of each other a group of the formula —$W^1$—$(W^2)_b$—$W^3$ ($Y^2$), wherein b is 0, or, 1, $W^1$ and $W^2$ are as defined above and are preferably independently of each other a group of formula

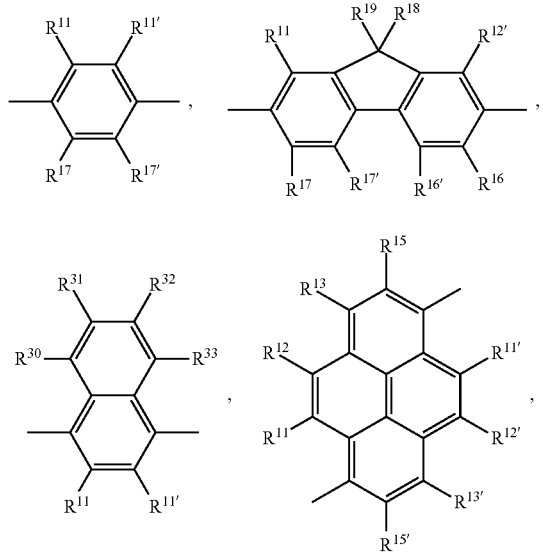

especially

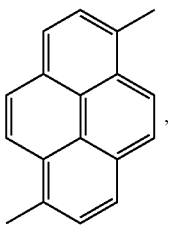

or

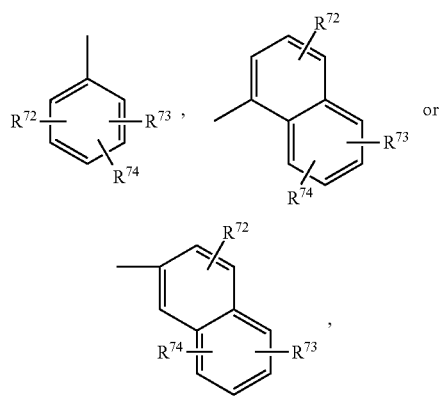

$W^3$ is a group of formula —$NR^{70}R^{71}$, wherein $R^{70}$ and $R^{71}$ are independently of each other a group of formula

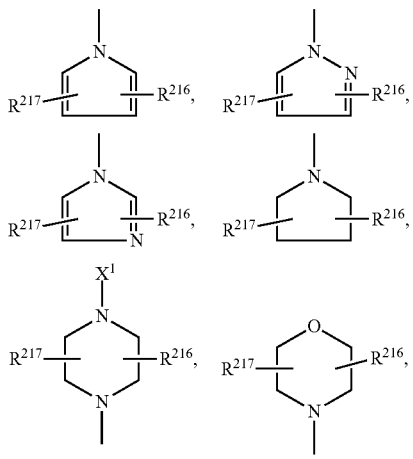

wherein $R^{72}$, $R^{73}$ and $R^{74}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group, or $R^{70}$ and $R^{71}$ together with the nitrogen atom to which they are bonded form a five or six membered heterocyclic ring, such as -continued

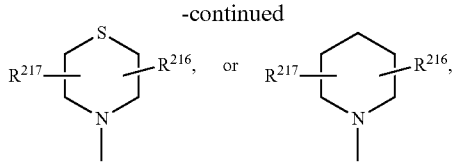

which can be condensed by one or two optionally substituted phenyl groups, such as

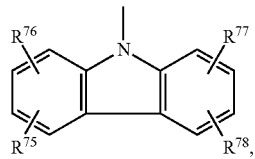

wherein $R^{216}$ and $R^{217}$ independently from each other stands for hydrogen, $C_1$-$C_8$alkyl, $C_1$-$C_8$alkoxy, or phenyl, and $X^1$ stands for hydrogen, or $C_1$-$C_8$alkyl;

$R^{75}$, $R^{76}$, $R^{77}$ and $R^{78}$ are independently of each other H, E, $C_6$-$C_{18}$aryl; $C_6$-$C_{18}$aryl which is substituted by E; $C_1$-$C_{18}$alkyl; $C_1$-$C_{18}$alkyl which is substituted by G and/or interrupted by D; $C_7$-$C_{18}$aralkyl; or $C_7$-$C_{18}$aralkyl which is substituted by E; wherein D, E, G, $R^{11}$, $R^{11'}$, $R^{12'}$, $R^{16}$, $R^{16'}$, $R^{17}$, $R^{17'}$, $R^{18}$, $R^{19}$, $R^{30}$, $R^{31}$, $R^{32}$ and $R^{33}$ are as defined above, and $R^{30'}$, $R^{31'}$, $R^{32'}$ and $R^{33'}$ independently of each other have the meaning of $R^{30}$.

If $R^{70}$ and $R^{71}$ are independently of each other a group of formula

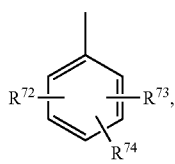

b is preferably 1.

In said embodiment groups of the formula —$W^1$—$(W^2)_b$—$W^3$ are more preferred, wherein b is 0, or 1, $W^1$ and $W^2$ are independently of each other a group of formula

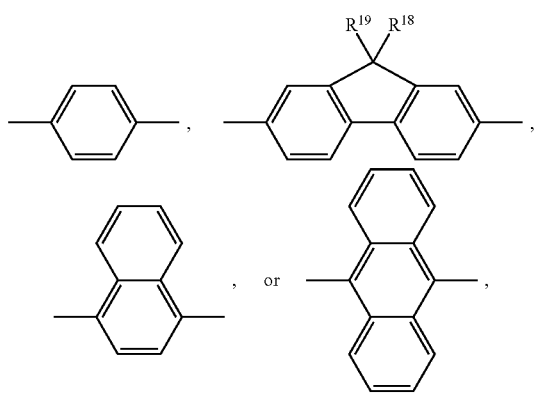

$W^3$ is a group of formula

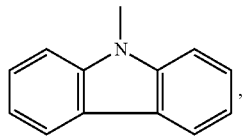

or —$NR^{70}R^{71}$, wherein $R^{70}$ and $R^{71}$ are independently of each other a group of formula

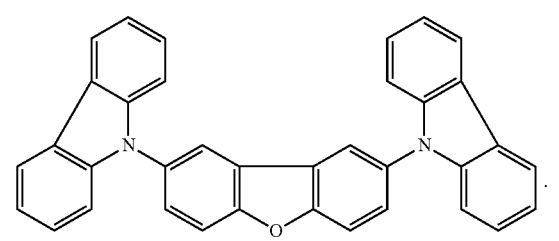

wherein $R^{72}$ is $C_{1-18}$alkyl.

In said embodiment of the present invention compounds of formula Ia and Ib are preferred, wherein $R^{82}$ and $R^{87}$ and $R^{83}$ and $R^{86}$ are independently of each other a group of formula —$(W^2)_b$—$W^3$. The groups —$(W^2)_b$—$W^3$ can be different, but are preferably the same.

Examples of preferred compounds are given below:

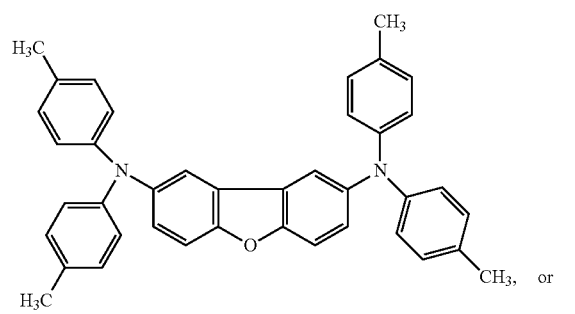

In another preferred embodiment the present invention is directed to compounds of formula I wherein at least one of $R^{81}$, $R^{82}$, $R^{83}$, $R^{84}$, $R^{85}$, $R^{86}$, $R^{87}$ and $R^{88}$ is a group $Y^1$ and at least one of $R^{81}$, $R^{82}$, $R^{83}$, $R^{84}$, $R^{85}$, $R^{86}$, $R^{87}$ and $R^{88}$ is a group $Y^2$.

In said embodiment compounds of formula Ia are preferred, wherein $R^{81}$ is H, $R^{88}$ is $Y^2$ and $R^{83}$ and $R^{86}$ are $Y^1$; or $R^{81}$ and $R^{88}$ are H, $R^{83}$ is $Y^2$ and $R^{86}$ are $Y^1$.

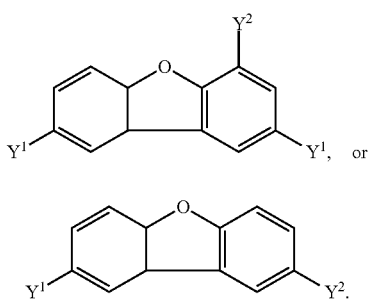, or

Examples of preferred compounds are given below:

(A-43)
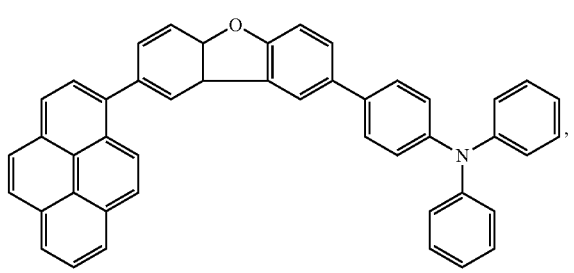, (A-44)
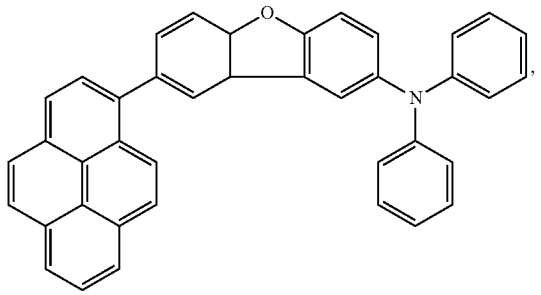, (A-45)
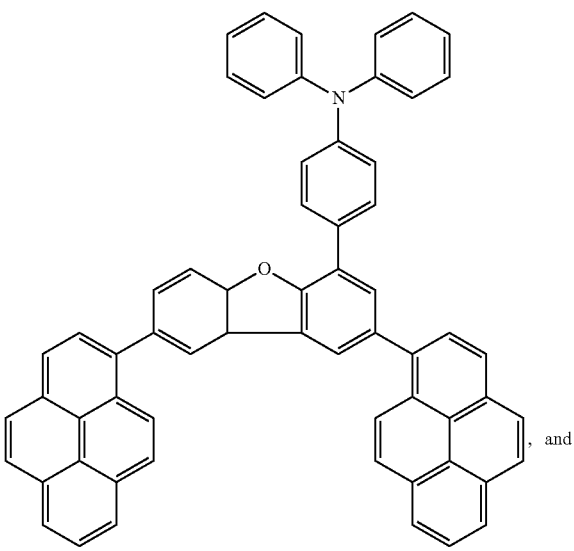, and (A-46)
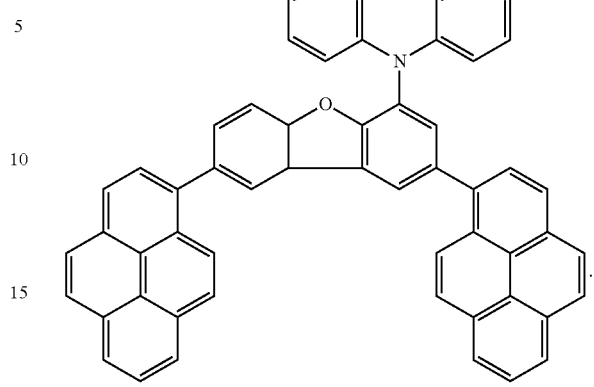

The present benzofuran compounds show a high solid state fluorescence in the desired wavelength range and can be prepared according to or analogous to known procedures (see, for example, WO99/47474, WO2004039786 and WO2004077885).

The benzofuran compounds of the present invention of the formula:

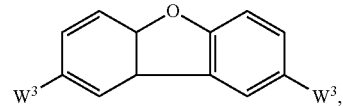, wherein $W^3$ is as defined above, can, for example, be prepared according to a process, which comprises reacting a derivative of formula

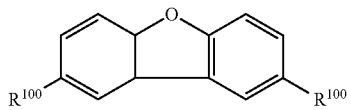

wherein $R^{100}$ stands for halogen such as chloro or bromo, preferably bromo, or E having the meaning of

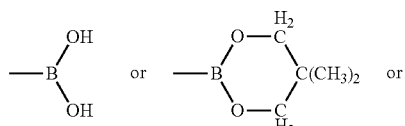 or

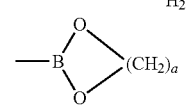

wherein a is 2 or 3,
with boronic acid derivative
$E-W^3$, or in case $R^{100}$ is not halogen -Hal-$W^3$,
wherein Hal stands for halogen, preferably for bromo, in the presence of an allylpalladium catalyst of the µ-halo(tri-isopropylphosphine)($\eta^3$-allyl)palladium(II) type (see for example WO99/47474).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, $Na_2CO_3$, $K_2CO_3$, $Cs_2CO_3$ and the like, preferably an aqueous $K_2CO_3$ solution is chosen. Usually, the molar ratio of the base to compound III is chosen in the range of from 0.5:1 to 50:1.

Generally, the reaction temperature is chosen in the range of from 40 to 180° C., preferably under reflux conditions.

Preferred, the reaction time is chosen in the range of from 1 to 80 hours, more preferably from 20 to 72 hours.

In a preferred embodiment a usual catalyst for coupling reactions or for polycondensation reactions is used, preferably Pd-based catalyst such as known tetrakis(triarylphosphonium)-palladium, preferably $(Ph_3P)_4Pd$ and derivatives thereof. Usually, the catalyst is added in a molar ratio from inventive DPP polymer to the catalyst in the range of from 100:1 to 10:1, preferably from 50:1 to 30:1.

Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

The obtained inventive polymer can be isolated by well-known methods. Preferably, after cooling down the reaction mixture to room temperature, it is poured into acetone and the obtained precipitation is filtered off, washed and dried.

$C_1$-$C_{18}$Alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, or octadecyl.

$C_1$-$C_{18}$Alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{18}$Alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$Alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl or 1-tetracosyn-24-yl.

$C_4$-$C_{18}$cycloalkyl is preferably $C_5$-$C_{12}$cycloalkyl, such as, for example, cyclopentyl, cyclohexyl, cycloheptyl, cyclooctyl, cyclononyl, cyclodecyl, cyclododecyl. Cyclohexyl and cyclododecyl are most preferred.

The term "aryl group" is typically $C_6$-$C_{30}$aryl, such as phenyl, indenyl, azulenyl, naphthyl, biphenyl, terphenylyl or quadphenylyl, as-indacenyl, s-indacenyl, acenaphthylenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 9-phenanthryl, 2- or 9-fluorenyl, 3- or 4-biphenyl, which may be unsubstituted or substituted. Examples of $C_6$-$C_{18}$aryl are phenyl, 1-naphthyl, 2-naphthyl, 3- or 4-biphenyl, 9-phenanthryl, 2- or 9-fluorenyl, which may be unsubstituted or substituted.

$C_7$-$C_{24}$aralkyl radicals are preferably $C_7$-$C_{18}$aralkyl radicals, which may be substituted, such as, for example, benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

$C_7$-$C_{12}$alkylaryl is, for example, a phenyl group substituted with one, two or three $C_1$-$C_6$alkyl groups, such as, for example, 2-, 3-, or 4-methylphenyl, 2-, 3-, or 4-ethylphenyl, 3-, or 4-isopropylphenyl, 3,4-dimethylphenyl, 3,5-dimethylphenyl, or 3,4,5-trimethylphenyl.

The term "heteroaryl group", especially $C_2$-$C_{30}$heteroaryl, is a ring, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, 2H-chromenyl, xanthenyl, dibenzofuranyl, phenoxythienyl, pyrrolyl, imidazolyl, pyrazolyl, pyridyl, bipyridyl, triazinyl, pyrimidinyl, pyrazinyl, 1H-pyrrolizinyl, isoindolyl, pyridazinyl, indolizinyl, isoindolyl, indolyl, 3H-indolyl, phthalazinyl, naphthyridinyl, quinoxalinyl, quinazolinyl, cinnolinyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, 4aH-carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the above-mentioned mono- or bicyclic heterocyclic radicals, which may be unsubstituted or substituted.

Halogen is fluorine, chlorine, bromine and iodine.

The terms "haloalkyl" mean groups given by partially or wholly substituting the above-mentioned alkyl group, with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$alkyl group, a $C_6$-$C_{24}$aryl group or a $C_7$-$C_{12}$aralkylgroup, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

As described above, the aforementioned radicals may be substituted by E and/or, if desired, interrupted by D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{n'}$—$R^x$, where n' is a number from the range 1-9 and $R^x$ is H or $C_1$-$C_{10}$alkyl or $C_2$-$C_{10}$alkanoyl (e.g. CO—CH($C_2H_5$)$C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2CO$-$OR^z$, where $R^z$ is H, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—C($CH_3$)=$CH_2$.

The electroluminescent devices may be employed for full color display panels in, for example, mobile phones, televisions and personal computer screens.

The electroluminescent devices of the present invention are otherwise designed as is known in the art, for example as described in U.S. Pat. Nos. 5,518,824, 6,225,467, 6,280,859, 5,629,389, 5,486,406, 5,104,740, 5,116,708 and 6,057,048, the relevant disclosures of which are hereby incorporated by reference.

For example, organic EL devices contain one or more layers such as:

substrate; base electrode; hole-injecting layer; hole transporting layer; emitter layer; electron-transporting layer; electron-injecting layer; top electrode; contacts and encapsulation.

This structure is a general case and may have additional layers or may be simplified by omitting layers so that one layer performs a plurality of tasks. For instance, the simplest organic EL device consists of two electrodes which sandwich an organic layer that performs all functions, including the function of light emission.

A preferred EL device comprises in this order:
(a) an anode,
(b) a hole injecting layer and/or a hole transporting layer,
(c) a light-emitting layer,
(d) optionally an electron transporting layer and
(e) a cathode.

The benzofuran compounds of the present invention can, in principal be used for any organic layer, such as, for example, hole transporting layer, light emitting layer, or electron transporting layer, but are preferably used as the light emitting material in the light emitting layer, optionally as a host or guest component, or electron transporting layer.

In particular, the present organic compounds function as light emitters and are contained in the light emission layer or form the light-emitting layer.

The light emitting compounds of this invention exhibit intense fluorescence in the solid state and have excellent electric-field-applied light emission characteristics. Further, the light emitting compounds of this invention are excellent in the injection of holes from a metal electrode and the transportation of holes; as well as being excellent in the injection of electrons from a metal electrode and the transportation of electrons. They are effectively used as light emitting materials and may be used in combination with other hole transporting materials, other electron transporting materials or other dopants.

The organic compounds of the present invention form uniform thin films. The light emitting layers may therefore be formed of the present organic compounds alone.

Alternatively, the light-emitting layer may contain a known light-emitting material, a known dopant, a known hole transporting material or a known electron transporting material as required. In the organic EL device, a decrease in the brightness and life caused by quenching can be prevented by forming it as a multi-layered structure. The light-emitting material, a dopant, a hole-injecting material and an electron-injecting material may be used in combination as required. Further, a dopant can improve the light emission brightness and the light emission efficiency, and can attain the red or blue light emission. Further, each of the hole transporting zone, the light-emitting layer and the electron transporting zone may have the layer structure of at least two layers. In the hole transporting zone in this case, a layer to which holes are injected from an electrode is called "hole-injecting layer", and a layer which receives holes from the hole-injecting layer and transport the holes to a light-emitting layer is called "hole transporting layer". In the electron transporting zone, a layer to which electrons are injected from an electrode is called "electron-injecting layer", and a layer which receives electrons from the electron-injecting layer and transports the electrons to a light-emitting layer is called "electron transporting layer". These layers are selected and used depending upon factors such as the energy level and heat resistance of materials and adhesion to an organic layer or metal electrode.

The light-emitting material or the dopant which may be used in the light-emitting layer together with the organic compounds of the present invention includes for example anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and fluorescent dyestuffs for a dyestuff laser or for brightening.

It is also possible to use the compounds of the present invention with phosphorescent materials as a dopant in the light-emitting layer. Examples of the phosphorescent materials are, for example, metal complexes of Ir, Pt, Eu, Ru, Rh, Pd, Ag, Re, Os and Au and are described, for example, in JP2005-11804 and WO2004/034751.

Examples of typical structures of the metal complex are shown below:

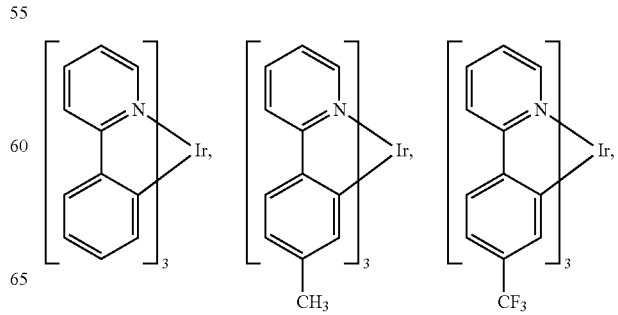

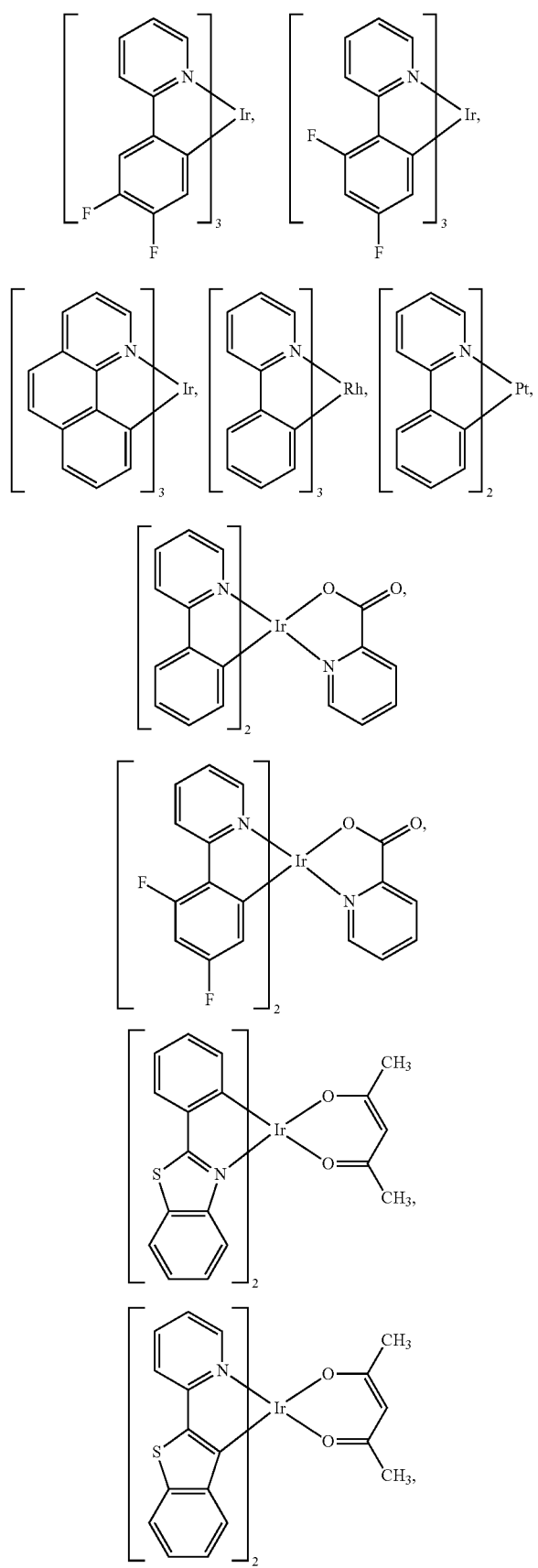
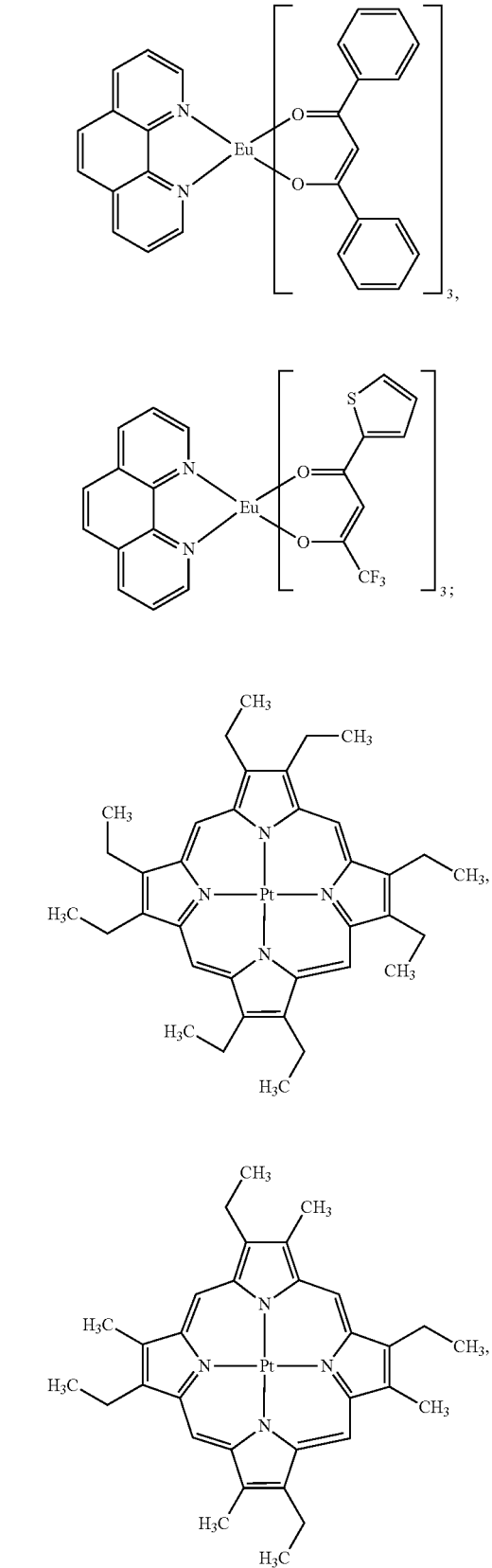

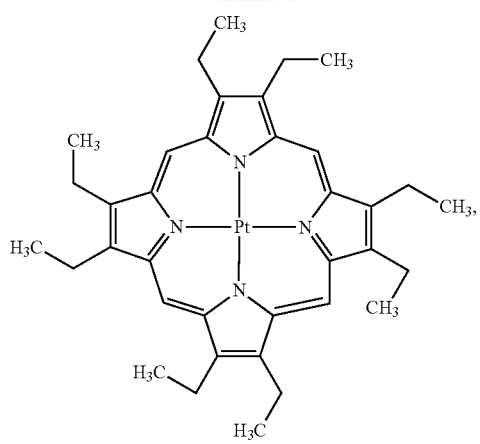
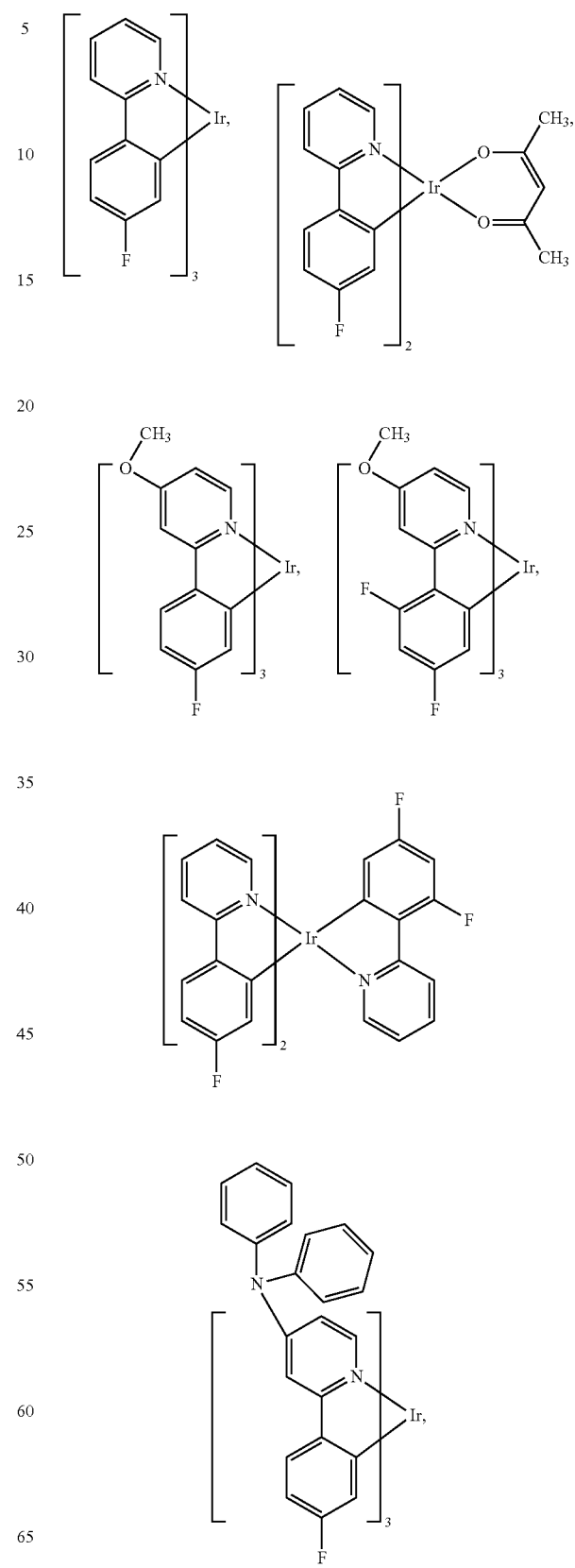

71
-continued
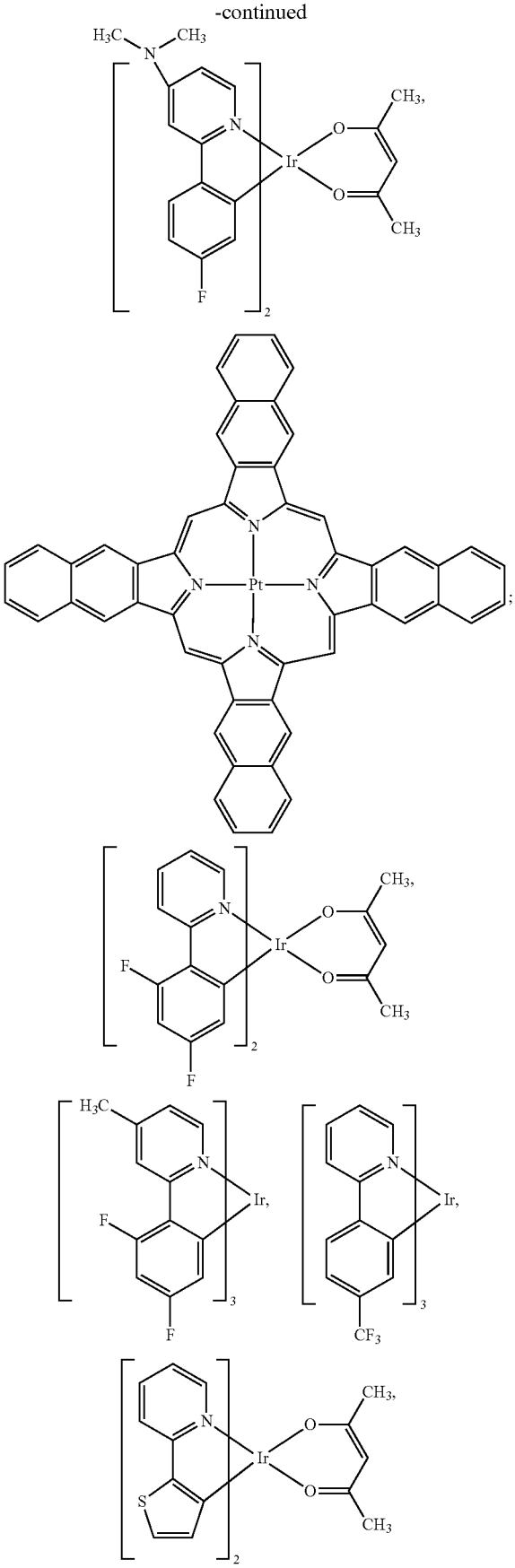
72
-continued
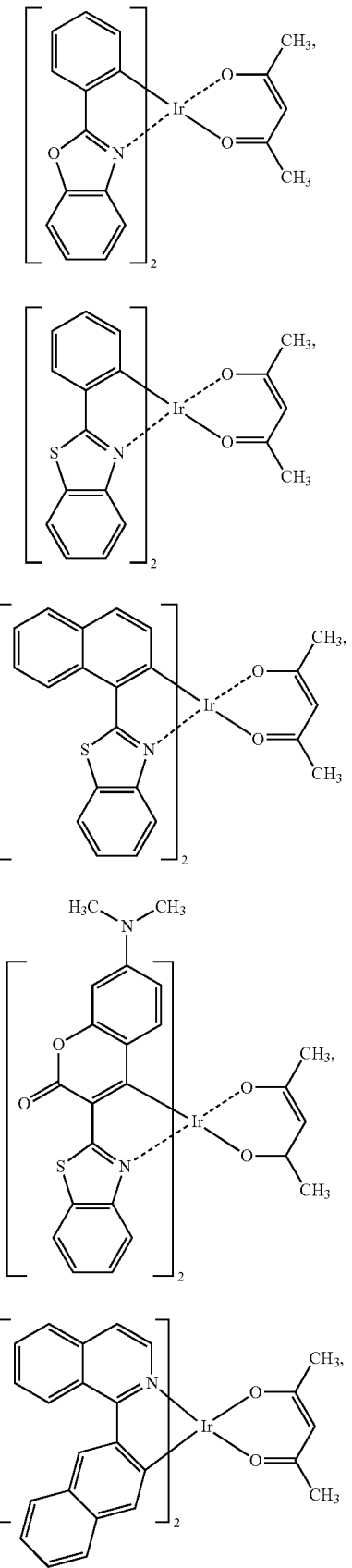

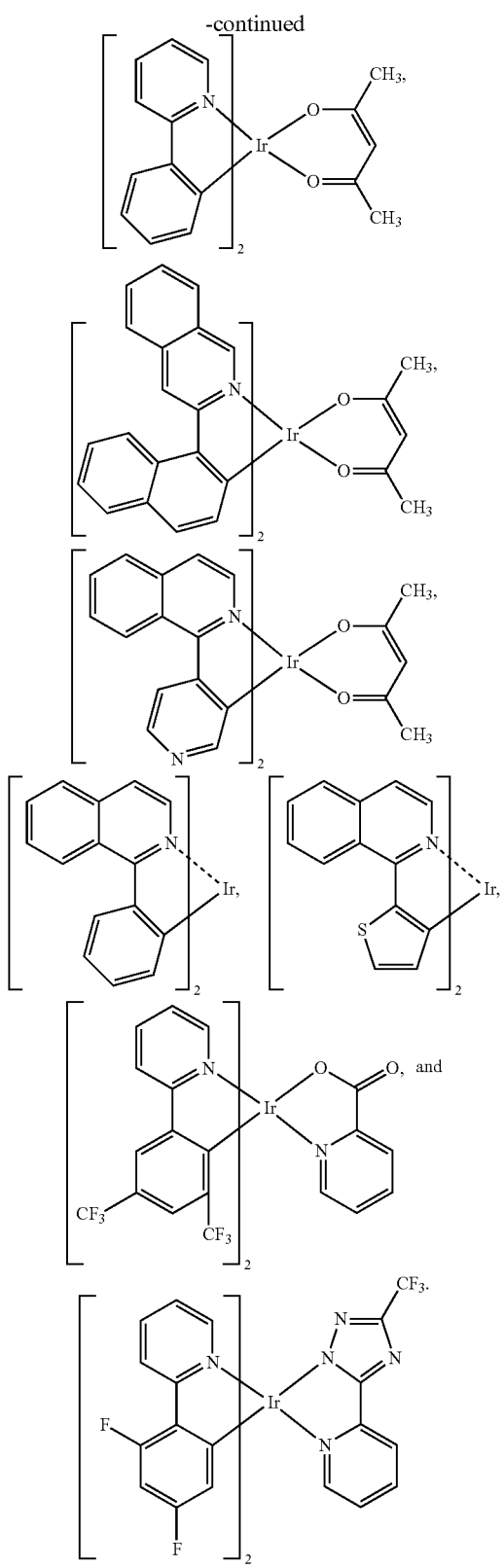

In that case the electroluminescent device may comprise in this order (a) an anode, such as, for example, ITO, (b1) a hole injecting layer, such as, for example, CuPc, (b2) a hole transporting layer, such as, for example, such as, for example, N,N'-Di(naphthalene-1-yl)-N,N'-diphenyl-benzidine (NPD), or TCTA, (c) a light-emitting layer, comprising a phosphorescent compound and a dibenzofuran compound of the present invention, especially a compound A-1 to A-66, B-1 to B-18, C-1 and C-2.

a positive hole inhibiting layer, such as, for example, BCP, or BAlq, (d) an electron transporting layer, such as, for example, Alq$_3$, and an inorganic compound layer, such as, for example, LiF, (e) a cathode, such as, for example, Al.

If the dibenzofuran compounds of the present invention are used as host together with guest compounds, such, as for example, 2,5,8,11-tetra-t-butylperylene (Jiaumin Shi Ching W. Tang, Appl. Phys. Lett. 80, 3201 (2002), or the compounds, described, for example, in WO03/105538, such as, for example,

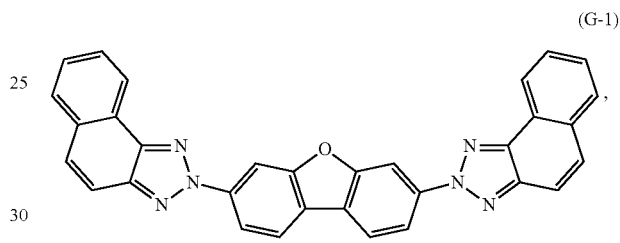

(G-1)

the electroluminescent device may comprise in this order (a) an anode, such as, for example, ITO, (b1) a hole injecting layer, such as, for example, CuPc, (b2) a hole transporting layer, such as, for example, NPD, or TCTA, (c) a light-emitting layer, comprising a fluorescent guest compound and a dibenzofuran host compound of the present invention, especially a compound A-1 to A-66, B-1 to B-18, C-1 and C-2, optionally a positive hole inhibiting layer, such as, for example, BCP, (d) an electron transporting layer, such as, for example, Alq$_3$, or TPBI and an inorganic compound layer, such as, for example, LiF, (e) a cathode, such as, for example, Al.

The weight ratio of compound of the formula I to the dopant in general 50:50 to 99.99:0.01, preferably 90:10 to 99.99: 0.01, more preferably 95:5 to 99.9:0.1. If the guest is a phosphorescent compound, its concentration is normally 5-10%.

Accordingly, the present invention also relates to compositions comprising a compound of the present invention.

The compounds of the present invention and the above compound or compounds that can be used in a light-emitting layer may be used in any mixing ratio for forming a light-emitting layer. That is, the organic compounds of the present invention may provide a main component for forming a light-emitting layer, or they may be a doping material in another main material, depending upon a combination of the above compounds with the organic compounds of the present invention.

The hole-injecting material is selected from compounds which are capable of transporting holes, are capable of receiving holes from the anode, have an excellent effect of injecting holes to a light-emitting layer or a light-emitting material, prevent the movement of excitons generated in a light-emitting layer to an electron-injecting zone or an electron-injecting material and have the excellent capability of forming a thin film. Suitable hole-injecting materials include for example a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electroconducting polymer.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyldiphenylamine, N,N'-diphenyl-N,N'-(3-methylphenyl)-1,1-biphenyl-4,4'-diamine, N,N,N',N'-tetra(4-methylphenyl)-1,1'-phenyl-4,4'-diamine, N,N,N',N'-tetra(4-methylphenyl)-1,1'-biphenyl-4,4'-diamine, N,N'-diphenyl-N,N'-di(1-naphthyl)-1,1'-biphenyl-4,4'-diamine, N,N'-di(methylphenyl)-N,N'-di(4-n-butylphenyl)-phenanthrene-9,10-diamine, 4,4',4"-tris(3-methylphenyl)-N-phenylamino) triphenylamine, 1,1-bis(4-di-p-tolylaminophenyl) cyclohexane, and oligomers or polymers having aromatic tertiary amine structures of these.

Although not specially limited, specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O—GaPc.

The hole transporting layer can reduce the driving voltage of the device and improve the confinement of the injected charge recombination within the light emitting layer, comprising the compounds of the present invention. Any conventional suitable aromatic amine hole transporting material described for the hole-injecting layer may be selected for forming this layer.

A preferred class of hole transporting materials is comprised of 4,4'-bis(9-carbazolyl)-1,1'-biphenyl compounds of the formula

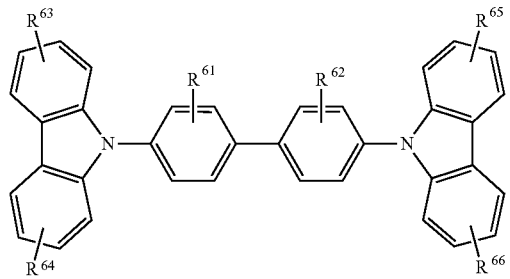

wherein $R^{61}$ and $R^{62}$ is a hydrogen atom or an $C_1$-$C_3$alkyl group; $R^{63}$ through $R^{66}$ are substituents independently selected from the group consisting of hydrogen, a $C_1$-$C_6$alkyl group, a $C_1$-$C_6$alkoxy group, a halogen atom, a dialkylamino group, a $C_6$-$C_{30}$aryl group, and the like.

Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like; or 4,4',4"-tri-(N-carbazoyl)triphenylamine (TCTA).

In addition, polymeric material can be used as a hole injection material and a hole transporting material, such as poly (N-vinylcarbazole) (PVK), polythiophenes, polypyrrole, polyaniline, and copolymers such as poly(3,4-ethylenedioxythiophene)/poly(4-styrenesulfonate), also called PEDOT/PSS.

The electron transporting layer is not necessarily required for the present device, but is optionally and preferably used for the primary purpose of improving the electron injection characteristics of the EL devices and the emission uniformity. Illustrative examples of electron transporting compounds, which can be utilized in this layer, include the metal chelates of 8-hydroxyquinoline as disclosed in U.S. Pat. Nos. 4,539, 507, 5,151,629, and 5,150,006, the disclosures of which are totally incorporated herein by reference.

Examples of suitable electron transporting materials are metal complex compounds and nitrogen-containing five-membered ring derivatives.

Although not specially limited, specific examples of the metal complex compound include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), gallium bis(2-methyl-8-quinolinate)(2-naphtholate), gallium bis(2-methyl-8-quinolinate)phenolate, zinc bis(o-(2-benzooxazolyl)phenolate), zinc bis(o-(2-benzothiazolyl)phenolate) and zinc bis(o-(2-benzotrizolyl)phenolate). The nitrogen-containing five-membered derivative is preferably an oxazole, thiazole, thiadiazole, or triazole derivative. Although not specially limited, specific examples of the above nitrogen-containing five-membered derivative include 2,5-bis(1-phenyl)-1,3,4-oxazole, 1,4-bis(2-(4-methyl-5-phenyloxazolyl)benzene, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)] benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. Another class of electron transport materials are oxadiazole metal chelates, such as bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis[2-(2-hydroxyphenyl)-5-(1-naphthyl)-1,3,4-oxadiazolato] zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolatopithium; bis[2-(2-hydroxyphenyl)-5-p-tolyl-1,3,4-oxadiazolato]zinc; bis[2-(2-hydroxyphenyl)-5-p-tolyl-1,3,4-oxadiazolato]beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato]zinc; bis[2-(2-hydroxyphenyl)-5-(4-fluorophenyl)-1,3,4-oxadiazolato] zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato]zinc; bis[2-(2-hydroxy phenyl)-5-(4-methoxyphenyl)-1,3,4-oxadiazolato]zinc; bis

[2-(2-hydroxy-4-methylphenyl)-5-phenyl-1,3,4-oxadiazolato]zinc; bis[2-.alpha.-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis[2-(2-hydroxyphenyl)-5-p-pyridyl-1,3,4-oxadiazolato]beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato]beryllium, and the like.

Other suitable compounds for the electron transporting material are hetero-cyclic compounds such as benzimidazole derivatives, benzoxazole derivatives, oxadiazole derivatives, thiadiazole derivative, triazole derivatives, pyrazine derivatives, phenanthroline derivatives, quinoxaline derivatives, quinoline derivatives, benzoquinoline derivatives, oligo-pyridine derivatives, e.g. bipyridine derivatives and terpyridine derivatives, naphthylidine derivatives, indole derivatives and naphthalimide derivatives; silole derivatives; and phosphineoxide derivatives.

The property of charge injection can be improved by adding an electron-accepting compound to the hole injection layer and/or the hole transporting layer and electron-donating material to the electron transporting layer.

It is possible to add reducing dopant to the electron transporting layer to improve the EL device property. The reducing dopant is a material that can reduce the electron transporting material. Examples of the reducing dopant are alkaline metals, e.g. Na, K, Rb and Cs, and alkaline earth metals, e.g. Ca, Sr, and Ba.

The organic EL device of the present invention may comprise an inorganic compound layer between at least one of the electrodes and the above organic thin layer. Examples of the inorganic compound used for the inorganic compound layer include various types of oxides, nitrides and oxide nitrides such as alkali metal oxides, alkaline earth metal oxides, rare earth oxides, alkali metal halides, alkaline earth metal halides, rare earth halides, $SiO_x$, $AlO_x$, $SiN_x$, SiON, AlON, $GeO_x$, $LiO_x$, LiON, $TiO_x$, TiON, $TaO_x$, TaON, $TaN_x$ and C. In particular, as the component contacting the anode, $SiO_x$, $AlO_x$, $SiN_x$, SiON, AlON, $GeO_x$ and C are preferred since a suitable interface layer of injection is formed. As the component contacting the cathode LiF, $Mg F_2$, $CaF_2$ and NaF are preferred.

In the organic EL device of the present invention, the light-emitting layer may contain, in addition to the light-emitting organic material of the present invention, at least one of other light-emitting material, other dopant, other hole-injecting material and other electron-injecting material. For improving the organic EL device of the present invention in the stability against temperature, humidity and ambient atmosphere, a protective layer may be formed on the surface of the device, or the device as a whole may be sealed with a silicone oil, or the like.

The electrically conductive material used for the anode of the organic EL device is suitably selected from those materials having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electroconducting polymers, such as polythiophene and polypyrrole.

The electrically conductive material used for the cathode is suitably selected from those having a work function of smaller than 4 eV. The electrically conductive material includes magnesium, calcium, tin, lead, titanium, yttrium, lithium, ruthenium, manganese, aluminum and alloys of these, while the electrically conductive material shall not be limited to these. Examples of the alloys include magnesium/silver, magnesium/indium and lithium/aluminum, while the alloys shall not be limited to these. Each of the anode and the cathode may have a layer structure formed of two layers or more as required.

For the effective light emission of the organic EL device, at least one of the electrodes is desirably sufficiently transparent in the light emission wavelength region of the device. Further, the substrate is desirably transparent as well. The transparent electrode is produced from the above electrically conductive material by a deposition method or a sputtering method such that a predetermined light transmittance is secured. The electrode on the light emission surface side has for instance a light transmittance of at least 10%. The substrate is not specially limited so long as it has adequate mechanical and thermal strength and has transparency. For example, it is selected from glass substrates and substrates of transparent resins such as a polyethylene substrate, a polyethylene terephthalate substrate, a polyether sulfone substrate and a polypropylene substrate.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. The thickness of each layer is for example in the range of from about 5 nm to about 10 μm, for instance about 10 nm to about 0.2 μm.

In the wet film forming method, a material for forming an intended layer is dissolved or dispersed in a proper solvent, such as toluene, ethanol, chloroform, tetrahydrofuran and dioxane, and a thin film is formed from the solution or dispersion. The solvent shall not be limited to the above solvents. For improving the film formability and preventing the occurrence of pinholes in any layer, the above solution or dispersion for forming the layer may contain a proper resin and a proper additive. The resin that can be used includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electroconducting polymers such as polythiophene and polypyrrole. The above additive includes an antioxidant, an ultraviolet absorbent and a plasticizer.

When the light-emitting organic material of the present invention is used in a light-emitting layer of an organic EL device, an organic EL device can be improved in organic EL device characteristics such as light emission efficiency and maximum light emission brightness. Further, the organic EL device of the present invention is remarkably stable against heat and electric current and gives a usable light emission brightness at a low actuation voltage. The problematic deterioration of conventional devices can be remarkably decreased.

The organic EL device of the present invention has significant industrial values since it can be adapted for a flat panel display of an on-wall television set, a flat light-emitting device, a light source for a copying machine or a printer, a light source for a liquid crystal display or counter, a display signboard, lighting application and a signal light.

The material of the present invention can be used in the fields of an organic EL device, an electrophotographic photoreceptor, a photoelectric converter, a solar cell, and an image sensor.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight.

EXAMPLES

Example 1

Synthesis of 2,8-Bis-((E)-styryl)-dibenzofuran

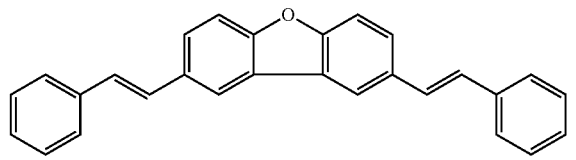

(A-1)

1a) 2,8-Dibromodibenzofuran

Bromine (92.6 g, 0.58 mol) in acetic acid (54 g) is added at 75° C. to a solution of dibenzofuran (23.2 g, 0.14 mol) in acetic acid (232 g). The mixture is then stirred at 75° C. for 3 hours. The reaction mixture is cooled to room temperature and poured into $H_2O$. The orange solid is washed with $Na_2S_2O_3$ aq. and $H_2O$. The crude product is then purified by recrystallization from n-hexane, wherein the pure product is obtained as a white solid (38% yield; mp.: 226° C.).

$^1$H-NMR (CDCl$_3$, ppm): 7.65 (d, 2H), 7.59 (dd, 2H), 8.03 (d, 2H).

1b) 2,8-Bis-((E)-styryl)-dibenzofuran

Tetrethylamine hydroxide (13.6 g, 18.4 mmol), tetrakis (triphenylphosphine)palladium(0) (142 mg) and trans-2-phenylvinylboronic acid (2.3 g, 15.3 mmol) are added to a solution of the product from example 1a) (2.00 g, 6.14 mmol) in N,N'-Dimethylacetamide (DMA) (30 ml). The mixture is then stirred at 110° C. for 24 hours. The reaction mixture is cooled to room temperature and poured into $H_2O$. A gray crude product is obtained after filtration and washing with n-hexane. The crude product is purified by silicagel column chromatography with $CH_2Cl_2$, which result in a white solid (71% yield, mp.: 226° C.).

$^1$H-NMR (CDCl$_3$, ppm): 7.26-7.30 (m, 6H), 7.39 (t, 4H), 7.54-7.58 (m, 6H), 7.65 (dd, 2H), 8.12 (d, 2H)

Example 2

Synthesis of 1,5-dibenzofuranyl-3,7-di-tert-butylnaphthalene

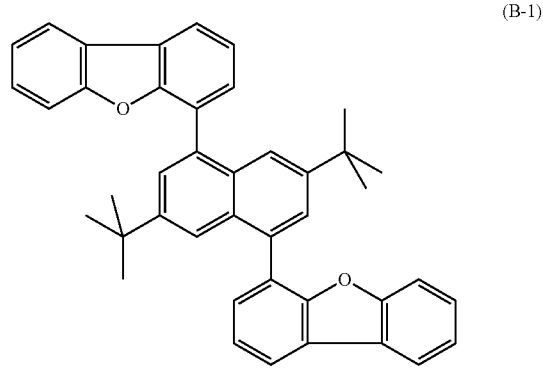 [SMILES: CC(C)(C)c1cc(-c2cccc3c2oc2ccccc23)c2cc(C(C)(C)C)cc(-c3cccc4c3oc3ccccc34)c2c1]

(B-1)

2a) 1,5-dibromo-3,7-di-tert-butylnaphthalene

Fe (212 mg) and bromine (18.3 g, 0.11 mol) in carbontetrachloride (75 ml) are added at 0° C. to a solution of 2,6-di-tert-butylnaphthalene (25 g, 0.1 mol) in carbontetrachloride (300 ml). The mixture is then stirred at 0° C. for 3.5 hours. The reaction mixture is poured into $H_2O$ and then the organic layer is washed with $Na_2S_2O_3$ aq. and $H_2O$. The organic layer is dried over $MgSO_4$ and concentrated by evaporation. The crude product is then purified by silicagel column chromatography with n-hexane, which result in a white solid (31% yield; mp.: 226° C.).

$^1$H-NMR (CDCl$_3$, ppm): 1.41 (s, 18H), 7.88 (d, 2H), 8.11 (d, 2H).

2b) 1,5-Dibenzofuranyl-3,7-di-tert-butylnaphthalene

Tetrethylaminehydroxide (3.5 g, 14.2 mmol), tetrakis (triphenylphosphine)palladium(0) (100 mg) and 4-denzofuranboronic acid (3 g, 14.0 mmol) are added to a solution of the product from example 2a) (1.88 g, 4.72 mmol) in DMA (30 ml). The mixture is stirred at 110° C. for 1 hour, then cooled to room temperature, whereby a yellow solid product is obtained which is isolated by filtration and washed with $H_2O$. The yellow solid is then dissolved in $CH_2Cl_2$ and dried over $MgSO_4$. Concentration by evaporation and silicagel column chromatography with ethylacetate/hexane=1/30 as eluent afforded a pure yellow solid product (65% yield; mp.: 226° C.).

$^1$H-NMR (CDCl$_3$, ppm): 1.98 (s, 18H), 7.38-7.58 (m, 8H), 7.67 (d, 2H), 7.77 (d, 2H), 7.82 (d, 2H), 8.08 (dd, 2H), 8.11 (dd, 2H).

The compounds shown below (examples 3-10) are prepared in analogues manner using the appropriate educts.

| Example | Structure | Mp. [° C.] |
|---|---|---|
| 3 | 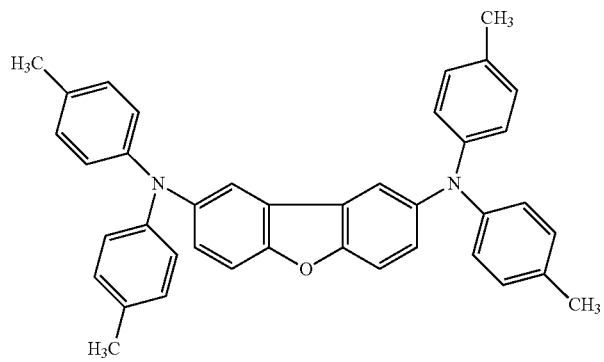<br>(C-1) | 247 |
| 4 | 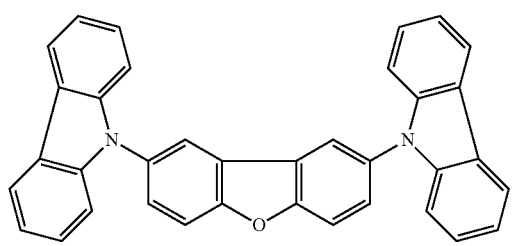<br>(C-2) | 290 |
| 5 | 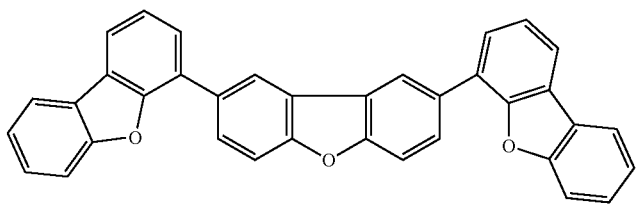<br>(A-9) | 255 |
| 6 | 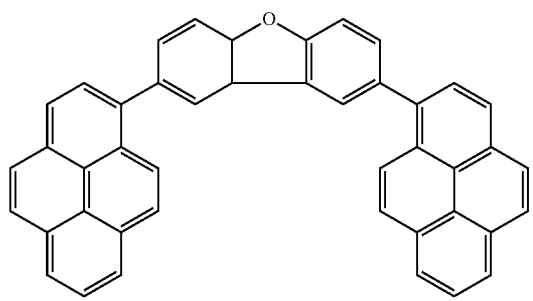<br>(A-10) | |

| Example | Structure | Mp. [° C.] |
|---|---|---|
| 7 | (A-7) | 230 |
| 8 | (A-11) | |
| 9 | (A-12) | |
| 10 | (B-2) | |

Example 11

Synthesis of 2-Phenanthren-9-yl-8-pyren-1-yl-dibenzofuran

11a) 2-Bromodibenzofuran

Bromine (23.8 g, 0.156 mol) in acetic acid (5 g) is added at 50° C. to a solution of dibenzofuran (25 g, 0.149 mol) in acetic acid (230 g). The mixture is then stirred at 50° C. for 4 hours. The reaction mixture is cooled to room temperature and poured into H$_2$O. The orange solid is washed with Na$_2$S$_2$O$_3$ aq. and H$_2$O. The crude product is then purified by recrystallization from toluene/CH$_2$Cl$_2$, wherein the pure product is obtained as a white solid (13% yield).

$^1$H-NMR (CDCl$_3$, ppm): 7.59-7.73 (m, 5H), 7.90 (d, 1H), 8.70 (d, 1H)

11b) 2-Bromo-8-iododibenzofuran

2-Bromodibenzofuran (2.5 g, 10.1 mmol), orthoperiodic acid (0.49 g, 2.15 mmol), iodine (1.02 g, 4.02 mmol), sulfuric acid, H$_2$O (2 ml) and acetic acid (10 ml) are put into a reaction vessel and the mixture is stirred at 70° C. for 3 hours. After cooling to room temperature the reaction mixture is poured into water and filtered. The white solid is washed by methanol and the desired product is obtained (1.92 g, 51%).

$^1$H-NMR (CDCl$_3$, ppm): 7.34 (d, 1H), 7.44 (d, 1H), 7.57 (dd, 1H), 7.75 (dd, 1H), 8.01 (d, 1H), 8.22 (d, 1H)

11c) 2-Bromo-8-pyren-1-yl-dibenzofuran

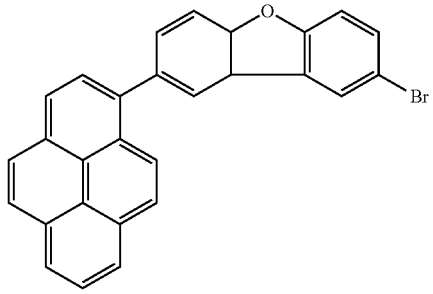 [SMILES: Brc1ccc2c(c1)C1C=C(c3ccc4ccc5cccc6ccc3c4c56)C=CC1O2]

20% aq. solution of tetraethylammoninm hydroxide (5.33 g, 7.24 mmol), tetrakis-(triphenylphosphine)palladium(0) (200 mg) and 1-(4,4,5,5-tetramethyl-1,3,2-dioxaboran-2-yl)pyrene (1.74 g, 5.3 mmol) are added to a solution of the product of example 11 b) (1.81 g, 4.83 mmol) in N,N'-dimethylacetamide (DMA) (70 ml). The mixture is then stirred at 120° C. for 3 hours. The reaction mixture is cooled down to room temperature and poured into H$_2$O. A gray crude product is obtained after filtration and washing with n-hexane. The crude product is purified by silicagel column chromatography with hexane/CH$_2$Cl$_2$-, which result in a white solid (71% yield).

$^1$H-NMR (CDCl$_3$, ppm): 7.53 (d, 1H), 7.61 (dd, 1H), 7.75 (d, 2H), 8.01-8.28 (m, 12H)

(A-17)

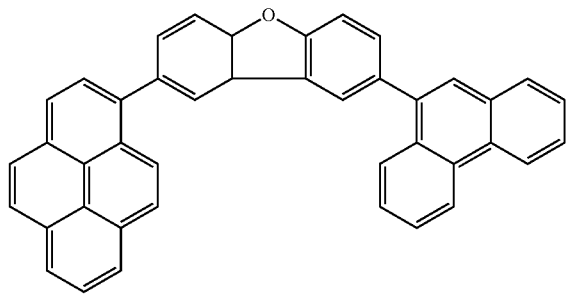

11d) 2-Phenanthren-9-yl-8-pyren-1-yl-dibenzofuran (A-17) is prepared in analogy to example 2b) using the compound obtained in step 11c) and 9-(4,4,5,5-tetramethyl-1,3,2-dioxaboran-2-yl)phenanthrene.

$^1$H-NMR (CDCl$_3$, ppm): 7.53-7.57 (m, 1H), 7.60-7.70 (m, 4H), 7.74-7.83 (m, 4H), 7.90-8.00 (m, 2H), 8.01-8.09 (m, 3H), 8.15 (d, 2H), 8.15-8.26 (m, 6H), 8.74 (d, 1H), 8.80 (d, 1H)

The compounds of examples 12 and 13, which are shown below, are prepared in analogues manner to example 11 using the appropriate educts.

Example 12

Diphenyl-[4-(8-pyren-1-yl-dibenzofuran-2-yl)-phenyl]-amine (A-43)

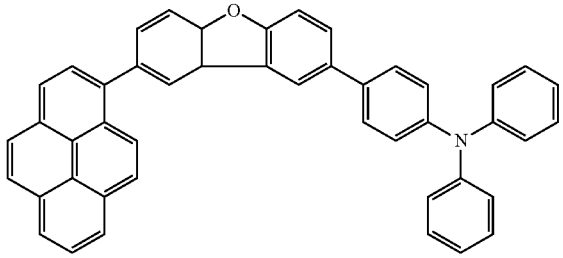

$^1$H-NMR (CDCl$_3$, ppm): 7.00-7.06 (m, 2H), 7.12-7.18 (m, 6H), 7.24-7.28 (m, 3H), 7.54-7.58 (d, 2H), 7.64-7.78 (m, 4H), 8.01-8.28 (m, 12H)

Example 13

2-Naphthalen-2-yl-8-pyren-1-yl-dibenzofuran (A-50)

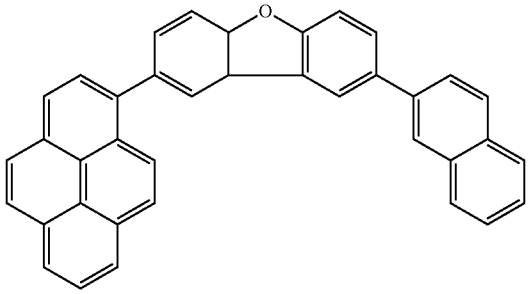

$^1$H-NMR (CDCl$_3$, ppm): 7.46-7.53 (m, 2H), 7.73-7.96 (m, 8H), 8.01-8.15 (m, 6H), 8.17-8.29 (m, 5H), 8.32 (d, 1H)

Example 14

9,10-Bis-dibenzofuran-4-yl-2,6-di-tert-butyl-anthracen (B-14)

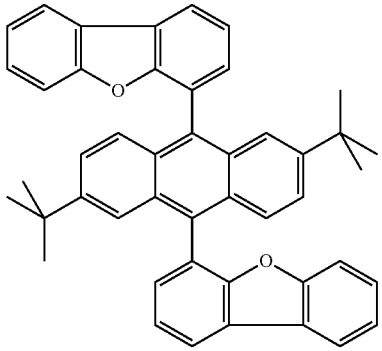

Compound B-14 is prepared in analogues manner to example 2 using the appropriate educts.

$^1$H-NMR (CDCl$_3$, ppm): 1.15 (s, 18H), 7.35-7.43 (m, 8H), 7.58-7.67 (m, 8H), 8.08-8.12 (m, 2H), 8.18 (dd, 2H)

Example 15

Synthesis of 4-(2,6-Di-tert-butyl-10-naphthalen-2-yl-anthracen-9-yl)-dibenzofuran 15a) 9-Bromo-2,6-di-tert-butyl-anthracene Bromine (3.02 g, 18.9 mmol) is added at 0° C. to a solution of 2,6-di-tert-butylanthracene (5.0 g, 17.2 mol) in carbontetrachloride (200 ml). The mixture is then stirred at 0° C. for 15 hours. After allowing to heat up to room temperature, half the amount of solvent is evaporated and the resulting mixture is poured into methanol. The precipitate is collected by filtration, recrystallized from n-hexane/methanol and the desired product is obtained as a white solid (1.13 g).

$^1$H-NMR (CDCl$_3$, ppm): 1.47 (s, 9H), 1.48 (s, 9H), 7.58 (dd, 1H), 7.67 (dd, 1H), 7.85 (d, 1H), 7.91 (d, 1H), 8.33 (s, 1H), 8.38 (d, 1H), 8.43 (d, 1H)

15b) 9-Bromo-2,6-di-tert-butyl-10-iodo-anthracene

Iodination is done in the same manner as described in example 11b) using the compound obtained in example 15a) as starting material.

$^1$H-NMR (CDCl$_3$, ppm): 1.48 (2s, 18H), 7.65-7.72 (m, 2H), 8.42-8.52 (m, 4H)

15c) 4-(10-Bromo-2,6-di-tert-butyl-anthracen-9-yl)-dibenzofuran

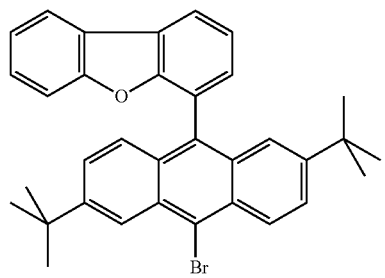 [SMILES: CC(C)(C)c1ccc2c(-c3cccc4c3oc3ccccc34)c3cc(C(C)(C)C)ccc3c(Br)c2c1]

The compound shown above is prepared in the same manner as described in example 11c) using the compound obtained in example 15b) and 1-dibenzofuranylboronic acid as starting materials.

$^1$H-NMR (CDCl$_3$, ppm): 1.18 (s, 9H), 1.46 (s, 9H), 7.29-7.33 (m, 1H), 7.35-7.42 (m, 3H), 7.48-7.59 (m, 4H), 7.68 (dd, 1H), 8.07 (m, 1H), 8.15 (dd, 1H), 8.53 (d, 1H), 8.58 (d, 1H)

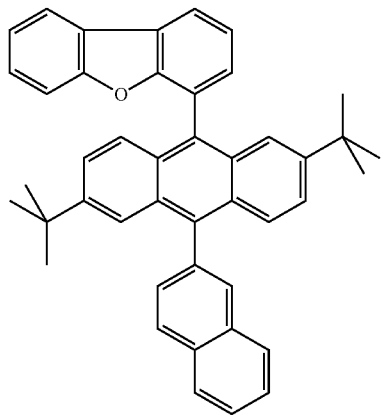

(A-35)

15d) 4-(2,6-Di-tert-butyl-10-naphthalen-2-yl-anthracen-9-yl)-dibenzofuran (A-35) is prepared in the same manner as described in example 2b) using the compound obtained in step 15c) and 2-(4,4,5,5-tetramethyl-1,3,2-dioxaboran-2-yl)naphthalene as starting materials.

$^1$H-NMR (CDCl$_3$, ppm): 1.16 (s, 9H), 1.21 (s, 9H), 7.35-7.42 (m, 5H), 7.55-7.73 (m, 9H), 7.92-7.97 (m, 1H), 8.01-8.11 (m, 4H), 8.16-8.19 (m, 1H)

Example 16

4-(2,6-Di-tert-butyl-10-pyren-1-yl-anthracen-9-yl)-dibenzofuran

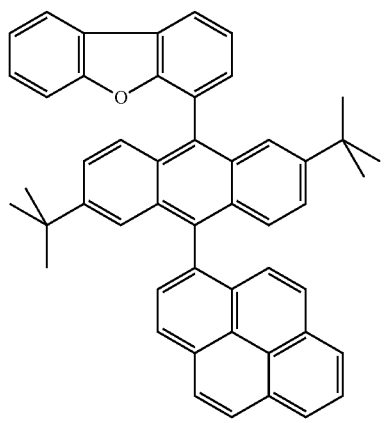

(A-36)

Example 15 is repeated except using 1-(4,4,5,5-tetramethyl-1,3,2-dioxaboran-2-yl)pyrene in the last step.

$^1$H-NMR (CDCl$_3$, ppm): 1.05 (s, 9H), 1.14 (s, 9H), 7.24-8.44 (m, 22H)

Example 17

2,6-Di-pyren-1-yl-dibenzofuran 17a) 6-Bromo-2-iodo-dibenzofuran

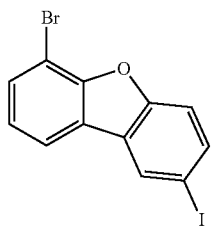 [SMILES: Brc1cccc2c1oc1ccc(I)cc12]

6-Bromo-2-iodo-dibenzofuran is prepared in the same manner as described in example 11b), except using 4-bromodibenzofurane as a starting material.

$^1$H-NMR (CDCl$_3$, ppm): 7.22-7.27 (t, 1H), 7.42-7.45 (d, 1H), 7.62-7.66 (dd, 1H), 7.75-7.79 (dd, 1H), 7.82-7.85 (dd, 1H), 8.26 (d, 1H)

17b) 6-Bromo-2-pyren-1-yl-dibenzofuran

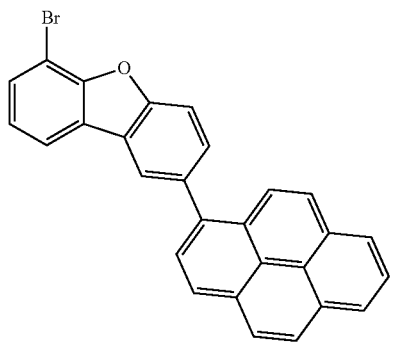 [SMILES: Brc1cccc2c1oc1ccc(-c3ccc4ccc5cccc6ccc3c4c56)cc12]

6-Bromo-2-pyren-1-yl-dibenzofuran is prepared in the same manner as described in example 11c), except using 6-Bromo-2-iodo-dibenzofuran as a starting material.

$^1$H-NMR (CDCl$_3$, ppm):7.24-7.28 (t, 1H), 7.65-7.68 (dd, 1H), 7.74-7.77 (dd, 1H), 7.82-7.85 (d, 1H), 7.91-7.94 (dd, 1H), 8.01-8.06 (m, 3H), 8.12-8.27 (m, 7H)

17c) 2,6-Di-pyren-1-yl-dibenzofuran (A-58)

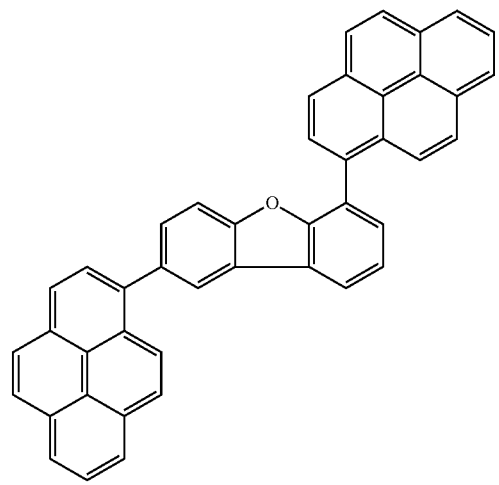

(A-58)

A-58 is prepared in analogy to A-17 using the appropriate educts.

$^1$H-NMR (CDCl$_3$, ppm):7.58-7.62 (m, 2H), 7.67-7.74 (m, 2H), 8.02-8.10 (m, 6H), 8.13-8.30 (m, 13H), 8.35-8.38 (d, 1H)

Example 18

6-Phenanthren-9-yl-2-pyren-1-yl-dibenzofuran

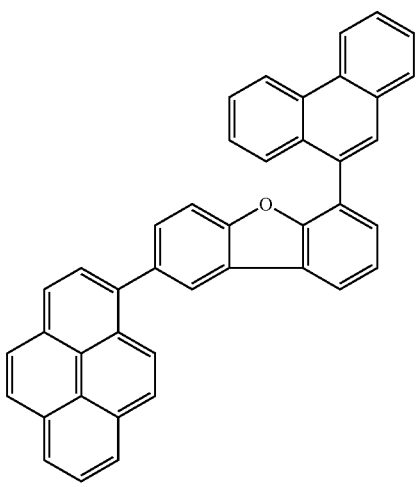

(A-59)

A-59 is prepared in analogy to A-58 using the appropriate educts.

$^1$H-NMR (CDCl$_3$, ppm):7.52-7.61 (m, 3H), 7.63-7.80 (m, 6H), 7.95-8.28 (m, 13H), 8.80-8.83 (d, 1H), 8.84-8.88 (d, 1H)

Example 19

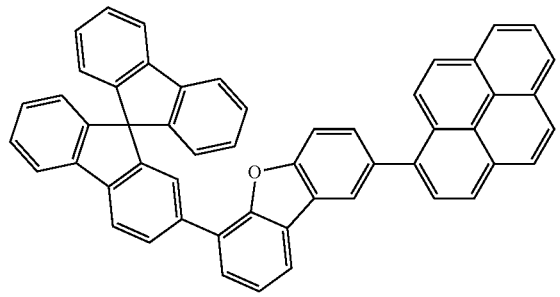

(A-60)

A-60 is prepared in analogy to A-17 using the appropriate educts.

$^1$H-NMR (CDCl$_3$, ppm):6.64-6.89 (m, 5H), 7.04-7.46 (m, 11H), 8.0-8.26 (m, 14H)

Example 20

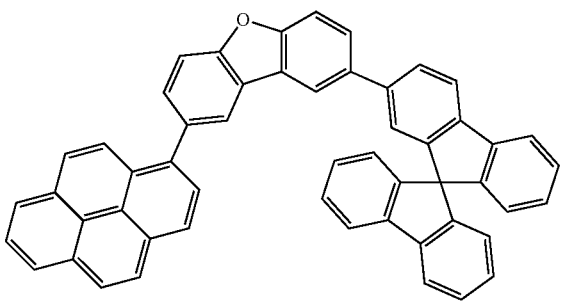

(A-61)

A-61 is prepared in analogy to A-58 using the appropriate educts.

$^1$H-NMR (CDCl$_3$, ppm): 6.62-6.86 (m, 5H), 7.02-7.14 (m, 5H), 7.30-7.40 (m, 5H), 7.58 (s, 1H), 7.66-8.26 (m, 14H)

APPLICATION EXAMPLES

Application Example 1

Compounds A-1, B-1, C-1, C-2, A-9, A-10 and A-7, respectively are deposited under vacuum on a glass plate in a thickness of 60 nm. Fluorescence spectra of the deposited films are measured by fluorescence spectrophotometer (F-4500, HITACHI). The emission $\lambda_{max}$ is shown below.

| Compound | Emission $\lambda_{max}$ [nm] |
|---|---|
| A-1 | 421 |
| B-1 | 383 |
| C-1 | 420 |
| C-2 | 387 |
| A-9 | 364 |
| A-10 | 474 |
| A-7 | 454 |

Application Example 2

The following device structure is prepared: ITO/CuPC/TCTA/Compound B-1/TPBI/LiF/Al where ITO is indium tin oxide, CuPC is copper phthalocyanine, TCTA is 4,4',4"-tri-(N-carbazoyl)triphenylamine and TPBI is 1,3,5-tris-(N-phenyl-benzimidazol-2-yl)benzene. Using this device structure, a brightness of 50 cd/m$^2$ is observed at 100 mA/cm$^2$.

Application Example 3

The following device structure is prepared: ITO/CuPC/TCTA/Compound B-1+Compound G-1 (1.1% by weight)/TPBI/LiF/Al. Using this device structure, a brightness of 500 cd/m$^2$ is observed at 100 mA/cm$^2$.

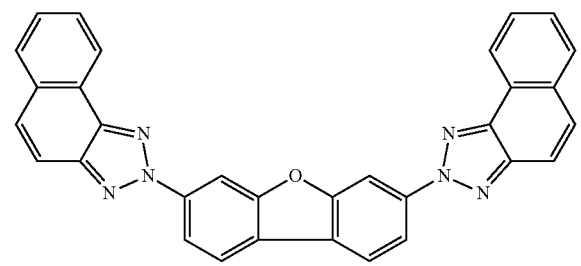

Compound G-1

(WO03105538)

Application Example 4

The following device structure is prepared: ITO/CuPC/TCTA/Compound C-2/TPBI/LiF/Al. Using this device structure, a brightness of 120 cd/m$^2$ is observed at 100 mA/cm$^2$.

Application Example 5

The following device structure is prepared: ITO/CuPC/TCTA/Compound C-2+Compound G-1 (1.9% by weight)/TPBI/LiF/Al. Using this device structure, a brightness of 70 cd/m$^2$ is observed at 100 mA/cm$^2$.

Application Example 6

The following device structure is prepared: ITO/CuPC/NPD/Compound B-1/TPBI/LiF/Al where NPD is N,N'-Di (naphthalene-1-yl)-N,N'-diphenyl-benzidine. Using this device structure, a brightness of 370 cd/m$^2$ is observed at 100 mA/cm2.

Application Example 7

The following device structure is prepared: ITO/CuPC/NPD/Compound B-1+TBPe (1.4%)/TPBI/LiF/Al where TPBe is 2,5,8,11-tetra-t-butylperylene. Using this device structure, a brightness of 680 cd/m$^2$ is observed at 88 mA/cm$^2$.

Application Example 8

The following device structure is prepared: ITO/CuPC/NPD/Compound A-10/TPBI/LiF/Al. Using this device structure, a brightness of 3,800 cd/m$^2$ is observed at 111 mA/cm2.

Application Example 9

The following device structure is prepared: ITO/CuPC/NPD/Compound A-10+TBPe (1.5%)/TPBI/LiF/Al. Using this device structure, a brightness of 2,030 cd/m² is observed at 90 mA/cm².

Application Examples 10 to 21

The following device structure is prepared: ITO/CuPC/NPD/Emitting layer (dibenzofuran of the present invention as a host+TBPe as a guest)/TPBI/LiF/Al. Using this device structure, bright blue EL emission is observed. The EL properties of the devices are summarized in Table 1.

TABLE 1

EL properties obtained in application exampleS 10 TO 21

| Application Example | Host | Guest (TBPe) Concentration (%) | Brightness (cd/m²) | Current Efficiency (cd/A) | Voltage (V) | Emission peak (nm) |
|---|---|---|---|---|---|---|
| 10 | C-2 | 2.4 | 158 | 2.5 | 10 | 467, 493 |
| 11 | C-1 | 1.7 | 99 | 1.1 | 7 | 462, 489 |
| 12 | A-17 | — | 133 | 3.3 | 7.4 | 465 |
| 13 | A-17 | 1.6 | 79 | 4.0 | 7.2 | 467, 492 |
| 14 | B-14 | — | 86 | 2.2 | 7.6 | 459 |
| 15 | B-14 | 1.8 | 97 | 4.9 | 7.1 | 462, 490 |
| 16 | A-57 | — | 108 | 2.7 | 8.3 | 460 |
| 17 | A-57 | 1.6 | 95 | 2.4 | 8.1 | 464, 489 |
| 18 | A-43 | — | 120 | 3.0 | 5.1 | 461 |
| 19 | A-43 | 1.5 | 96 | 4.8 | 4.7 | 465, 491 |
| 20 | A-50 | — | 139 | 3.5 | 6.8 | 466 |
| 21 | A-50 | 1.5 | 88 | 4.4 | 6.4 | 467, 492 |
| 22 | A-35 | — | 86 | 4.3 | 7.6 | 467 |
| 23 | A-35 | 1.3 | 98 | 4.9 | 7.4 | 461, 488 |
| 24 | A-58 | — | 104 | 5.2 | 6.4 | 465 |
| 25 | A-58 | 2.1 | 89 | 4.4 | 6.7 | 467, 490 |

Application Example 26

The following device structure is prepared: ITO/CuPC/NPD/Emitting layer (dibenzofuran of the present invention as a host+dibenzofuran of the present invention as a guest)/TPBI/LiF/Al. Using this device structure, bright blue EL emission is observed. The EL properties of the device is summarized in Table 2.

TABLE 2

EL properties obtained in application example 26

| Application Example | Host | Guest | Brightness (cd/m²) | Current Efficiency (cd/A) | Voltage (V) | Emission Peak (nm) |
|---|---|---|---|---|---|---|
| 26 | A-17 | B-14 (5.1%) | 83 | 2.1 | 7.5 | 462 |

The invention claimed is:

1. A compound of the formula (II)

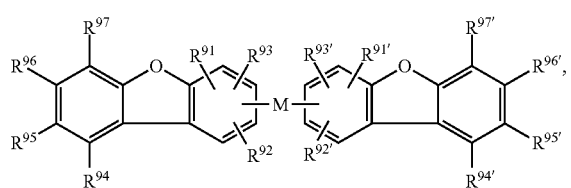

wherein $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ are independently of each other H, —$OR^{201}$, —$SR^{202}$ and/or —$NR^{203}R^{204}$, $C_1$-$C_{24}$alkyl; $C_1$-$C_{24}$alkyl, which is substituted by E and/or interrupted by D; $C_2$-$C_{18}$alkenyl, $C_2$-$C_{18}$alkenyl, which is substituted by E, $C_3$-$C_8$cycloalkyl, $C_3$-$C_8$cycloalkyl, which is substituted by G, aryl, aryl, which is substituted by G, heteroaryl, or heteroaryl, which is substituted by G, silyl, $=\!\!\!=\!\!\!=\!\!\mathrm{SiR}^{62}R^{63}R^{64}$, —CN, cyclic ether, —$B(OR^{65})_2$ and/or halogen, or $R^{97}$ and $R^{96}$, $R^{96}$ and $R^{95}$, $R^{95}$ and $R^{94}$, $R^{97'}$ and $R^{96'}$, $R^{96'}$ and $R^{95'}$, $R^{95'}$ and/or $R^{94'}$, and/or two of the groups $R^{91}$, $R^{92}$ and $R^{93}$ or $R^{91'}$, $R^{92'}$ and $R^{93'}$, which are in neighbourhood to each other, together form a group

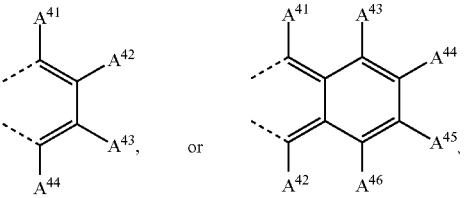

wherein $A^{41}$, $A^{42}$, $A^{43}$, $A^{44}$, $A^{45}$, and $A^{46}$ are independently of each other H, halogen, hydroxy, $C_1$-$C_{24}$alkyl, $C_1$-$C_{24}$alkyl which is substituted by E and/or interrupted by D, $C_1$-$C_{24}$ perfluoroalkyl, $C_5$-$C_{12}$cycloalkyl, $C_5$-$C_{12}$cycloalkyl which is substituted by G and/or interrupted by S—, —O—, or —$NR^5$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by E, or —CO—$R^8$, wherein $R^{201}$ is hydrogen, $C_1$-$C_{24}$alkyl, $C_1$-$C_{24}$alkyl, which is substituted by E and/or interrupted by D; $C_2$-$C_{12}$alkenyl, $C_3$-$C_6$alkenoyl, $C_3$-$C_8$cycloalkyl, or benzoyl, each of which may optionally be substituted by one or more groups $C_1$-$C_6$alkyl, halogen, —OH and/or $C_1$-$C_4$alkoxy; $C_6$-$C_{14}$aryl, phenyl, naphthyl, phenanthryl, anthranyl, or pyrenyl, each of which may optionally be substituted by halogen, —OH, $C_1$-$C_{12}$alkyl, $C_1$-$C_{12}$alkoxy, phenoxy, $C_1$-$C_{12}$alkylsulfanyl, phenylsulfanyl, —N($C_1$-$C_{12}$alkyl)$_2$ and/or diphenylamino;

$R^{202}$ is $C_1$-$C_{24}$alkyl, $C_1$-$C_{24}$alkyl, which is substituted by E and/or interrupted by D; $C_2$-$C_{12}$alkenyl, $C_1$-$C_8$alkanoyl, $C_2$-$C_{12}$alkenyl, $C_3$-$C_6$alkenoyl; $C_3$-$C_8$cycloalkyl, or benzoyl, each of which may optionally be substituted by one or more groups $C_1$-$C_6$alkyl, halogen, —OH, $C_1$-$C_4$alkoxy or $C_1$-$C_4$alkylsulfanyl; $C_6$-$C_{14}$aryl, phenyl, naphthyl, phenanthryl, anthranyl, or pyrenyl, each of which may optionally be substituted by halogen, $C_1$-$C_{12}$alkyl, $C_1$-$C_{12}$alkoxy, phenyl-$C_1$-$C_3$alkyloxy, phenoxy, $C_1$-$C_{12}$alkylsulfanyl, phenylsulfanyl, —N($C_1$-$C_{12}$alkyl)$_2$, diphenylamino, —(CO)O($C_1$-$C_8$alkyl), —(CO)—$C_1$-$C_8$alkyl, or (CO)N($C_1$-$C_8$alkyl)$_2$;

$R^{203}$ and $R^{204}$ are independently of each other hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, or benzoyl, each of which may optionally be substituted by one or more groups $C_1$-$C_6$alkyl, halogen, —OH, or $C_1$-$C_4$alkoxy; phenyl-$C_1$-$C_3$alkyl, $C_1$-$C_8$alkanoyl, $C_3$-$C_{12}$alkenoyl, $C_6$-$C_{14}$aryl, phenyl naphthyl, phenanthryl, anthranyl, or pyrenyl, each of which is optionally substituted by $C_1$-$C_{12}$alkyl, benzoyl or $C_1$-$C_{12}$alkoxy; or $R^{203}$ and $R^{204}$ together are $C_2$-$C_8$alkylene, or branched $C_2$-$C_8$alkylene optionally interrupted by —O—, —S—, or —NR²⁰⁵— and/or optionally substituted by hydroxyl, $C_1$-$C_4$alkoxy, $C_2$-$C_4$alkanoyloxy, or benzoyloxy, wherein the ring formed by $R^{203}$ and $R^{204}$ can optionally be condensed one or two times by phenyl which can be substituted one to three times with $C_1$-$C_8$-alkyl, $C_1$-$C_8$-alkoxy, halogen, or cyano;

$R^{205}$ is hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, phenyl-$C_1$-$C_3$alkyl, $C_1$-$C_8$alkanoyl, $C_3$-$C_{12}$alkenoyl, $C_6$-$C_{14}$aryl, benzoyl; phenyl, naphthyl, phenanthryl, anthranyl, or pyrenyl, each of which is optionally substituted by $C_1$-$C_{12}$alkyl, benzoyl, or $C_1$-$C_{12}$alkoxy;

D is —CO—, —COO—, —OCOO—, —S—, —SO—, —SO₂—, —O—, —NR⁵—, —SiR⁶¹R⁶²—, —POR⁵—, —CR⁶³=CR⁶⁴—, or —C≡C—;

E is halogen, $C_6$-$C_{14}$aryl, phenyl, naphthyl, phenanthryl, anthranyl, or pyrenyl, which may be substituted by —OR⁵, —SR⁵, —NR⁵R⁶, =SiR⁶²R⁶³R⁶⁴, wherein $R^{62}$, $R^{63}$ and $R^{64}$ are independently of each other a $C_1$-$C_8$alkyl group, a $C_6$-$C_{24}$aryl group or a $C_7$-$C_{12}$aralkylgroup, —CN, cyclic ether and/or —B(OR⁶⁵)₂, wherein $R^{65}$ is hydrogen, $C_1$-$C_{24}$alkyl, $C_3$-$C_8$cycloalkyl, $C_7$-$C_{24}$aralkyl, $C_2$-$C_{18}$alkenyl, $C_2$-$C_{24}$alkynyl, hydroxy, mercapto, $C_1$-$C_{24}$alkoxy, $C_1$-$C_{24}$alkylthio, $C_6$-$C_{30}$ aryl, $C_2$-$C_{30}$ heteroaryl, halogen, fluorine, haloalkane, silyl, siloxanyl, and an alicyclic ring formed with adjacent substituents $R^{65}$; —OR⁵, —SR⁵, —NR⁵R⁶, —COR⁸, —COOR⁷, —CONR⁵R⁶, —CN, halogen, silyl, $C_1$-$C_{18}$alkyl, or heteroaryl, G is E, or $C_1$-$C_{18}$alkyl, wherein $R^5$ and $R^6$ are independently of each other H, $C_6$-$C_{18}$aryl; $C_6$-$C_{18}$aryl which is substituted by $C_1$-$C_{18}$alkyl, $C_1$-$C_{18}$alkoxy, or silyl; $C_1$-$C_{18}$alkyl or $C_1$-$C_{18}$alkyl which is interrupted by —O—; or $R^5$ and $R^6$ together form a five or six membered ring, $R^7$ is H, $C_6$-$C_{18}$aryl, $C_7$-$C_{12}$alkylaryl, which are optionally substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^8$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, $C_7$-$C_{12}$alkylaryl, or $C_1$-$C_{18}$alkyl which is interrupted by —O—;

$R^{61}$ and $R^{62}$ are independently of each other $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—, and $R^{63}$ and $R^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—; wherein at least one of the groups $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ is a group

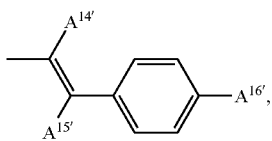

wherein $A^{14'}$ and $A^{15'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, and $A^{16'}$ is H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G; or a polycyclic aryl group, pentalenyl, indenyl, azulenyl, naphthyl, biphenylenyl, as-indacenyl, s-indacenyl, acenaphthylenyl, fluorenyl, phenanthryl, anthracenyl, fluoran-thenyl, acephenanthrylenyl, aceanthrylenyl, triphenylenyl, pyrenyl, chrysenyl, naphtha-cenyl, picenyl, perylenyl, pentacenyl, pentaphenyl, hexacenyl, or hexaphenyl, which can optionally be substituted by G, wherein D, E and G are as defined above; or wherein at least one of the groups $R^{91}$, $R^{92}$, $R^{93}$, $R^{94}$, $R^{95}$, $R^{96}$, $R^{97}$, $R^{91'}$, $R^{92'}$, $R^{93'}$, $R^{94'}$, $R^{95'}$, $R^{96'}$ and $R^{97'}$ is a group of the formula —$(W^1)_a$—$(W^2)_b$—$W^3$, wherein a and b are 0, or 1, $W^1$ and $W^2$ are independently of each other a group of formula

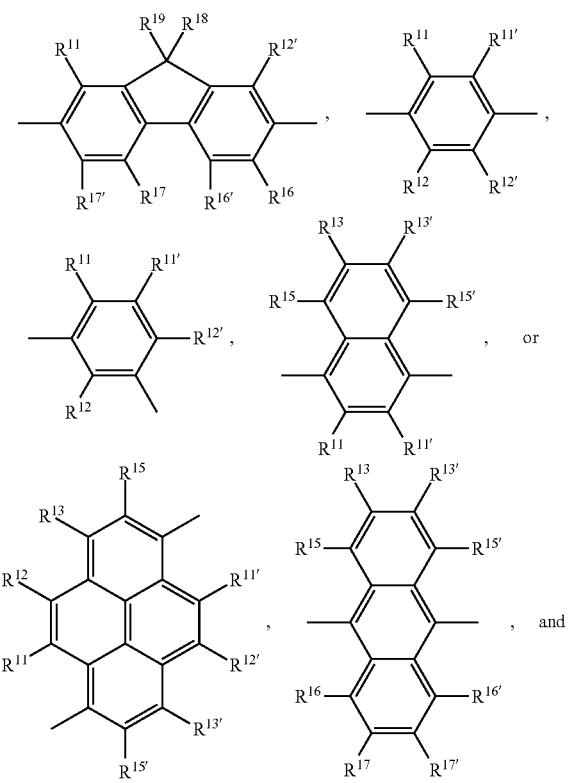

$W^3$ is a group of formula

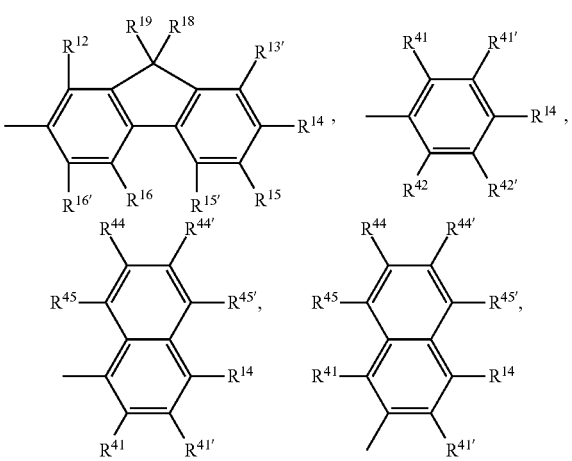

-continued

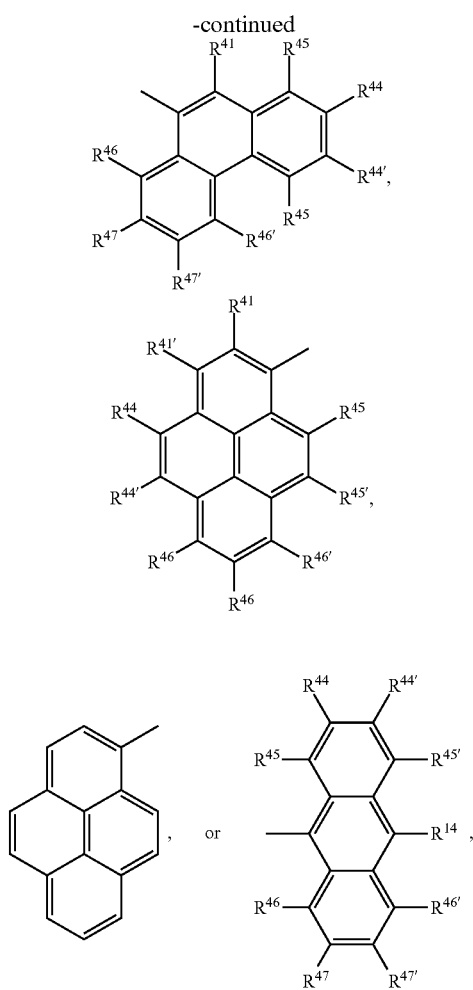

wherein
$R^{11}, R^{11'}, R^{12}, R^{12'}, R^{13}, R^{13'}, R^{15}, R^{15'}, R^{16}, R^{16'}, R^{17}, R^{17'}, R^{41}, R^{41'}, R^{42}, R^{42'}, R^{44}, R^{44'}, R^{45}, R^{45'}, R^{46}, R^{46'}, R^{47}$ and $R^{47'}$ are independently of each other H, E, silyl, such as tri($C_1$-$C_8$alkyl)silyl, $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_1$-$C_{18}$alkoxy; or $C_1$-$C_{18}$alkoxy which is substituted by E and/or interrupted by D; $C_7$-$C_{18}$aralkyl; or $C_7$-$C_{18}$aralkyl which is substituted by G;

$R^{14}$ is H, $C_1$-$C_{18}$alkyl; silyl, such as tri($C_1$-$C_8$alkyl)silyl, or $C_1$-$C_{18}$alkyl which is substituted by E and/or interrupted by D; $C_1$-$C_{18}$alkoxy; or $C_1$-$C_{18}$alkoxy which is substituted by E and/or interrupted by D;

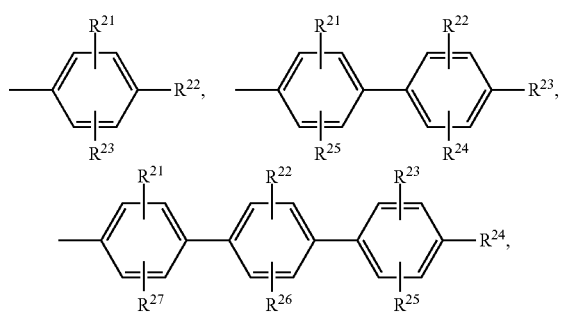

$R^{18}$ and $R^{19}$ are independently of each other $C_1$-$C_{18}$alkyl; $C_1$-$C_{18}$alkoxy, $C_6$-$C_{18}$aryl; $C_7$-$C_{18}$aralkyl;

or $R^{18}$ and $R^{19}$ together form a ring a five- or six-membered ring, which can optionally be substituted by $C_1$-$C_8$alkyl, $R^{21}, R^{22}, R^{23}, R^{24}, R^{25}, R^{26}$ and $R^{27}$ are independently of each other H, E, $C_1$-$C_{18}$alkyl; $C_1$-$C_{18}$alkyl which is substituted by E and/or interrupted by D; $C_7$-$C_{18}$aralkyl; $C_7$-$C_{18}$aralkyl which is substituted by G; or $W^3$ is a group of formula

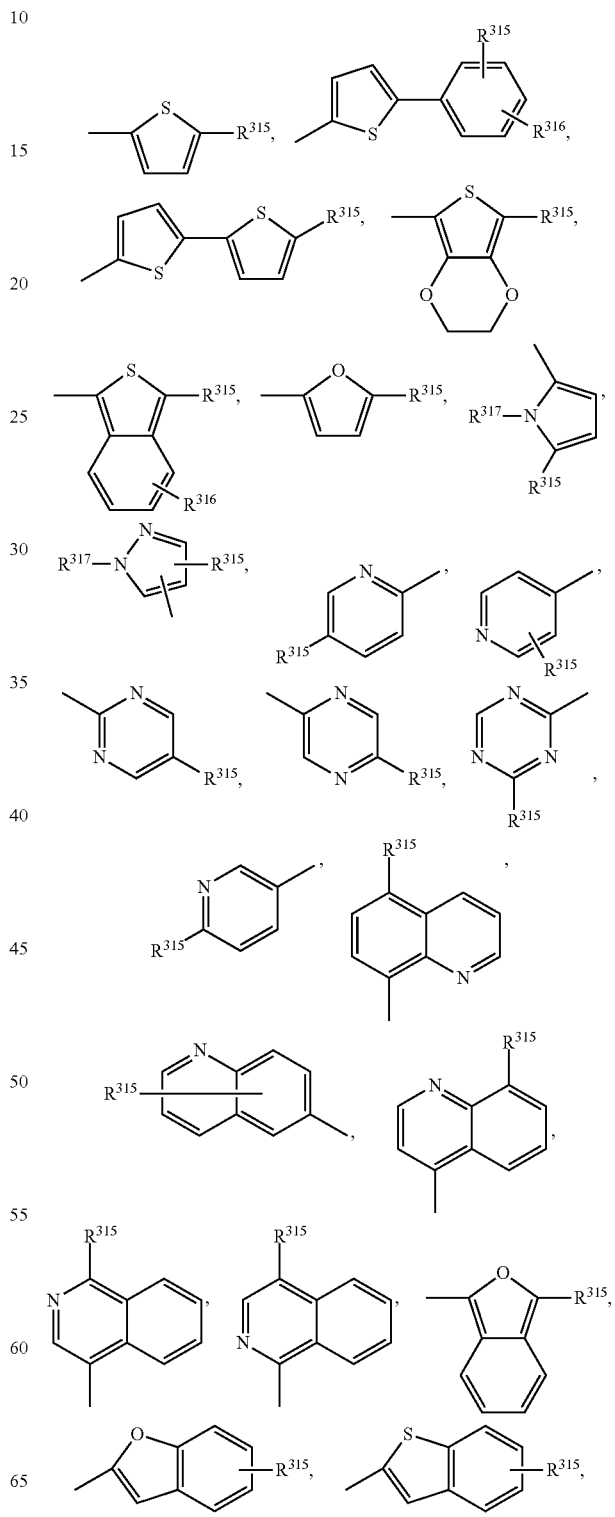

-continued

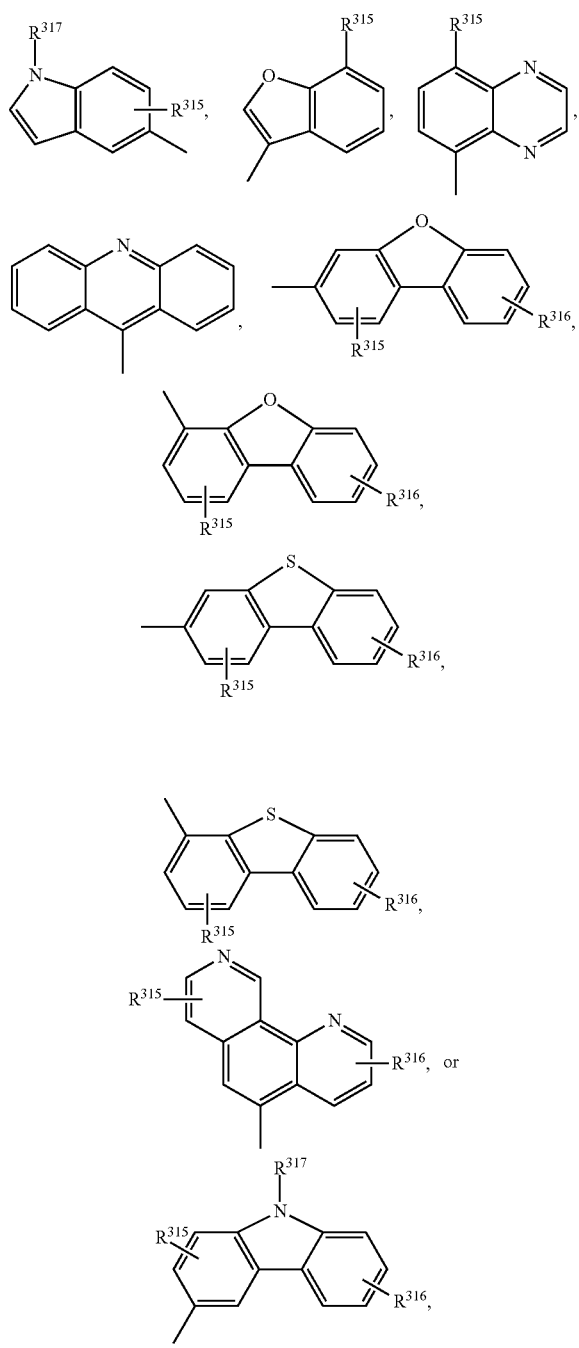

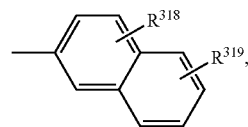

wherein
R³¹⁵ and R³¹⁶ are independently of each other a hydrogen atom, a $C_1$-$C_{18}$alkyl group, a $C_1$-$C_{18}$alkoxy group, a group of formula

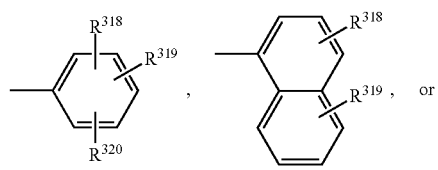

-continued

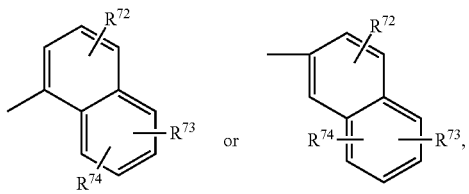

wherein $R^{318}$, $R^{319}$ and $R^{320}$ independently from each other stand for hydrogen, $C_1$-$C_8$-alkyl, $C_1$-$C_8$-alkoxy, or phenyl, and $R^{317}$ stands for is a hydrogen atom, a $C_1$-$C_{25}$alkyl group, which might be interrupted by —O—, a cycloalkyl group, a $C_7$-$C_{18}$aralkyl group, a $C_6$-$C_{18}$aryl group, or a heterocyclic group, which may be substituted by G; or wherein at least one of the groups $R^{91}$, $R^{92}$, $R^{93}$, $R^{94}$, $R^{95}$, $R^{96}$, $R^{97}$, $R^{91'}$, $R^{92'}$, $R^{93'}$m $R^{94'}$, $R^{95'}$, $R^{96'}$, and $R^{97'}$ is a group of the formula —$(W^1)_a$-$(W^2)_b$-$W^3$, wherein a and b are 0, or 1, $W^1$ and $W^2$ are as defined above, and $W^3$ is a group of formula —$NR^{70}R^{71}$, wherein $R^{70}$ and $R^{71}$ are independently of each other a group of formula

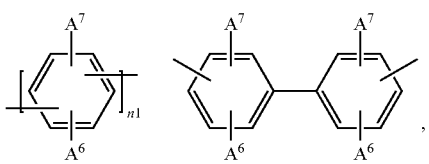

wherein $R^{72}$, $R^{73}$ and $R^{74}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group, or $R^{70}$ and $R^{71}$ together with the nitrogen atom to which they are bonded form a five or six membered heterocyclic ring, which can be condensed by one or two optionally substituted phenyl groups, M is a single bond —CO—, —COO—, —S—, —SO—, —SO₂—, —O—,

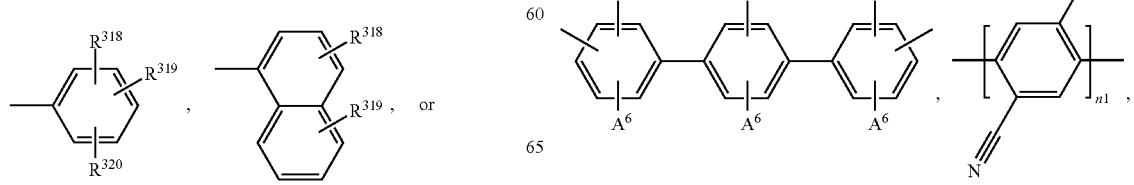

101
-continued
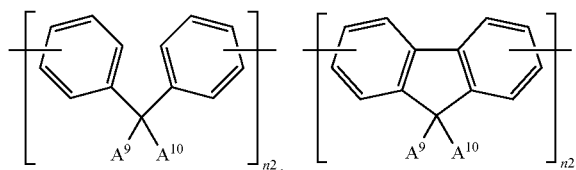
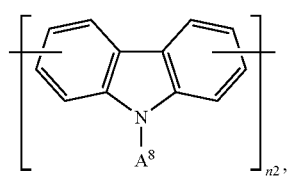
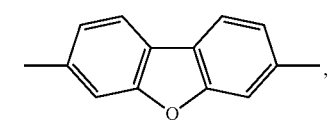
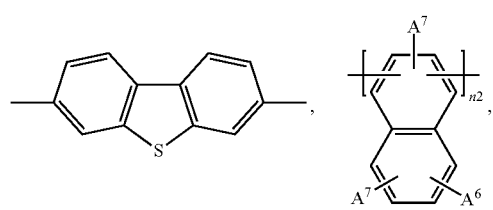
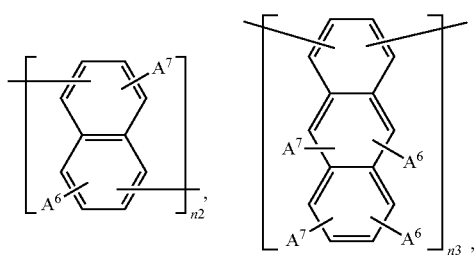
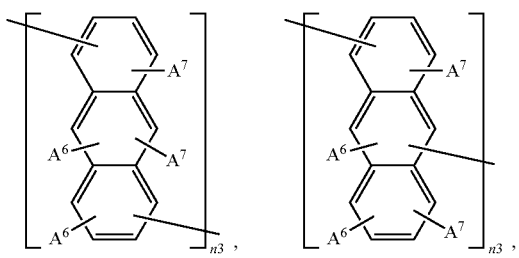
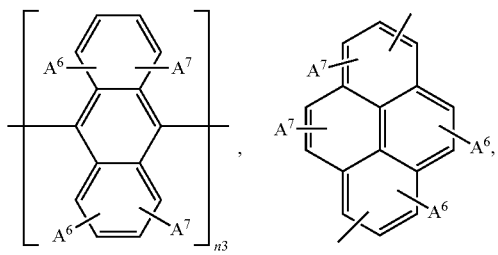
102
-continued
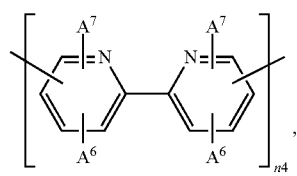
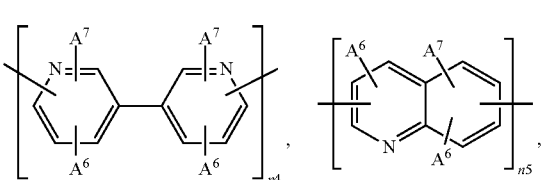
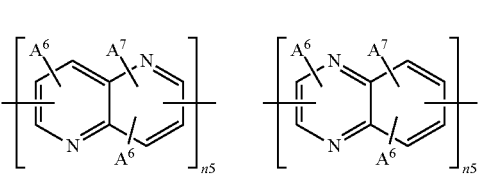
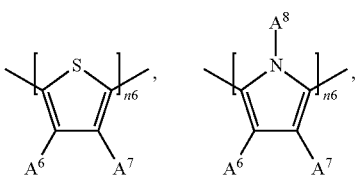
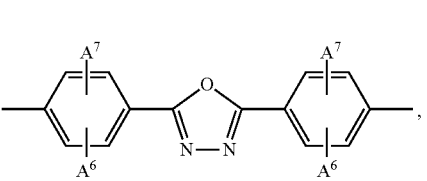
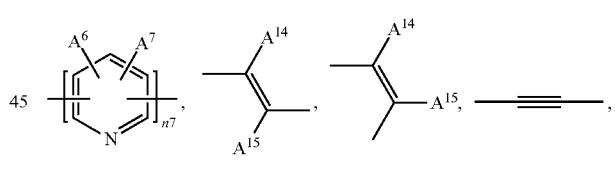
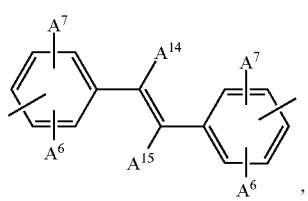
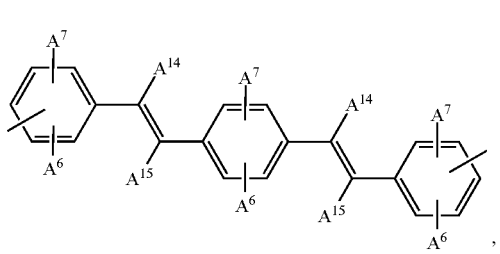
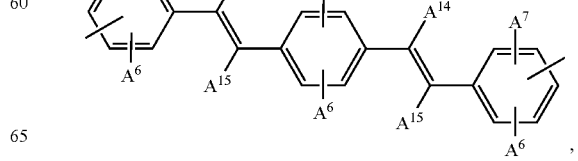

-continued

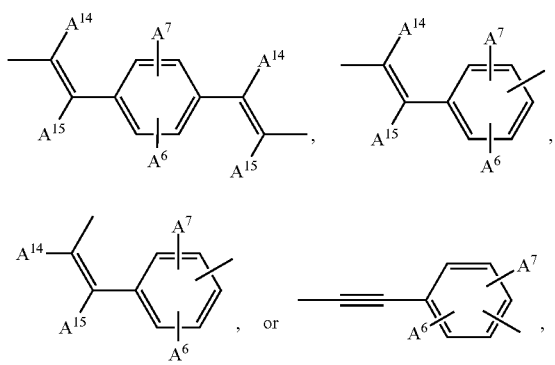

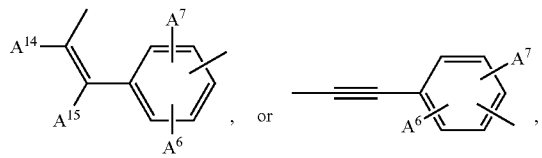

wherein
n1, n2, n3, n4, n5, n6 and n7 are integers of 1 to 10,
$A^6$ and $A^7$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{10}$alkoxy which is substituted by E' and/or interrupted by D', $C_7$-$C_{25}$aralkyl, or —CO-$A^{28}$, $A^8$ is $C_1$-$C_{18}$alkyl, $C_1$-$C_{18}$alkyl which is substituted by E' and/or interrupted by D', $C_6$-$C_{24}$ aryl, or $C_7$-$C_{25}$aralkyl, $A^9$ and $A^{10}$ are independently of each other $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', or $C_7$-$C_{25}$aralkyl, or $A^9$ and $A^{10}$ form a ring, which can optionally be substituted by one or more $C_1$-$C_{18}$ alkyl groups;

$A^{14}$ and $A^{15}$ are independently of each other H, $C_1$-$C_{18}$alkyl, $C_1$-$C_{18}$alkyl, which is substituted by E' and/or interrupted by D', $C_6$-$C_{24}$aryl, $C_6$-$C_{24}$aryl which is substituted by G', $C_2$-$C_{20}$heteroaryl, or $C_2$-$C_{20}$heteroaryl which is substituted by G', D' is —CO—; —COO—; —S—; —SO—; —$SO_2$—; —O—; —$NA^{25}$-; —$SiA^{30}A^{31}$-; —$POA^{32}$-; —$CA^{23}$=$CA^{24}$-; or —C≡C—; and E' is —$OA^{29}$; —$SA^{29}$; —$NA^{25}A^{26}$; —$COA^{28}$, —$COOA^{27}$; —$CONA^{25}A^{26}$; CN; —$OCOOA^{27}$; or halogen; G' is E', or $C_1$-$C_{18}$alkyl; wherein $A^{23}$, $A^{24}$, $A^{25}$ and $A^{26}$ are independently of each other H; $C_6$-$C_{18}$aryl;

$C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $A^{25}$ and $A^{26}$ together form a five or six membered ring, $A^{27}$ and $A^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—, $A^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $A^{30}$ and $A^{31}$ are independently of each other $C_1$-$C_{18}$alkyl, $C_6$-$C_{18}$aryl, or $C_6$-$C_{18}$aryl, which is substituted by $C_1$-$C_{18}$alkyl, $A^{32}$ is $C_1$-$C_{18}$alkyl, $C_6$-$C_{18}$aryl, or $C_6$-$C_{18}$aryl, which is substituted by $C_1$-$C_{18}$alkyl.

2. The compound of formula II according to claim 1, which is a compound of formula

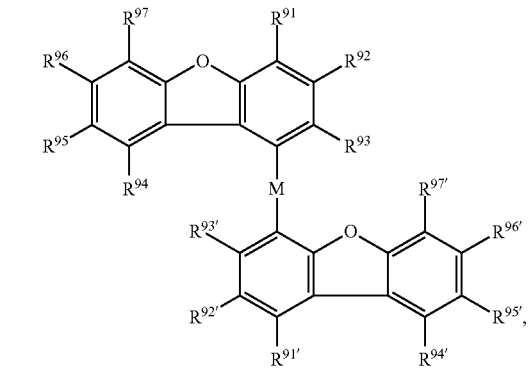

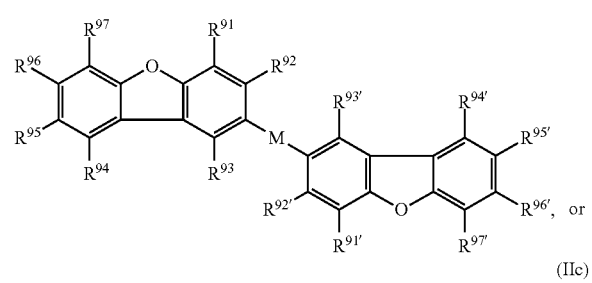

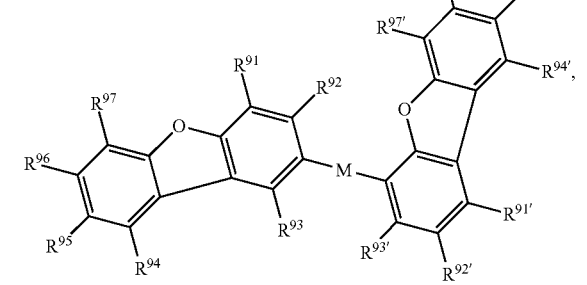

wherein M, $R^{92}$, $R^{93}$, $R^{94}$, $R^{95}$, $R^{96}$, $R^{97}$, $R^{91'}$, $R^{92'}$, $R^{93'}$, $R^{95'}$, $R^{96'}$ and $R^{97'}$ are as defined in claim 1.

3. The compound of formula II according to claim 1 which is a compound of formula

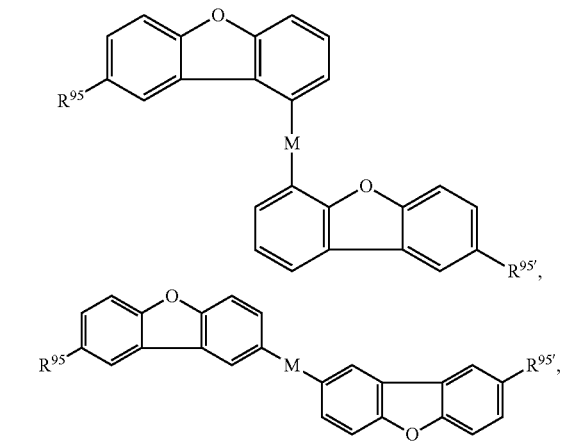

wherein $R^{95}$ and $R^{95'}$ are independently of each other $C_{10}$-$C_{14}$aryl, phenyl, naphthyl, phenanthryl, anthranyl, or pyrenyl, which may be substituted by one, or more $C_1$-$C_8$alkyl, or $C_1$-$C_8$alkoxy groups, and M is as defined in claim 1.

4. The compound of formula (B-16)

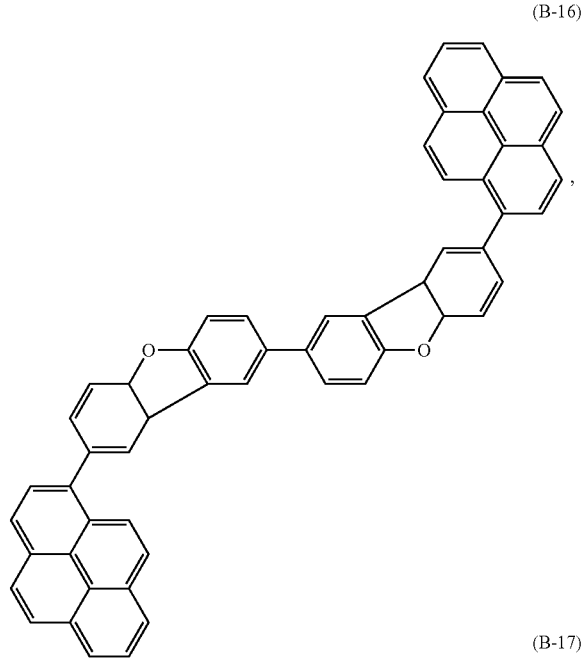

, (B-17)

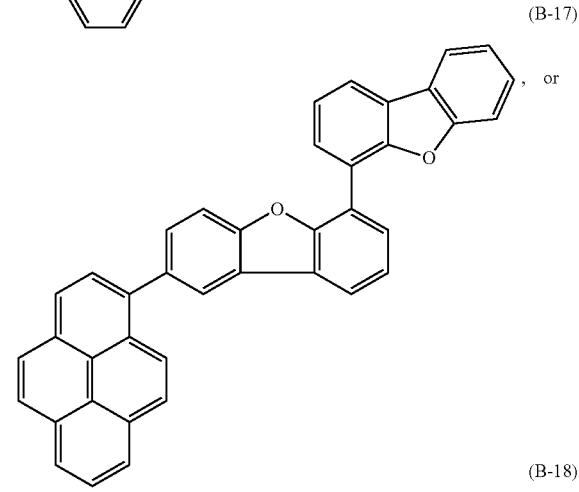

, or (B-18)

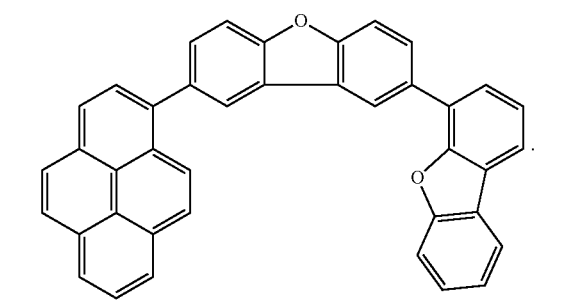

.

5. An electroluminescent device, comprising a compound according to claim 1.

6. The device of claim 5 electrophotographic photoreceptors, photoelectric converters, solar cells, image sensors, or dye lasers.

7. A compound according to claim 1, wherein M is a single bond.

8. The compound according to claim 1, wherein $W^3$ is a group of formula —$NR^{70}R^{71}$, wherein $R^{70}$ and $R^{71}$ together with the nitrogen atom to which they are bonded form a five or six membered heterocyclic ring which can be condensed by one or two optionally substituted phenyl groups and the heterocyclic ring is selected from the group consisting of

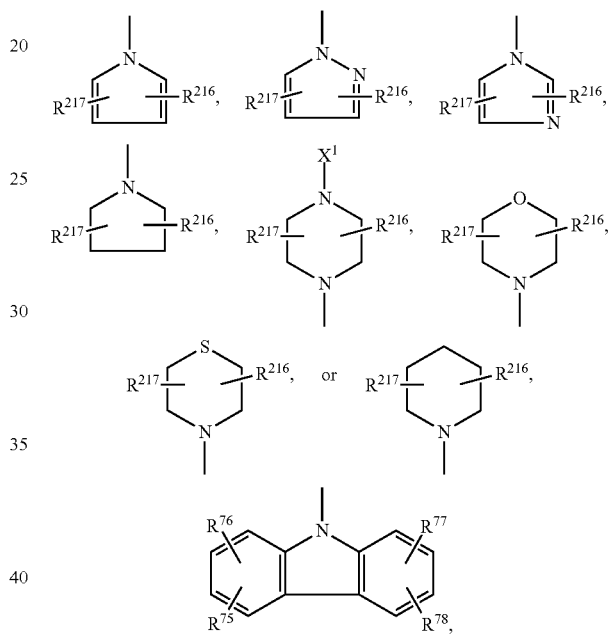

wherein $R^{216}$ and $R^{217}$ independently from each other stands for hydrogen, $C_1$-$C_8$alkyl, $C_1$-$C_8$alkoxy, or phenyl, and $X^1$ stands for hydrogen, or $C_1$-$C_8$alkyl;

$R^{75}$, $R^{76}$, $R^{77}$ and $R^{78}$ are independently of each other H, E, $C_6$-$C_{18}$aryl; $C_6$-$C_{18}$aryl which is substituted by E; $C_1$-$C_{18}$alkyl; $C_1$-$C_{18}$alkyl which is substituted by G and/or interrupted by D; $C_7$-$C_{18}$aralkyl; or $C_7$-$C_{18}$aralkyl which is substituted by E.

* * * * *